(12) United States Patent
Buchholz et al.

(10) Patent No.: US 12,090,147 B2
(45) Date of Patent: Sep. 17, 2024

(54) COMBINATION THERAPY WITH 2-(4-CHLOROPHENYL)-N-((2-(2,6-DIOXO-IPERIDIN-3-YL)-1-OXOISOINDOLIN-5-YL) METHYL)-2,2-DIFLUOROACETAMIDE

(71) Applicant: Celgene Corporation, Summit, NJ (US)

(72) Inventors: Tonia Buchholz, Moss Beach, CA (US); Jinhong Fan, San Mateo, CA (US); Daniel W. Pierce, Belmont, CA (US); Michael Pourdehnad, San Francisco, CA (US); Tsun-Wen Yao, San Francisco, CA (US)

(73) Assignee: Celgene Corporation, Summit, NJ (US)

( * ) Notice: Subject to any disclaimer, the term of this patent is extended or adjusted under 35 U.S.C. 154(b) by 333 days.

(21) Appl. No.: 17/089,359

(22) Filed: Nov. 4, 2020

(65) Prior Publication Data

US 2021/0128545 A1 May 6, 2021

Related U.S. Application Data

(60) Provisional application No. 62/931,040, filed on Nov. 5, 2019.

(51) Int. Cl.
*A61K 31/454* (2006.01)
*A61K 31/047* (2006.01)
*A61K 31/4545* (2006.01)
*A61K 31/573* (2006.01)
*A61K 31/593* (2006.01)
*A61K 33/06* (2006.01)
*A61K 38/20* (2006.01)
*A61K 39/395* (2006.01)
*A61K 45/06* (2006.01)
*C07D 401/04* (2006.01)
*C07D 401/14* (2006.01)

(52) U.S. Cl.
CPC .......... *A61K 31/454* (2013.01); *A61K 31/047* (2013.01); *A61K 31/4545* (2013.01); *A61K 31/573* (2013.01); *A61K 31/593* (2013.01); *A61K 33/06* (2013.01); *A61K 38/2006* (2013.01); *A61K 39/3955* (2013.01); *A61K 45/06* (2013.01); *C07D 401/04* (2013.01); *C07D 401/14* (2013.01)

(58) Field of Classification Search
CPC .................................................. A61K 31/454
See application file for complete search history.

(56) References Cited

U.S. PATENT DOCUMENTS

| | | |
|---|---|---|
| 4,810,643 A | 3/1989 | Souza |
| 4,999,291 A | 3/1991 | Souza |
| 5,229,496 A | 7/1993 | Deeley et al. |
| 5,391,485 A | 2/1995 | Deeley et al. |
| 5,393,870 A | 2/1995 | Deeley et al. |
| 5,528,823 A | 6/1996 | Rudy, Jr. et al. |
| 5,580,755 A | 12/1996 | Souza |
| 5,811,097 A | 9/1998 | Allison et al. |
| 5,855,887 A | 1/1999 | Allison et al. |
| 5,948,893 A | 9/1999 | June et al. |
| 6,051,227 A | 4/2000 | Allison et al. |
| 6,207,157 B1 | 3/2001 | Gu et al. |
| 6,352,694 B1 | 3/2002 | June et al. |
| 6,534,055 B1 | 3/2003 | June et al. |
| 6,682,736 B1 | 1/2004 | Hanson et al. |
| 6,692,964 B1 | 2/2004 | June et al. |
| 6,887,466 B2 | 5/2005 | June et al. |
| 6,905,681 B1 | 6/2005 | June et al. |
| 6,984,720 B1 | 1/2006 | Korman et al. |
| 7,488,802 B2 | 2/2009 | Collins et al. |
| 7,498,171 B2 | 3/2009 | Hariri et al. |
| 7,605,238 B2 | 10/2009 | Korman et al. |
| 7,943,743 B2 | 5/2011 | Korman et al. |
| 8,008,449 B2 | 8/2011 | Korman et al. |
| 8,168,757 B2 | 5/2012 | Finnefrock et al. |
| 8,217,149 B2 | 7/2012 | Irving et al. |
| 9,499,514 B2 | 11/2016 | Hansen et al. |
| 9,808,451 B2 | 11/2017 | Cathers et al. |
| 9,968,596 B2 | 5/2018 | Cathers et al. |

(Continued)

FOREIGN PATENT DOCUMENTS

| | | |
|---|---|---|
| WO | WO 2003/042402 | 5/2003 |
| WO | WO 2008/156712 | 12/2008 |

(Continued)

OTHER PUBLICATIONS

Antonopoulos et al. J Biol Chem. 2015, 290(33):20167-84.
Brignone et al., "A soluble form of lymphocyte activation gene-3 (IMP321) induces activation of a large range of human effector cytotoxic cells." The Journal of Immunology 179.6 (2007): 4202-4211.
Carta et al. J Biol Chem. 2011, 286(31):27069-80.
Chauhan et al. "BAX/BAK-induced apoptosis results in caspase-8-dependent IL-1β maturation in macrophages." Cell reports 25.9 (2018): 2354-2368.
Dhimolea Eugen. "Canakinumab." MAbs. vol. 2. No. 1. Taylor & Francis, 2010.

(Continued)

*Primary Examiner* — Rei Tsang Shiao
(74) *Attorney, Agent, or Firm* — Jones Day

(57) ABSTRACT

Provided herein are methods of treating, preventing, managing, and/or ameliorating hypotension related to administration of 2-(4-chlorophenyl)-N-((2-(2,6-dioxopiperidin-3-yl)-1-oxoisoindolin-5-yl)methyl)-2,2-difluoroacetamide or a stereoisomer or a mixture of stereoisomers, pharmaceutically acceptable salt, tautomer, prodrug, solvate, hydrate, co-crystal, clathrate, or polymorph thereof in a cancer patient, wherein the methods comprise administering a combination comprising 2-(4-chlorophenyl)-N-((2-(2,6-dioxopiperidin-3-yl)-1-oxoisoindolin-5-yl)methyl)-2,2-difluoroacetamide or a stereoisomer or a mixture of stereoisomers, pharmaceutically acceptable salt, tautomer, prodrug, solvate, hydrate, co-crystal, clathrate, or polymorph thereof and a glucocorticoid receptor agonist, an interleukin-1 receptor antagonist, or an interleukin-1β blocker.

18 Claims, 22 Drawing Sheets

(56) References Cited

U.S. PATENT DOCUMENTS

| | | | |
|---|---|---|---|
| 10,052,315 B2 | 8/2018 | Hui et al. | |
| 10,189,808 B2 | 1/2019 | Fernandez et al. | |
| 10,245,258 B2 * | 4/2019 | Carrancio | A61K 9/19 |
| 10,449,187 B2 | 10/2019 | Hui et al. | |
| 10,626,101 B2 | 4/2020 | Li et al. | |
| 11,129,821 B2 | 9/2021 | Hui et al. | |
| 11,241,423 B2 * | 2/2022 | Cathers | A61K 45/06 |
| 2016/0009683 A1 | 1/2016 | Hansen et al. | |
| 2017/0348298 A1 | 12/2017 | Carrancio et al. | |
| 2018/0221361 A1 | 8/2018 | Cathers et al. | |
| 2019/0037818 A1 | 2/2019 | Chopra et al. | |
| 2019/0175573 A1 | 6/2019 | Carrancio et al. | |
| 2020/0163948 A1 | 5/2020 | Cathers et al. | |
| 2020/0206212 A1 | 7/2020 | Choudrie et al. | |
| 2021/0040064 A1 | 2/2021 | Fernandez et al. | |
| 2021/0069356 A1 | 3/2021 | Hansen et al. | |
| 2021/0154182 A1 | 5/2021 | Carrancio et al. | |

FOREIGN PATENT DOCUMENTS

| | | |
|---|---|---|
| WO | WO 2010/036959 | 4/2010 |
| WO | WO 2010/089411 | 8/2010 |
| WO | WO 2011/066342 | 6/2011 |
| WO | WO 2011/082400 | 7/2011 |
| WO | WO 2011/159877 | 12/2011 |
| WO | WO 2011/161699 | 12/2011 |
| WO | WO2017120415 * | 7/2017 |
| WO | WO 2019/003018 | 1/2019 |
| WO | WO 2021/188387 | 9/2021 |

OTHER PUBLICATIONS

Emens et al., "Chemotherapy: friend or foe to cancer vaccines ?." Current opinion in molecular therapeutics 3.1 (2001): 77-84.

Fourcade et al., "Upregulation of Tim-3 and PD-1 expression is associated with tumor antigen-specific CD8+ T cell dysfunction in melanoma patients." Journal of Experimental Medicine 207.10 (2010): 2175-2186.

Gaidt et al. "Human monocytes engage an alternative inflammasome pathway." Immunity 44.4 (2016): 833-846.

Gopalsamy et al, "Identification of pyrimidine derivatives as hSMG-1 inhibitors." Bioorganic & medicinal chemistry letters 22.21 (2012): 6636-6641.

Lee et al. "Current concepts in the diagnosis and management of cytokine release syndrome." Blood, The Journal of the American Society of Hematology 124.2 (2014): 188-195.

Ling et al., "Anakinra reduces blood pressure and renal fibrosis in one kidney/DOCA/salt-induced hypertension." Pharmacological research 116 (2017): 77-86.

Loo et al., "Development of an Fc-enhanced anti-B7-H3 monoclonal antibody with potent antitumor activity." Clinical cancer research 18.14 (2012): 3834-3845.

Lust et al., "Induction of a chronic disease state in patients with smoldering or indolent multiple myeloma by targeting interleukin 1β-induced interleukin 6 production and the myeloma proliferative component." Mayo Clinic Proceedings. vol. 84. No. 2. Elsevier, 2009.

Morrison et al., "Antibody-cytokine fusion proteins for the therapy of cancer." Journal of immunological methods 248.1-2 (2001): 91-101.

Netea et al. Blood. 2009, 113(10):2324-35.

Pardoll et al., "The blockade of immune checkpoints in cancer immunotherapy." Nature Reviews Cancer 12.4 (2012): 252-264.

Ravindran et al. "The amino acid sensor GCN2 controls gut inflammation by inhibiting inflammasome activation." Nature 531. 7595 (2016): 523-527.

Sakuishi et al. "Targeting Tim-3 and PD-1 pathways to reverse T cell exhaustion and restore anti-tumor immunity." Journal of Experimental Medicine 207.10 (2010): 2187-2194.

Schneider et al. "The inflammasome drives GSDMD-independent secondary pyroptosis and IL-1 release in the absence of caspase-1 protease activity." Cell reports 21.13 (2017): 3846-3859.

Shenderov et al. "Cutting edge: Endoplasmic reticulum stress licenses macrophages to produce mature IL-1β in response to TLR4 stimulation through a caspase-8- and TRIF-dependent pathway." The Journal of Immunology 192.5 (2014): 2029-2033.

Straathof et al., "An inducible caspase 9 safety switch for T-cell therapy." Blood 105.11 (2005): 4247-4254.

International Search Report issued for PCT/US2020/058789 dated Mar. 9, 2021.

Vanhala et al., "Proinflammation and Hypertension: A Population-Based Study" Mediators of Inflammation, 2008, 2008: pp. 1-7.

Ong et al., "Mechanisms of Dexamethasone-Induced Hypertension" Current Hypertension Reviews, 2009, 5 (1): 61-74.

Da Silva et al., "Inhibition by glucocorticoids of the interleukin-1b-enhanced expression of the mast cell growth fator SCF" British Journal of Pharmacology, 2002, 135(7), 1634-1640.

Supplementary European Search Report issued for EP 20886152. 6-112 dated Oct. 25, 2023.

* cited by examiner

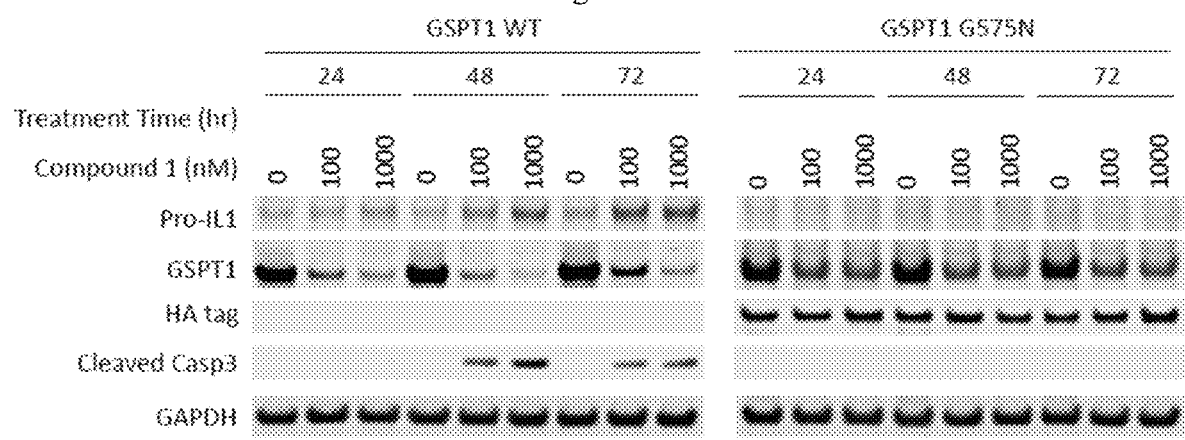

COMBINATION THERAPY WITH 2-(4-CHLOROPHENYL)-N-((2-(2,6-DIOXO-IPERIDIN-3-YL)-1-OXOISOINDOLIN-5-YL) METHYL)-2,2-DIFLUOROACETAMIDE

RELATED APPLICATIONS

This application claims the benefit of U.S. Provisional Application No. 62/931,040, filed Nov. 5, 2019, the disclosure of which is incorporated herein by reference in its entirety.

FIELD

Provided herein are methods of treating, preventing, managing, and/or ameliorating hypotension related to administration of 2-(4-chlorophenyl)-N-((2-(2,6-dioxopiperidin-3-yl)-1-oxoisoindolin-5-yl)methyl)-2,2-difluoroacetamide or a stereoisomer or a mixture of stereoisomers, pharmaceutically acceptable salt, tautomer, prodrug, solvate, hydrate, co-crystal, clathrate, or polymorph thereof in a cancer patient, wherein the methods comprise administering a therapeutically effective amount of 2-(4-chlorophenyl)-N-((2-(2,6-dioxopiperidin-3-yl)-1-oxoisoindolin-5-yl)methyl)-2,2-difluoroacetamide or a stereoisomer or a mixture of stereoisomers, pharmaceutically acceptable salt, tautomer, prodrug, solvate, hydrate, co-crystal, clathrate, or polymorph thereof and a therapeutically effective amount of a glucocorticoid receptor agonist, an interleukin-1 receptor antagonist, or an interleukin-1β blocker. Also disclosed herein is 2-(4-chlorophenyl)-N-((2-(2,6-dioxopiperidin-3-yl)-1-oxoisoindolin-5-yl)methyl)-2,2-difluoroacetamide for use in such methods.

BACKGROUND 2-(4-Chlorophenyl)-N-((2-(2,6-dioxopiperidin-3-yl)-1-oxoisoindolin-5-yl)methyl)-2,2-difluoroacetamide or a stereoisomer or mixture of stereoisomers, pharmaceutically acceptable salt, tautomer, prodrug, solvate, hydrate, co-crystal, clathrate, or polymorph thereof has been shown to have anti-cancer activities. The compound, methods of use thereof and pharmaceutical compositions comprising the same are disclosed in U.S. Pat. Nos. 9,499,514; 9,808,451; 9,968,596; 10,189,808; 10,449,187; 10,052,315; and 10,245,258; and U.S. Publication Nos. US 2018/0221361 A1; US 2019/0106405 A1; US 2019/0175573 A1; and US 2019/003018 A1.

There is a continuing to need for efficient methods of using 2-(4-chlorophenyl)-N-((2-(2,6-dioxopiperidin-3-yl)-1-oxoisoindolin-5-yl)methyl)-2,2-difluoroacetamide or a stereoisomer or mixture of stereoisomers, pharmaceutically acceptable salt, tautomer, prodrug, solvate, hydrate, co-crystal, clathrate, or polymorph thereof in treating cancer.

BRIEF SUMMARY

In one embodiment, provided herein are methods of treating, preventing, managing, and/or ameliorating hypotension related to administration of 2-(4-chlorophenyl)-N-((2-(2,6-dioxopiperidin-3-yl)-1-oxoisoindolin-5-yl)methyl)-2,2-difluoroacetamide or a stereoisomer or a mixture of stereoisomers, pharmaceutically acceptable salt, tautomer, prodrug, solvate, hydrate, co-crystal, clathrate, or polymorph thereof (collectively Compound 1) in a cancer patient, wherein the methods comprise administering to the patient a therapeutically effective amount of Compound 1 and a therapeutically effective amount of a glucocorticoid receptor agonist, an interleukin-1 receptor antagonist, or an interleukin-1β blocker. In one embodiment, the glucocorticoid receptor agonist is prednisone, prednisolone, methylprednisolone, hydrocortisone, cortisol, triamcinolone, betamethasone, or dexamethasone. In one embodiment, the glucocorticoid receptor agonist is prednisone, prednisolone, methylprednisolone, hydrocortisone, cortisone, cortisol, triamcinolone, betamethasone, or dexamethasone. In one embodiment, the glucocorticoid receptor agonist is dexamethasone. In one embodiment, the IL-1 receptor antagonist is anakinra. In one embodiment, the IL-1β blocker is canakinumab. In one embodiment, the cancer is a hematological cancer. In one embodiment, the hematological cancer is leukemia. In one embodiment, the leukemia is acute myeloid leukemia (AML). In certain embodiments, the AML, is relapsed or refractory AML.

In one embodiment, provided herein are methods suppressing Compound 1 related interleukin-1β (IL-1β) induction in a cancer patient, wherein the methods comprise administering to the patient a therapeutically effective amount of Compound 1 and a therapeutically effective amount of a glucocorticoid receptor agonist, an IL-1β receptor antagonist or an IL-1β blocker. In one embodiment, the glucocorticoid receptor agonist is prednisone, prednisolone, methylprednisolone, hydrocortisone, cortisol, triamcinolone, betamethasone, or dexamethasone. In one embodiment, the glucocorticoid receptor agonist is prednisone, prednisolone, methylprednisolone, hydrocortisone, cortisone, cortisol, triamcinolone, betamethasone, or dexamethasone. In one embodiment, the glucocorticoid receptor agonist is dexamethasone. In one embodiment, the IL-1 receptor antagonist is anakinra. In one embodiment, the IL-1β blocker is canakinumab. In one embodiment, the cancer is a hematological cancer. In one embodiment, the hematological cancer is leukemia. In one embodiment, the leukemia is acute myeloid leukemia (AML). In certain embodiments, the AML is relapsed or refractory AML.

In one embodiment, the methods provided herein further comprise administering to the patient a therapeutically effective amount of a vasopressor. In one embodiment, the methods further comprise administering to the patient a single low-dose vasopressor. In one embodiment, the methods further comprise administering to the patient one or more high-dose vasopressors. Non-limiting examples of vasopressors include epinephrine, isoproterenol, phenylephrine, norepinephrine, dobutamine, ephedrine, droxidopa, dopamine, and others known in the art.

In certain embodiments, the methods provided herein further comprise administering to the patient an additional agent selected from JAK inhibitors, FLT3 inhibitors, mTOR inhibitors, spliceosome inhibitors, BET inhibitors, SMG1 inhibitors, ERK inhibitors, LSD1 inhibitors, BH3 mimetics, topoisomerase inhibitors, and RTK inhibitors.

Compound 1 and pharmaceutical compositions comprising the same used in the methods herein are described in U.S. Pat. Nos. 9,499,514; 9,808,451; 9,968,596; 10,189,808; 10,449,187; 10,052,315; and 10,245,258; and U.S. Publication Nos. US 2018/0221361 A1; US 2019/0106405 A1; US 2019/0175573 A1; and US 2019/003018 A1, the disclosures of each which are incorporated herein by reference in their entireties.

In certain embodiments, provided herein are pharmaceutical compositions, single unit dosage forms, and kits comprising Compound 1 and a glucocorticoid receptor agonist, an interleukin-1 receptor antagonist, or an interleukin-1β blocker, suitable for use in treating, preventing, ameliorating and/or managing hypotension. In certain embodiments, provided herein are pharmaceutical compositions, single unit dosage forms, and kits comprising Compound 1 and a glucocorticoid suitable for use in the methods suppressing Compound 1 related interleukin-1β (IL-1β) induction. In one embodiment, the glucocorticoid receptor agonist is prednisone, prednisolone, methylprednisolone, hydrocortisone, cortisol, triamcinolone, betamethasone, or dexamethasone. In one embodiment, the glucocorticoid receptor agonist is prednisone, prednisolone, methylprednisolone, hydrocortisone, cortisone, cortisol, triamcinolone, betamethasone, or dexamethasone. In one embodiment, the glucocorticoid receptor agonist is dexamethasone. In certain embodiments, such compositions include Compound 1 and dexamethasone optionally in combination with one or more additional therapeutic agents. In other embodiments, IL-1 receptor antagonist is anakinra. In certain embodiments, such compositions include Compound 1 and anakinra, optionally in combination with one or more additional therapeutic agents. In one embodiment, the IL-1β blocker is canakinumab. In certain embodiments, such compositions include Compound 1 and canakinumab, optionally in combination with one or more additional therapeutic agents.

Also provided herein is 2-(4-chlorophenyl)-N-((2-(2,6-dioxopiperidin-3-yl)-1-oxoisoindolin-5-yl)methyl)-2,2-difluoroacetamide, or a stereoisomer or mixture of stereoisomers, pharmaceutically acceptable salt, tautomer, prodrug, solvate, hydrate, co-crystal, clathrate, or polymorph thereof (Compound 1) for use in a method of treating, preventing, managing, and/or ameliorating hypotension in a cancer patient, wherein the method comprises administering to the patient a therapeutically effective amount of Compound 1 and a therapeutically effective amount of a glucocorticoid receptor agonist, an interleukin-1 receptor antagonist, or an interleukin-1β blocker.

Also provided herein is 2-(4-chlorophenyl)-N-((2-(2,6-dioxopiperidin-3-yl)-1-oxoisoindolin-5-yl)methyl)-2,2-difluoroacetamide, or a stereoisomer or mixture of stereoisomers, pharmaceutically acceptable salt, tautomer, prodrug, solvate, hydrate, co-crystal, clathrate, or polymorph thereof (Compound 1) for use in a method of suppressing interleukin-1β induction in a cancer patient, wherein the method comprises administering to the patient a therapeutically effective amount of Compound 1 and a therapeutically effective amount of a glucocorticoid receptor agonist, an interleukin-1 receptor antagonist, or an interleukin-1β blocker.

These and other aspects of the subject matter described herein will become evident upon reference to the following detailed description.

BRIEF DESCRIPTION OF THE DRAWINGS

FIG. 1A illustrates the effect of Compound 1 or lipopolysaccharide (LPS) treatment on target proteins in ML-2 cells: GSPT1, IL-1β, and cleaved caspase 3 in ML-2 cells after treatment with Compound 1 or 1.0 μg/mL LPS for 6, 24, and 48 hours are shown. FIG. 1B illustrates the levels of IL-1 β, IL-1 β, IL-1RA and IL-18 (pg/mL) in Compound 1 treated ML-2 cell culture supernatant as measured by an electrochemiluminescence assay. FIG. 1C shows secreted IL-1 β, in bone marrow mononuclear cells from 9 AML subjects and 2 normal donors after treatment with Compound 1 for 24 and 48 hours as measured by an electrochemiluminescence assay. Grey color indicates subjects classified as M0/M1/M2 by FAB status. Black circle indicates subjects classified as M4/M5. Open circle indicates normal donor.

FIG. 2A shows IL-1β levels measured by an electrochemiluminescence assay, in ML-2 cells treated with a combination of 1000 nM Compound 1 and 1, 10, 100 μM pan-caspase (Z-VAD-FMK), caspase 8 (Z-VAD-FMK) or caspase 1 inhibitors (Z-VAD-IETD or Z-YVAD). FIG. 2B provides levels of GSPT1, pro-IL-1β, caspase 1, cleaved caspase 8 and cleaved caspase 3 in an immunoblot assay, in CRISPR/Cas9 knock out of caspase 1 or caspase 8 in ML-2 cells upon treatment with vehicle or 1 μM Compound 1 (at 48 hours post-treatment). FIG. 2C provides IL-1β levels in CRISPR/Cas9 knock out of caspase 1 or caspase 8 in ML-2 cell culture supernatant measured by an electrochemiluminescence assay, at 72 hours post-treatment. FIG. 2D demonstrates secreted IL-1β levels at 72 hours in ML-2 cells treated with test compounds at 1 μM with similar, yet different, mechanisms to Compound 1. Caspase 8 activation levels were quantified by a caspase 8/FLICE activity colorimetric assay and presented as normalized value compared to DMSO treatment group. Relationship between secreted IL-1 β levels and the extent of caspase 8 activation levels were visualized by a dot plot.

FIG. 3A shows IL-1 β levels measured by an electrochemiluminescence assay, in MV411 cells treated with a combination of 1000 nM Compound 1 and 10 μM pan-caspase (Z-VAD-FMK), caspase 8 (Z-VAD-FMK) or caspase 1 inhibitors (Z-VAD-IETD or Z-YVAD). FIG. 3B provides secreted IL-1β levels determined at 72 hours by an electrochemiluminescence assay; caspase 8 activation levels quantified by a caspase 8/FLICE activity colorimetric assay and presented as normalized value compared to DMSO treatment group, in MV4-11 cells treated with a panel of compounds at 1 μM with similar, yet different, mechanisms to Compound 1. FIG. 3C demonstrates time course of caspase 8 activation levels in ML-2 cells treated with a panel of mechanistic compounds at 1 βM. FIG. 3D demonstrates time course of caspase 8 activation levels in MV4-11 cells treated with a panel of mechanistic compounds at 1 μM.

FIG. 4A demonstrates the effect test compounds on cells harvested at 24, 48 and 72 hours post-compound treatment for immunoblot analysis on full length pro-IL-13 and GSPT1 levels. FIG. 4B shows IL-1β levels in cell culture supernatant at 24, 48 and 72 hours post-compound treatment as measured by an electrochemiluminescence assay. FIG. 4C provides a correlation plot of caspase 3/7 activation level versus IL-1β induction.

FIG. 6A illustrates the rate and depth of apoptosis measured by the extent of caspase 3/7 activation every 4 hours post-compound treatment over a 68 hour period using the IncuCyte Zoom imaging system. FIG. 6B provides cell viability measured 3 days post-compound treatment by a CellTitre-Glo assay.

FIGS. 8A-8D demonstrate the effect of GSPT1 degradation on IL-1β induction by Compound 1 in an isogenic MOLM13 cell pair expressing endogenous GSPT1 or overexpressing a non-degradable form of GSPT1 G575N. FIG. 8A illustrates the levels of pro-IL-1β, GSPT1, HA tag, cleaved caspase 3 and GAPDH in cells harvested for immunoblot analysis. FIG. 8B demonstrates the single agent dose response to Compound 1 measured 3 days post-treatment by a CellTiter-Glo viability assay. Error bars are standard deviation from duplicate assay plates. FIG. 8C shows intracellular IL-1β levels measured by an electrochemiluminescence assay. FIG. 8D shows secreted (D) IL-1β levels measured by an electrochemiluminescence assay.

FIG. 9A illustrates various biomarkers in cells harvested for immunoblot analysis. FIG. 9B illustrates IL-1β levels in cell lysates measured by an electrochemiluminescence assay. FIG. 9C illustrates IL-1β levels in supernatant measured by an electrochemiluminescence assay.

FIG. 10A shows IL-1β levels in ML-2, MV4-11, MOLM13 and KG1 cells upon treatment with a titration of Compound 1 (0, 100, 1000 nM) in combination with dexamethasone (0, 100, 1000 nM) for 48 hours, measured by an electrochemiluminescence assay in cell culture supernatant. FIG. 10B shows cleaved caspase 3/7 levels every 6 hours over a 72 hour period in ML-2 cells treated with 333 nM of Compound 1 in combination with 0, 12, 111, 1000 nM dexamethasone, measured by an IncuCyte assay. Triangle, closed circle, grey square, and open circle represent 0, 12, 111, 1000 nM dexamethasone respectively. FIG. 10C shows cell viability measured by a CellTiter-Glo assay for ML-2 cells treated with 0-1 μM Compound 1 in combination with a titration of dexamethasone (0-1 μM) for 72 hours. Error bars are standard deviation from duplicate assay plates.

DETAILED DESCRIPTION

Definitions

Figure 1A:
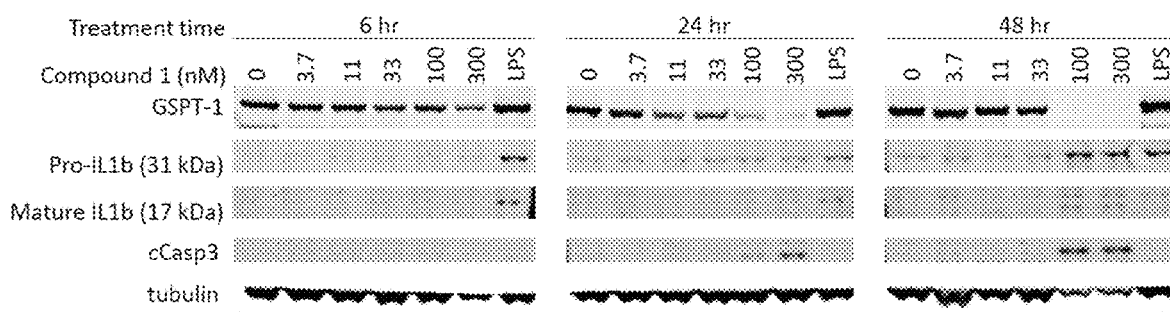
FIGS. 1A-1C demonstrate IL-1 modulation by Compound 1 in AML cell lines in vitro and primary AML bone marrow mononuclear cells ex vivo.
Figure 1:
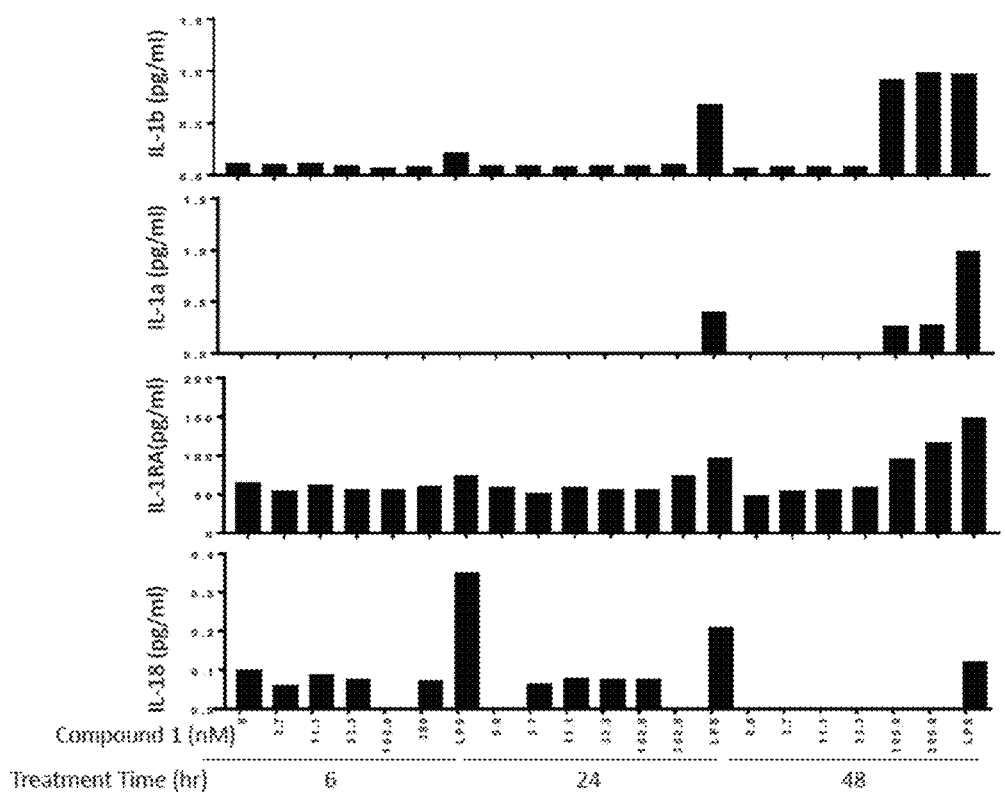

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs. In general, the technical teaching of one embodiment can be combined with that disclosed in other embodiments provided herein.

The use of the word "a" or "an" when used in conjunction with the term "comprising" in the claims and/or the specification can mean "one", but it is also consistent with the meaning of "one or more", "at least one" and "one or more than one."

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the terms "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive. E.g., "treating, preventing or managing" or similar listings means: "treating; preventing; managing; treating and preventing; treating and managing; preventing and managing; treating, preventing and managing".

The term "Compound 1" refers to "2-(4-chlorophenyl)-N-((2-(2,6-dioxopiperidin-3-yl)-1-oxoisoindolin-5-yl)methyl)-2,2-difluoroacetamide" having the structure:

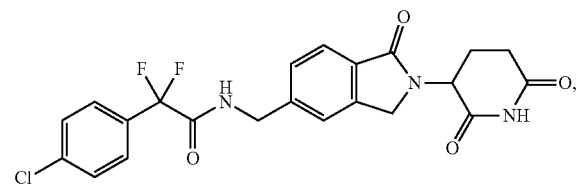 [SMILES: O=C1CCC(N2Cc3cc(CNC(=O)C(F)(F)c4ccc(Cl)cc4)ccc3C2=O)C(=O)N1]

and its stereoisomers or mixture of stereoisomers, pharmaceutically acceptable salts, tautomers, prodrugs, solvates, hydrates, co-crystals, clathrates, or polymorphs thereof. In certain embodiments, Compound 1 refers to 2-(4-chlorophenyl)-N-((2-(2,6-dioxopiperidin-3-yl)-1-oxoisoindolin-5-yl)methyl)-2,2-difluoroacetamide and its tautomers. In certain embodiments, Compound 1 refers to a polymorph of 2-(4-chlorophenyl)-N-((2-(2,6-dioxopiperidin-3-yl)-1-oxoisoindolin-5-yl)methyl)-2,2-difluoroacetamide, such as Form A, B, C, D, or E, or a mixture thereof. In certain embodiments, Compound 1 refers to polymorph Form C of 2-(4-chlorophenyl)-N-((2-(2,6-dioxopiperidin-3-yl)-1-oxoisoindolin-5-yl)methyl)-2,2-difluoroacetamide. In certain embodiments, Compound 1 refers to an amorphous form of 2-(4-chlorophenyl)-N-((2-(2,6-dioxopiperidin-3-yl)-1-oxoisoindolin-5-yl)methyl)-2,2-difluoroacetamide. In one embodiment, the stereoisomer is an enantiomer.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11:942-944).

As used herein, and unless otherwise specified, the term "parenteral" includes subcutaneous, intravenous, intramuscular, intra-artricular, intra-synovial, intrasternal, intrathecal, intrahepatic, intralesional and intracranial injection or infusion techniques.

As used herein, and unless otherwise specified, the expression "unit dose" refers to a physically discrete unit of a formulation appropriate for a subject to be treated (e.g., for a single dose); each unit containing a predetermined quantity of an active agent selected to produce a desired therapeutic effect (it being understood that multiple doses may be required to achieve a desired or optimum effect), optionally together with a pharmaceutically acceptable carrier, which may be provided in a predetermined amount. The unit dose may be, for example, a volume of liquid (e.g. an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may contain a variety of components in addition to the therapeutic agent(s). For example, acceptable carriers (e.g., pharmaceutically acceptable carriers), diluents, stabilizers, buffers, preservatives, etc., may be included as described infra. It will be understood, however, that the total daily usage of a formulation of the present disclosure will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

As used herein, the term "solid form" refers a crystal form or an amorphous form or a mixture thereof of 2-(4-chlorophenyl)-N-((2-(2,6-dioxopiperidin-3-yl)-1-oxoisoindolin-5-yl)methyl)-2,2-difluoroacetamide or a stereoisomer or mixture of stereoisomers, pharmaceutically acceptable salt, tautomer, prodrug, solvate, hydrate, co-crystal, clathrate, or polymorph thereof.

As used herein, unless otherwise specified, the term "pharmaceutically acceptable salt(s)," as used herein includes, but is not limited to, salts of acidic or basic moieties of Compound 1. Basic moieties are capable of forming a wide variety of salts with various inorganic and organic acids. The acids that can be used to prepare pharmaceutically acceptable acid addition salts of such basic compounds are those that form non-toxic acid addition salts, e.g., salts containing pharmacologically acceptable anions. Suitable organic acids include, but are not limited to, maleic, fumaric, benzoic, ascorbic, succinic, acetic, formic, oxalic, propionic, tartaric, salicylic, citric, gluconic, lactic, mandelic, cinnamic, oleic, tannic, aspartic, stearic, palmitic, glycolic, glutamic, gluconic, glucaronic, saccharic, isonicotinic, methanesulfonic, ethanesulfonic, p-toluenesulfonic, benzenesulfonic acids, or pamoic (e.g., 1,1'-methylene-bis-(2-hydroxy-3-naphthoate) acids. Suitable inorganic acids include, but are not limited to, hydrochloric, hydrobromic, hydroiodic, sulfuric, phosphoric, or nitric acids. Compounds that include an amine moiety can form pharmaceutically acceptable salts with various amino acids, in addition to the acids mentioned above. Chemical moieties that are acidic in nature are capable of forming base salts with various pharmacologically acceptable cations. Examples of such salts are alkali metal or alkaline earth metal salts and, particularly, calcium, magnesium, sodium, lithium, zinc, potassium, or iron salts.

As used herein, and unless otherwise specified, the term "solvate" means a compound provided herein or a salt thereof that further includes a stoichiometric or non-stoichiometric amount of solvent bound by non-covalent intermolecular forces. Where the solvent is water, the solvate is a hydrate.

As used herein and unless otherwise indicated, the term "prodrug" means a derivative of a compound that can hydrolyze, oxidize, or otherwise react under biological conditions (in-vitro or in-vivo) to provide the compound. Examples of prodrugs include, but are not limited to, derivatives of compounds described herein (e.g., Compound 1) that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues.

A "pharmaceutically acceptable excipient," refers to a substance that aids the administration of an active agent to a subject by for example modifying the stability of an active agent or modifying the absorption by a subject upon administration. A pharmaceutically acceptable excipient typically has no significant adverse toxicological effect on the patient. Examples of pharmaceutically acceptable excipients include, for example, water, NaCl (including salt solutions), normal saline solutions, ½ normal saline, sucrose, glucose, bulking agents, buffers, binders, fillers, disintegrants, lubricants, coatings, sweeteners, flavors, alcohols, oils, gelatins, carbohydrates such as amylose or starch, fatty acid esters, hydroxymethycellulose, polyvinyl pyrrolidine, and colors, and the like. One of skill in the art will recognize that other pharmaceutical excipients known in the art are useful in the present invention and include those listed in for example the *Handbook of Pharmaceutical Excipients*, Rowe R. C., Shesky P. J., and Quinn M. E., 6$^{th}$ Ed., The Pharmaceutical Press, RPS Publishing (2009). The terms "bulking agent", and "buffer" are used in accordance with the plain and ordinary meaning within the art.

As used herein, and unless otherwise specified, the term "about," when used in connection with doses, amounts, or weight percent of ingredients of a composition or a dosage form, means dose, amount, or weight percent that is recognized by those of ordinary skill in the art to provide a pharmacological effect equivalent to that obtained from the specified dose, amount, or weight percent is encompassed. Specifically, the term "about" contemplates a dose, amount, or weight percent within 30%, 25%, 20%, 15%, 10%, or 5% of the specified dose, amount, or weight percent is encompassed.

As used herein, "administer" or "administration" refers to the act of physically delivering a substance as it exists outside the body into a subject. Administration includes all forms known in the art for delivering therapeutic agents, including but not limited to topical, mucosal, injections, intradermal, intravenous, intramuscular delivery or other method of physical delivery described herein or known in the art (e.g., implantation of a slow-release device, such as a mini-osmotic pump to a subject; liposomal formulations;

buccal; sublingual; palatal; gingival; nasal; vaginal; rectal; intra-arteriole; intraperitoneal; intraventricular; intracranial; or transdermal).

"Anti-cancer agents" refer to anti-metabolites (e.g., 5-fluoro-uracil, methotrexate, fludarabine), antimicrotubule agents (e.g., vinca alkaloids such as vincristine, vinblastine; taxanes such as paclitaxel, docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, JM-216 or satraplatin, CI-973), anthracyclines (e.g., doxorubicin, daunorubicin), antitumor antibiotics (e.g., mitomycin, idarubicin, adriamycin, daunomycin), topoisomerase inhibitors (e.g., etoposide, camptothecins), anti-angiogenesis agents (e.g. SUTENT®, sunitinib malate, and Bevacizumab) or any other cytotoxic agents (estramustine phosphate, prednimustine), hormones or hormone agonists, antagonists, partial agonists or partial antagonists, kinase inhibitors, checkpoint inhibitors, and radiation treatment.

By "co-administer" it is meant that compounds, compositions or agents described herein are administered at the same time, just prior to, or just after the administration of one or more additional compounds, compositions or agents, including for example an anti-cancer agent. Co-administration is meant to include simultaneous or sequential administration of compounds, compositions or agents individually or in combination (more than one compound or agent). Co-administration includes administering two compounds, compositions or agents simultaneously, approximately simultaneously (e.g., within about 1, 5, 10, 15, 20, or 30 minutes of each other), or sequentially in any order. Thus, co-administration can include administering one active agent (e.g. a compound described herein) within 0.5, 1, 2, 4, 6, 8, 10, 12, 16, 20, or 24 hours of an additional active agent. Co-administration can also be accomplished by co-formulation, e.g., preparing a single dosage form including both active agents. The active agents can be formulated separately. In such instances, the active agents are admixed and included together in the final form of the dosage unit. Alternatively, co-administration as described herein can include administering two separate unit dosage forms of at least two separate active agents (e.g., Compound 1 and an additional active agent described herein).

As used herein, the term "daily" is intended to mean that a therapeutic compound, such as Compound 1, is administered once or more than once each day for a period of time. The term "continuous" is intended to mean that a therapeutic compound, such as Compound 1, is administered daily for an uninterrupted period of at least 10 days to 52 weeks. The term "intermittent" or "intermittently" as used herein is intended to mean stopping and starting at either regular or irregular intervals. For example, intermittent administration of Compound 1 is administration for one to six days per week, administration in cycles (e.g., daily administration for one to ten consecutive days of a 28 day cycle, then a rest period with no administration for rest of the 28 day cycle or daily administration for two to eight consecutive weeks, then a rest period with no administration for up to one week), or administration on alternate days. The term "cycling" as used herein is intended to mean that a therapeutic compound, such as Compound 1, is administered daily or continuously but with a rest period.

A "cycling therapy" refers to a regimen or therapy that includes an administration period as described herein and a rest period as described herein.

The term "administration period" as used herein refers to a period of time a subject is continuously or actively administered a compound or composition described herein.

The term "rest period" as used herein refers to a period of time, often following an administration period, where a subject is not administered a compound or composition described herein (e.g. discontinuation of treatment). In certain embodiments, a "rest period" refers to a period of time where a single agent is not administered to a subject or treatment using a particular compound is discontinued. In such embodiments, an additional therapeutic agent (e.g., a different agent than the compound or composition administered in the previous administration period) can be administered to the subject.

An "effective amount" is an amount sufficient to achieve the effect for which it is administered (e.g., treat a disease or reduce one or more symptoms of a disease or condition). Thus, administration of an "amount" of a compound described herein to a subject refers to administration of "an amount effective," to achieve the desired therapeutic result. A "therapeutically effective amount" of a compound described herein for purposes herein is thus determined by such considerations as are known in the art. The term "therapeutically effective amount" of a compound herein refers to the amount of the compound that, when administered, is sufficient to treat one or more of the symptoms of a disease described herein. Administration of a compound described herein can be determined according to factors such as, for example, the disease state, age, sex, and weight of the individual. A therapeutically effective amount also refers to any toxic or detrimental effects of Compound 1 are outweighed by the therapeutically beneficial effects.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a patient with such a disease or disorder. In some embodiments, the terms refer to the administration of a compound provided herein, with or without other additional active agent, after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of diseases or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a patient derives from a prophylactic and/or therapeutic agent do not result in a cure of the disease or disorder. In this regard, the term "managing" encompasses treating a patient who had suffered from the particular disease in an attempt to prevent or minimize the recurrence of the disease, or lengthening the time during which the remains in remission.

As used herein, and unless otherwise specified, the terms "ameliorate," "ameliorating" and "amelioration" of the symptoms of a particular disorder by administration of a particular compound or compounds refer to any lessening, whether permanent or temporary, lasting or transient that can be attributed to or associated with administration of the compound or compounds, with or without other additional active compounds.

As used herein, "induction therapy" refers to the first treatment given for a disease, or the first treatment given with the intent of inducing complete remission in a disease, such as cancer. When used by itself, induction therapy is the one accepted as the best available treatment. For example, induction therapy for AML comprises treatment with cytarabine for 7 days plus treatment with an anthracycline, such as daunorubicin or idarubicin, for 3 days. If residual leukemia is detected, patients are treated with another chemotherapy course, termed reinduction. If the patient is in complete remission after induction therapy, then additional consolidation and/or maintenance therapy is given to prolong remission or to potentially cure the patient.

As used herein, "consolidation therapy" refers to the treatment given for a disease after remission is first achieved. For example, consolidation therapy for cancer is the treatment given after the cancer has disappeared after initial therapy. Consolidation therapy may include radiation therapy, stem cell transplant, or treatment with cancer drug therapy. Consolidation therapy is also referred to as intensification therapy and post-remission therapy.

As used herein, "maintenance therapy" refers to the treatment given for a disease after remission or best response is achieved, in order to prevent or delay relapse. Maintenance therapy can include chemotherapy, hormone therapy or targeted therapy.

The terms "subject," "patient," "subject in need thereof," and "patient in need thereof" are herein used interchangeably and refer to a living organism suffering from one or more of the diseases described herein that can be treated by administration of a composition described herein. Non-limiting examples of organisms include humans, other mammals, bovines, rats, mice, dogs, monkeys, goat, sheep, cows, deer, and other non-mammalian animals. In embodiments, a subject is human. A human subject can be between the ages of about 1 year old to about 100 years old. In embodiments, subjects herein can be characterized by the disease being treated (e.g., a "AML subject", a "cancer subject", or a "leukemia subject").

As used herein, the term "tumor," refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

As used herein, "hematological malignancy" or "hematological cancer" refers to cancer of the body's blood-forming and immune system—the bone marrow and lymphatic tissue. Such malignancies include leukemias, lymphomas (Non-Hodgkin's Lymphoma), Hodgkin's disease (also called Hodgkin's Lymphoma) and myeloma. In one embodiment, the myeloma is multiple myeloma. In some embodiments, the leukemia is, for example, acute myelogenous leukemia (AML), acute lymphocytic leukemia (ALL), adult T-cell leukemia, chronic lymphocytic leukemia (CLL), hairy cell leukemia, myelodysplasia, myeloproliferative disorders or myeloproliferative neoplasm (MPN), chronic myelogenous leukemia (CML), myelodysplastic syndrome (MDS), human lymphotropic virus-type 1 (HTLV 1) leukemia, mastocytosis, or B-cell acute lymphoblastic leukemia. In some embodiments, the lymphoma is, for example, diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, peripheral T-cell lymphoma (PTCL), cutaneous T-cell lymphoma (CTCL), mantle cell lymphoma (MCL), Hodgkin lymphoma (HL), non-Hodgkin lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter's transformation, nodal marginal zone lymphoma, or ALK-positive large B-cell lymphoma. In one embodiment, the hematological malignancy is indolent lymphoma including, for example, DLBCL, follicular lymphoma, or marginal zone lymphoma. In one embodiment, the hematological malignancy is ANIL. In another embodiment, the hematological malignancy is MDS.

The term "leukemia" refers to malignant neoplasms of the blood-forming tissues. The leukemia includes, but is not limited to, chronic lymphocytic leukemia, chronic myelocytic leukemia, acute lymphoblastic leukemia, acute myeloid leukemia, and acute myeloblastic leukemia. The leukemia can be relapsed, refractory or resistant to at least one anti-cancer therapy.

In one embodiment, the subject has acute myelogenous or myeloid leukemia (AML), including, for example, the following subtypes of AML. The term "acute myelogenous or myeloid leukemia" refers to hematological conditions characterized by proliferation and accumulation of primarily undifferentiated or minimally differentiated myeloid cells in the bone marrow, and includes subtypes categorized by either the FAB (French, American, British) or WHO classification system. As described herein, the AML includes the following subtypes based on the FAB classification: M0 (AML minimally differentiated); M1 (AML with minimal maturation); M2 (AML with maturation); M3 (Acute promyelocytic leukemia); M4 (Acute myelomonocytic leukemia); M4 (eos Acute myelomonocytic leukemia with eosinophilia); M5 (Acute monocytic leukemia); M6 (Acute erythroid leukemia); and M7 (Acute megakaryoblastic leukemia). As described herein, the AML includes the following subtypes based on the WHO classification: AML with recurrent genetic abnormalities (AML with translocation between chromosomes 8 and 21); AML with translocation or inversion in chromosome 16; AML with translocation between chromosomes 9 and 11; APL (M3) with translocation between chromosomes 15 and 17; AML with translocation between chromosomes 6 and 9; AML with translocation or inversion in chromosome 3); AML (megakaryoblastic) with a translocation between chromosomes 1 and 22; AML with myelodysplasia-related changes; AML related to previous chemotherapy or radiation (Alkylating agent-related AML; Topoisomerase II inhibitor-related AML); AML not otherwise categorized (AML that does not fall into the above categories, i.e. AML minimally differentiated (M0); AML with minimal maturation (M1); AML with maturation (M2); Acute myelomonocytic leukemia (M4); Acute monocytic leukemia (M5); Acute erythroid leukemia (M6); Acute megakaryoblastic leukemia (M7); Acute basophilic leukemia; Acute panmyelosis with fibrosis); Myeloid Sarcoma (also known as granulocytic sarcoma, chloroma or extramedullary myeloblastoma); and Undifferentiated and biphenotypic acute leukemias (also known as mixed phenotype acute leukemias). (see https://www.cancer.org/cancer/acute-myelo id-leukemia/detection-diagnosis-staging/how-classified.html, last accessed May 25, 2017).

In one embodiment, the subject has myelodysplastic syndrome (MDS), including, for example, the following subtypes of MDS. The term "myelodysplastic syndrome" refers to hematological conditions characterized by abnormalities in the production of one or more of the cellular components of blood (red cells, white cells (other than lymphocytes) and platelets (or their progenitor cells, megakaryocytes)). The ineffective hematopoiesis in the bone marrow (BM) and peripheral blood cytopenias in MDS manifest clinically as anemia, neutropenia, and/or thrombocytopenia of variable frequency and severity. Anemia is the most frequent laboratory finding and it often progresses to red blood cell (RBC) transfusion dependence. Other less common presenting clinical features related to the cytopenias are an increased risk of infection and/or hemorrhage and a propensity to progress to acute myeloid leukemia (AML) (Catenacci, et al. *Blood Rev* 2005; 19:301-319).

MDS includes the following disorders: refractory anemia (RA); RA with ringed sideroblasts (RARS); RA with excess of blasts (RAEB); refractory cytopenia with multilineage dysplasia (RCMD), refractory cytopenia with unilineage dysplasia (RCUD); unclassifiable myelodysplastic syndrome (MDS-U), myelodysplastic syndrome associated with an isolated del(5q) chromosome abnormality, therapy-related myeloid neoplasms and chronic myelomonocytic leukemia (CMML). The MDS as used herein also includes very low risk, low risk, intermediate risk, high risk and very high risk MDS. In some embodiments, the MDS is primary or de novo MDS. In other embodiments, the MDS is secondary.

As used herein, "promyelocytic leukemia" or "acute promyelocytic leukemia" refers to a malignancy of the bone marrow in which there is a deficiency of mature blood cells in the myeloid line of cells and an excess of immature cells called promyelocytes. It is usually marked by an exchange of regions of chromosomes 15 and 17.

As used herein, "acute lymphocytic leukemia (ALL)", also known as "acute lymphoblastic leukemia" refers to a malignant disease caused by the abnormal growth and development of early nongranular white blood cells, or lymphocytes.

As used herein, "T-cell leukemia" refers to a disease in which certain cells of the lymphoid system called T lymphocytes or T cells are malignant. T cells are white blood cells that normally can attack virus-infected cells, foreign cells, and cancer cells and produce substances that regulate the immune response.

The term "relapsed" refers to a situation where patients who have had a remission of leukemia after therapy have a return of leukemia cells in the marrow and a decrease in normal blood cells.

The term "refractory or resistant" refers to a circumstance where patients, even after intensive treatment, have residual leukemia cells in their marrow.

As used herein, the term "hypotension" refers to abnormally low blood pressure. As appreciated by those of skill in the art, blood pressure characterized as "hypotensive" may vary from individual to individual. Hypotension, however, is generally defined as systolic pressure less than 90 mmHg and/or diastolic pressure less than 50 mmHg. In certain embodiments, hypotension is graded as described in Table I (Lee et al. *Blood* 2014; 124(2): 188-195:

TABLE I

Grading for hypotension

Systolic blood pressure <90 mm Hg

| | Grade 1 | Grade 2 | Grade 3 | Grade 4 |
|---|---|---|---|---|
| Study Specific Grading | Asymptomatic, intervention not indicated | Responds to intravenous (IV) fluids and/or anticytokine therapy (eg, anakinra, steroids) | Needs IV vasopressor(s) | Life-threatening |

The term "drug resistance" refers to the condition when a disease does not respond to the treatment of a certain drug or drugs. Drug resistance can be either intrinsic, which means the disease has never been responsive to the particular drug or drugs, or it can be acquired, which means the disease ceases responding to particular a drug or drugs that the disease had previously responded to. In certain embodiments, drug resistance is intrinsic. In certain embodiments, the drug resistance is acquired.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

In the following, embodiments are provided herein that include all possible combinations of the particular embodiments set forth herein.

Compound 1

The compound suitable for use in the methods and formulations provided herein is Compound 1: 2-(4-chlorophenyl)-N-((2-(2,6-dioxopiperidin-3-yl)-1-oxoisoindolin-5-yl)methyl)-2,2-difluoroacetamide having the structure:

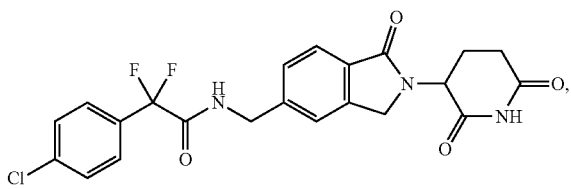 [SMILES: O=C1CCC(N2Cc3cc(CNC(=O)C(F)(F)c4ccc(Cl)cc4)ccc3C2=O)C(=O)N1]

or its stereoisomers or mixture of stereoisomers, isotopologues, pharmaceutically acceptable salts, tautomers, solvates, hydrates, co-crystals, clathrates, or polymorphs thereof. In certain embodiments, Compound 1 refers to 2-(4-chlorophenyl)-N-((2-(2,6-dioxopiperidin-3-yl)-1-oxoisoindolin-5-yl)methyl)-2,2-difluoroacetamide.

Compound 1 can be prepared according to the methods described in the Examples provided herein or as described in U.S. Pat. No. 9,499,514, the disclosure of which is incorporated herein by reference in its entirety. The compound can also be synthesized according to other methods apparent to those of skill in the art based upon the teaching herein.

In certain embodiments, Compound 1 is a solid. In certain embodiments, Compound 1 is a hydrate. In certain embodiments, Compound 1 is solvated. In certain embodiments, Compound 1 is anhydrous.

In certain embodiments, Compound 1 is amorphous. In certain embodiments, Compound 1 is crystalline. In certain embodiments, Compound 1 is in a crystalline form described in U.S. Publication No. 2017-0197934 filed on Jan. 6, 2017, which is incorporated herein by reference in its entirety. Exemplary solid forms are described on page nos. 86-101.

The solid forms of Compound 1 can be prepared according to the methods described in the disclosure of U.S. Publication No. 2017-0197934 filed on Jan. 6, 2017. See page nos. 86-101. The solid forms can also be prepared according to other methods apparent to those of skill in the art.

In one embodiment, Compound 1 is polymorph Form A, Form B, Form C, Form D, Form E or an amorphous form of 2-(4-chlorophenyl)-N-((2-(2,6-dioxopiperidin-3-yl)-1-oxoisoindolin-5-yl)methyl)-2,2-difluoroacetamide. Polymorphs of 2-(4-chlorophenyl)-N-((2-(2,6-dioxopiperidin-3-yl)-1-oxoisoindolin-5-yl)methyl)-2,2-difluoroacetamide are briefly described herein.

Glucocorticoid Receptor Agonists

In certain embodiments of the methods provided herein, a glucocorticoid receptor agonist is administered according to the dosages and dosing schedules known in the art, for example, as reported in the package insert for the respective glucocorticoid. The frequency and/or the dose of a glucocorticoid receptor agonist administration may be modified based on evaluation of the patient. In one embodiment, the glucocorticoid receptor agonist is prednisone, prednisolone, methylprednisolone, hydrocortisone, cortisol, triamcinolone, betamethasone, or dexamethasone. In one embodiment, the glucocorticoid receptor agonist is prednisone, prednisolone, methylprednisolone, hydrocortisone, cortisone, cortisol, triamcinolone, betamethasone, or dexamethasone. In one embodiment, the glucocorticoid receptor agonist is dexamethasone.

In certain embodiments of the methods provided herein, dexamethasone is administered according to the dosages and dosing schedules known in the art, for example, as reported in the package insert for dexamethasone sodium phosphate. For example, see, package inserts for DEXAMETHASONE SODIUM PHOSPHATE-dexamethasone sodium phosphate injection, solution, Fresenius Kabi USA, LLC, and DECADRON® (DEXAMETHASONE TABLETS, USP), Merck & Co., Inc. The frequency and/or the dose of dexamethasone administration may be modified based on evaluation of the patient.

In certain embodiments, dexamethasone is administered in an amount from about 0.5 mg to about 20 mg per day as an intravenous, intramuscular, intraarticular, intralesional, or a soft tissue injection. In certain embodiments, dexamethasone is administered in an amount from about 0.5 mg to about 15 mg per day as an intravenous, intramuscular, intraarticular, intralesional, or a soft tissue injection. In certain embodiments, dexamethasone is administered in an amount from about 0.5 mg to about 10 mg per day as an intravenous, intramuscular, intraarticular, intralesional, or a soft tissue injection. In certain embodiments, dexamethasone is administered in an amount from about 0.5 mg to about 9 mg per day as an intravenous, intramuscular, intraarticular, intralesional, or a soft tissue injection. In certain embodiments, dexamethasone is administered in an amount of about 10 mg per day as an intravenous injection.

In certain embodiments, dexamethasone is administered intravenously in a dose of about 10 mg every 12 hours.

In certain embodiments, dexamethasone is administered perorally in a dose of about 0.75 to 20 mg per day. In certain embodiments, dexamethasone is administered perorally in a dose of about 0.75 to 15 mg per day. In certain embodiments, dexamethasone is administered perorally in a dose of about 0.75 to 10 mg per day. In certain embodiments, dexamethasone is administered perorally in a dose of about 0.75 to 9 mg per day. In certain embodiments, dexamethasone is administered perorally in a dose of about 10 mg per day.

In certain embodiments, dexamethasone is administered as an oral tablet in a dose of about 0.75 to 20 mg per day. In certain embodiments, dexamethasone is administered as an oral tablet in a dose of about 0.75 to 15 mg per day. In certain embodiments, dexamethasone is administered as an oral tablet in a dose of about 0.75 to 10 mg per day. In certain embodiments, dexamethasone is administered as an oral tablet in a dose of about 0.75 to 9 mg per day. In certain embodiments, dexamethasone is administered as an oral tablet in a dose of about 10 mg per day.

In certain embodiments of the methods provided herein, prednisolone is administered according to the dosages and dosing schedules known in the art, for example, as reported in the package insert for prednisolone. The frequency and/or the dose of prednisolone administration may be modified based on evaluation of the patient. In certain embodiments, prednisolone is administered orally as a tablet or an oral solution. In certain embodiments, prednisolone is administered as an oral tablet in an amount from about 10 to 60 mg per day. In certain embodiments, prednisolone is administered as an oral solution in an amount from about 5 to 60 mg per day.

In certain embodiments of the methods provided herein, prednisone is administered according to the dosages and dosing schedules known in the art, for example, as reported in the package insert for prednisone. The frequency and/or the dose of prednisone administration may be modified based on evaluation of the patient. In certain embodiments, prednisone is administered orally as a tablet or an oral solution. In certain embodiments, prednisone is administered as a tablet or an oral solution in an amount from about 5 to 60 mg per day.

In certain embodiments of the methods provided herein, methylprednisolone is administered according to the dosages and dosing schedules known in the art, for example, as reported in the package insert for methylprednisolone. The frequency and/or the dose of methylprednisolone administration may be modified based on evaluation of the patient. In certain embodiments, methylprednisolone is administered by intravenous injection, by intravenous infusion, by intramuscular injection or orally. In certain embodiments, methylprednisolone is administered in an amount from about 5 to 50 mg or 10 to 40 mg. In certain embodiments, methylprednisolone is administered in an amount from about 5 to 50 mg per day or 10 to 40 mg per day.

In certain embodiments of the methods provided herein, hydrocortisone is administered according to the dosages and dosing schedules known in the art, for example, as reported in the package insert for hydrocortisone. For example, see, the package insert for SOLU-CORTEF®. The frequency and/or the dose of hydrocortisone administration may be modified based on evaluation of the patient. In certain embodiments, hydrocortisone is administered by intravenous injection, by intravenous infusion, by intramuscular injection or orally. In certain embodiments, hydrocortisone is administered in an amount from about 100 to 500 mg. In certain embodiments, the dose may be repeated at intervals of 2, 4, or 6 hours. In certain embodiments, hydrocortisone is administered in an amount from about 800 mg for a week followed by 320 mg every other day for one month.

In certain embodiments, the initial dose of hydrocortisone in pediatric patients is 0.56 to 8 mg/kg/day in three or four divided doses (20 to 240 mg/m$^2$bsa/day).

In certain embodiments of the methods provided herein, triamcinolone is administered according to the dosages and dosing schedules known in the art, for example, as reported in the package insert for triamcinolone. For example, see, the package insert for KENALOG®-40 INJECTION. The frequency and/or the dose of triamcinolone administration may be modified based on evaluation of the patient. In certain embodiments, triamcinolone is administered by intravenous injection or by intramuscular injection. In certain embodiments, triamcinolone is administered in an amount from about 2.5 to 100 mg. In certain embodiments, triamcinolone is administered in an amount of about 20 mg or less per day. In certain embodiments, triamcinolone is administered in an amount of about 40 mg to 80 mg per day. In certain embodiments, triamcinolone is administered in an amount of about 40 mg to 100 mg per day. In certain embodiments, triamcinolone is administered in an amount of about 60 mg mg per day.

In certain embodiments of the methods provided herein, betamethasone is administered according to the dosages and dosing schedules known in the art. For example, see, package inserts for CELESTONE® SOLUSPAN®. The frequency and/or the dose of betamethasone administration may be modified based on evaluation of the patient.

In certain embodiments, betamethasone is administered parenterally in an amount from about 0.25 mg to about 9.0 mg per day. In certain embodiments, betamethasone is administered as an intramuscular injection in an amount from about 0.25 mg to about 9.0 mg per day.

In certain embodiments, betamethasone is administered in daily doses of 30 mg of for a week followed by 12 mg every other day for 1 month.

In certain embodiments, betamethasone is administered in pediatric patients in an initial dose of 0.02 to 0.3 mg/kg/day administered in three or four divided doses (0.6 to 9 mg/m$^2$bsa/day).

IL-1 Receptor Antagonists

In certain embodiments of the methods provided herein, an IL-1β receptor antagonist is administered according to the dosages and dosing schedules known in the art, for example, as reported in the package insert for anakinra. The frequency and/or the dose of an IL-1β receptor antagonist administration may be modified based on evaluation of the patient. In one embodiment, the IL-1β receptor antagonist is anakinra, for example KINERET® (Amgen).

In certain embodiments of the methods provided herein, anakinra is administered according to the dosages and dosing schedules known in the art, for example, as reported in the package insert for anakinra. For example, see, package inserts for KINERET® (anakinra) injection, for subcutaneous use (Amgen). The frequency and/or the dose of anakinra administration may be modified based on evaluation of the patient.

In certain embodiments, anakinra is administered in an amount of about 100 mg per day as a subcutaneous injection. In some embodiments, anakinra is administered daily in an amount of about 100 mg as a subcutaneous injection. In other embodiments, anakinra is administered every other day in an amount of about 100 mg as a subcutaneous injection.

IL-1β Blockers

In certain embodiments of the methods provided herein, an IL-1β blocker is administered according to the dosages and dosing schedules known in the art, for example, as reported in the package insert for canakinumab. The frequency and/or the dose of an IL-1β blocker administration may be modified based on evaluation of the patient. In one embodiment, the IL-1β blocker is canakinumab, for example ILARIS® (Novartis).

In certain embodiments of the methods provided herein, canakinumab is administered according to the dosages and dosing schedules known in the art, for example, as reported in the package insert for canakinumab. For example, see, package inserts for ILARIS® (canakinumab) for injection, for subcutaneous use (Novartis). The frequency and/or the dose of canakinumab administration may be modified based on evaluation of the patient.

In certain embodiments, canakinumab is administered in an amount from about 150 mg to about 300 mg every 4 weeks as a subcutaneous injection. In some embodiments, canakinumab is administered in an amount from about 150 mg to about 300 mg every 8 weeks as a subcutaneous injection.

Methods

In one embodiment, provided herein are methods of treating, preventing, managing, and/or ameliorating hypotension related to Compound 1 in a cancer patient, wherein the methods comprise administering to the patient a therapeutically effective amount of Compound 1 and a therapeutically effective amount of a glucocorticoid receptor agonist, an interleukin-1 receptor antagonist, or an interleukin-1β blocker. In one embodiment, provided herein is Compound 1 for use in methods of treating, preventing, managing, and/or ameliorating hypotension related to Compound 1 in a cancer patient, wherein the methods comprise administering to the patient a therapeutically effective amount of Compound 1 and a therapeutically effective amount of a glucocorticoid receptor agonist, an interleukin-1 receptor antagonist, or an interleukin-1β blocker. In one embodiment, provided herein is Compound 1 for use in methods of treating hypotension related to Compound 1 in a cancer patient, wherein the methods comprise administering to the patient a therapeutically effective amount of Compound 1 and a therapeutically effective amount of a glucocorticoid receptor agonist, an interleukin-1 receptor antagonist, or an interleukin-1β blocker. In one embodiment, provided herein is Compound 1 for use in methods of preventing hypotension related to Compound 1 in a cancer patient, wherein the methods comprise administering to the patient a therapeutically effective amount of Compound 1 and a therapeutically effective amount of a glucocorticoid receptor agonist, an interleukin-1 receptor antagonist, or an interleukin-1β blocker. In one embodiment, provided herein is Compound 1 for use in methods of managing hypotension related to Compound 1 in a cancer patient, wherein the methods comprise administering to the patient a therapeutically effective amount of Compound 1 and a therapeutically effective amount of a glucocorticoid receptor agonist, an interleukin-1 receptor antagonist, or an interleukin-1β blocker. In one embodiment, provided herein is Compound I for use in methods of ameliorating hypotension related to Compound 1 in a cancer patient, wherein the methods comprise administering to the patient a therapeutically effective amount of Compound 1 and a therapeutically effective amount of a glucocorticoid receptor agonist, an interleukin-1 receptor antagonist, or an interleukin-1β blocker. In one embodiment, the glucocorticoid receptor agonist is prednisone, prednisolone, methylpredisolone, hydrocortisone, cortisol, triamcinolone, betamethasone, or dexamethasone. In one embodiment, the glucocorticoid receptor agonist is prednisone, prednisolone, methylprednisolone, hydrocortisone, cortisone, cortisol, triamcinolone, betamethasone, or dexamethasone. In one embodiment, the IL-1 receptor antagonist is anakinra. In one embodiment, the IL-1β blocker is canakinumab.

In one embodiment, provided herein are methods of treating, preventing, managing, and/or ameliorating hypotension related to Compound 1 in a cancer patient, wherein the methods comprise administering to the patient a therapeutically effective amount of Compound 1 and a therapeutically effective amount of dexamethasone. In one embodiment, provided herein is Compound 1 for use in methods of treating, preventing, managing, and/or ameliorating hypotension related to Compound 1 in a cancer patient, wherein the methods comprise administering to the patient a therapeutically effective amount of Compound 1 and a therapeutically effective amount of dexamethasone. In one embodiment, provided herein is Compound 1 for use in methods of treating hypotension related to Compound 1 in a cancer patient, wherein the methods comprise administering to the patient a therapeutically effective amount of Compound 1 and a therapeutically effective amount of dexamethasone. In one embodiment, provided herein is compound 1 for use in methods of preventing hypotension related to Compound 1 in a cancer patient, wherein the methods comprise administering to the patient a therapeutically effective amount of Compound 1 and a therapeutically effective amount of dexamethasone. In one embodiment, provided herein is Compound 1 for use in methods of managing hypotension related to Compound 1 in a cancer patient, wherein the methods comprise administering to the patient a therapeutically effective amount of Compound 1 and a therapeutically effective amount of dexamethasone. In one embodiment, provided herein is Compound 1 for use in methods of ameliorating hypotension related to Compound 1 in a cancer patient, wherein the methods comprise administering to the patient a therapeutically effective amount of Compound 1 and a therapeutically effective amount of dexamethasone. In one embodiment, provided herein are methods of treating, preventing, managing, and/or ameliorating hypotension related to Compound 1 in a cancer patient, wherein the methods comprise administering to the patient a therapeutically effective amount of Compound 1 and a therapeutically effective amount of prednisone, prednisolone, methylprednisolone, hydrocortisone, cortisol, triamcinolone, or betamethasone. In one embodiment, provided herein are methods of treating, preventing, managing, and/or ameliorating hypotension related to Compound 1 in a cancer patient, wherein the methods comprise administering to the patient a therapeutically effective amount of Compound 1 and a therapeutically effective amount of prednisone, prednisolone, methylprednisolone, hydrocortisone, cortisone, cortisol, triamcinolone, or betamethasone. In one embodiment, provided herein is Compound 1 for use in methods of treating, preventing, managing, and/or ameliorating hypotension related to Compound 1 in a cancer patient, wherein the methods comprise administering to the patient a therapeutically effective amount of Compound 1 and a therapeutically effective amount of prednisone, prednisolone, methylprednisolone, hydrocortisone, cortisol, triamcinolone, or betamethasone. In one embodiment, provided herein is Compound 1 for use in methods of treating, preventing, managing, and/or ameliorating hypotension related to Compound 1 in a cancer patient, wherein the methods comprise administering to the patient a therapeutically effective amount of Compound 1 and a therapeutically effective amount of prednisone, prednisolone, methylprednisolone, hydrocortisone, cortisone, cortisol, triamcinolone, or betamethasone. In one embodiment, provided herein is Compound I for use in methods of treating hypotension related to Compound 1 in a cancer patient, wherein the methods comprise administering to the patient a therapeutically effective amount of Compound 1 and a therapeutically effective amount of prednisone, prednisolone, methylprednisolone, hydrocortisone, cortisol, triamcinolone, or betamethasone. In one embodiment, provided herein is Compound I for use in methods of treating hypotension related to Compound 1 in a cancer patient, wherein the methods comprise administering to the patient a therapeutically effective amount of Compound 1 and a therapeutically effective amount of prednisone, prednisolone, methylprednisolone, hydrocortisone, cortisone, cortisol, triamcinolone, or betamethasone. In one embodiment, provided herein is Compound 1 for use in methods of preventing hypotension related to Compound 1 in a cancer patient, wherein the methods comprise administering to the patient a therapeutically effective amount of Compound 1 and a therapeutically effective amount of prednisone, prednisolone, methylprednisolone, hydrocortisone, cortisol, triamcinolone, or betamethasone. In one embodiment, provided herein is Compound 1 for use in methods of preventing hypotension related to Compound 1 in a cancer patient, wherein the methods comprise administering to the patient a therapeutically effective amount of Compound 1 and a therapeutically effective amount of prednisone, prednisolone, methylprednisolone, hydrocortisone, cortisone, cortisol, triamcinolone, or betamethasone. In one embodiment, provided herein is Compound 1 for use in methods of managing hypotension related to Compound 1 in a cancer patient, wherein the methods comprise administering to the patient a therapeutically effective amount of Compound 1 and a therapeutically effective amount of prednisone, prednisolone, methylprednisolone, hydrocortisone, cortisol, triamcinolone, or betamethasone. In one embodiment, provided herein is Compound 1 for use in methods of managing hypotension related to Compound 1 in a cancer patient, wherein the methods comprise administering to the patient a therapeutically effective amount of Compound 1 and a therapeutically effective amount of prednisone, prednisolone, methylprednisolone, hydrocortisone, cortisone, cortisol, triamcinolone, or betamethasone. In one embodiment, provided herein is Compound 1 for use in methods of ameliorating hypotension related to Compound 1 in a cancer patient, wherein the methods comprise administering to the patient a therapeutically effective amount of Compound 1 and a therapeutically effective amount of prednisone, prednisolone, methylprednisolone, hydrocortisone, cortisol, triamcinolone, or betamethasone. In one embodiment, the cancer is a hematological cancer. In one embodiment, provided herein is Compound 1 for use in methods of ameliorating hypotension related to Compound 1 in a cancer patient, wherein the methods comprise administering to the patient a therapeutically effective amount of Compound 1 and a therapeutically effective amount of prednisone, prednisolone, methylprednisolone, hydrocortisone, cortisone, cortisol, triamcinolone, or betamethasone. In one embodiment, the cancer is a hematological cancer. In one embodiment, the hematological cancer is leukemia. In one embodiment, the leukemia is acute myeloid leukemia (AML). In certain embodiments, the AML, is relapsed or refractory AML.

In one embodiment, provided herein are methods of treating, preventing, managing, and/or ameliorating hypotension related to Compound 1 in a cancer patient, wherein the methods comprise administering to the patient a therapeutically effective amount of Compound 1 and a therapeutically effective amount of anakinra. In one embodiment, provided herein is Compound 1 for use in methods of treating, preventing, managing, and/or ameliorating hypotension related to Compound 1 in a cancer patient, wherein the methods comprise administering to the patient a therapeutically effective amount of Compound 1 and a therapeutically effective amount of anakinra. In one embodiment, provided herein is Compound 1 for use in methods of treating hypotension related to Compound 1 in a cancer patient, wherein the methods comprise administering to the patient a therapeutically effective amount of Compound 1 and a therapeutically effective amount of anakinra. In one embodiment, provided herein is Compound I for use in methods of preventing hypotension related to Compound 1 in a cancer patient, wherein the methods comprise administering to the patient a therapeutically effective amount of Compound 1 and a therapeutically effective amount of anakinra. In one embodiment, provided herein is Compound 1 for use in methods of managing hypotension related to Compound 1 in a cancer patient, wherein the methods comprise administering to the patient a therapeutically effective amount of Compound 1 and a therapeutically effective amount of anakinra. In one embodiment, provided herein is Compound 1 for use in methods of ameliorating hypotension related to Compound 1 in a cancer patient, wherein the methods comprise administering to the patient a therapeutically effective amount of Compound 1 and a therapeutically effective amount of anakinra. In one embodiment, the cancer is a hematological cancer. In one embodiment, the hematological cancer is leukemia. In one embodiment, the leukemia is acute myeloid leukemia (AML). In certain embodiments, the AML is relapsed or refractory AML.

In one embodiment, provided herein are methods of treating, preventing, managing, and/or ameliorating hypotension related to Compound 1 in a cancer patient, wherein the methods comprise administering to the patient a therapeutically effective amount of Compound 1 and a therapeutically effective amount of canakinumab. In one embodiment, provided herein is Compound 1 for use in methods of treating, preventing, managing, and/or ameliorating hypotension related to Compound 1 in a cancer patient, wherein the methods comprise administering to the patient a therapeutically effective amount of Compound 1 and a therapeutically effective amount of canakinumab. In one embodiment, provided herein is Compound 1 for use in methods of treating hypotension related to Compound 1 in a cancer patient, wherein the methods comprise administering to the patient a therapeutically effective amount of Compound 1 and a therapeutically effective amount of canakinumab. In one embodiment, provided herein is Compound I for use in methods of preventing hypotension related to Compound 1 in a cancer patient, wherein the methods comprise administering to the patient a therapeutically effective amount of Compound 1 and a therapeutically effective amount of canakinumab. In one embodiment, provided herein is Compound 1 for use in methods of managing hypotension related to Compound 1 in a cancer patient, wherein the methods comprise administering to the patient a therapeutically effective amount of Compound 1 and a therapeutically effective amount of canakinumab. In one embodiment, provided herein is Compound 1 for use in methods of ameliorating hypotension related to Compound 1 in a cancer patient, wherein the methods comprise administering to the patient a therapeutically effective amount of Compound 1 and a therapeutically effective amount of canakinumab.

In one embodiment, provided herein are methods of treating, preventing, managing, and/or ameliorating hypotension related to Compound 1 in a cancer patient, wherein the methods comprise administering to the patient a therapeutically effective amount of Compound 1, a therapeutically effective amount of anakinra and a therapeutically effective amount of vasopressor. In one embodiment, provided herein is Compound 1 for use in methods of treating, preventing, managing, and/or ameliorating hypotension related to Compound 1 in a cancer patient, wherein the methods comprise administering to the patient a therapeutically effective amount of Compound 1, a therapeutically effective amount of anakinra and a therapeutically effective amount of vasopressor. In one embodiment, provided herein is Compound 1 for use in methods of treating hypotension related to Compound 1 in a cancer patient, wherein the methods comprise administering to the patient a therapeutically effective amount of Compound 1, a therapeutically effective amount of anakinra and a therapeutically effective amount of vasopressor. In one embodiment, provided herein is Compound I for use in methods of preventing hypotension related to Compound 1 in a cancer patient, wherein the methods comprise administering to the patient a therapeutically effective amount of Compound 1, a therapeutically effective amount of anakinra and a therapeutically effective amount of vasopressor. In one embodiment, provided herein is Compound 1 for use in methods of managing hypotension related to Compound 1 in a cancer patient, wherein the methods comprise administering to the patient a therapeutically effective amount of Compound 1, a therapeutically effective amount of anakinra and a therapeutically effective amount of vasopressor. In one embodiment, provided herein is Compound 1 for use in methods of ameliorating hypotension related to Compound 1 in a cancer patient, wherein the methods comprise administering to the patient a therapeutically effective amount of Compound 1, a therapeutically effective amount of anakinra and a therapeutically effective amount of vasopressor. In one embodiment, the methods provided herein comprise administering to the patient a single low-dose vasopressor. In one embodiment, the methods provided herein comprise administering to the patient one or more high-dose vasopressors. Non-limiting examples of vasopressors include epinephrine, isoproterenol, phenylephrine, norepinephrine, dobutamine, ephedrine, droxidopa, dopamine, and others known in the art. Exemplary high-doses of vasopressors are provided in Table I:

TABLE II

High-Dose Vasopressors (All Doses Are Required for ≥3 Hours)

| Vasopressor | Dose |
| --- | --- |
| Norepinephrine monotherapy | ≥20 µg/min |
| Dopamine monotherapy | ≥10 µg/kg/min |
| Phenylephrine monotherapy | ≥200 µg/min |
| Epinephrine monotherapy | ≥10 µg/min |
| If on vasopressin | Vasopressin + norepinephrine equivalent of ≥10 µg/min* |
| If on combination vasopressors (not vasopressin) | Norepinephrine equivalent of ≥20 µg/min* |

*VASST Trial vasopressor equivalent equation: norepinephrine equivalent dose = [norepinephrine (µg/min)/2] + [dopamine (µg/kg/min)/2] + [epinephrine (µg/min)] + [phenylephrine (µg/min)/10], Lee et al. *Blood* 2014; 124(2): 188-195.

In one embodiment, the methods provided herein comprise treating, preventing, managing, and/or ameliorating hypotension which is grade 2 hypotension. In one embodiment, the methods provided herein comprise treating, preventing, managing, and/or ameliorating hypotension which is grade ≥3 hypotension.

In one embodiment, provided herein are methods of treating, preventing, managing, and/or ameliorating grade 2 hypotension related to Compound 1 in a cancer patient, wherein the methods comprise administering to the patient a therapeutically effective amount of Compound 1 and a therapeutically effective amount of anakinra. In one embodiment, provided herein is Compound 1 for use in methods of treating, preventing, managing, and/or ameliorating grade 2 hypotension related to Compound 1 in a cancer patient, wherein the methods comprise administering to the patient a therapeutically effective amount of Compound 1 and a therapeutically effective amount of anakinra. In one embodiment, provided herein is Compound 1 for use in methods of treating grade 2 hypotension related to Compound 1 in a cancer patient, wherein the methods comprise administering to the patient a therapeutically effective amount of Compound 1 and a therapeutically effective amount of anakinra. In one embodiment, provided herein is Compound I for use in methods of preventing grade 2 hypotension related to Compound 1 in a cancer patient, wherein the methods comprise administering to the patient a therapeutically effective amount of Compound 1 and a therapeutically effective amount of anakinra. In one embodiment, provided herein is Compound 1 for use in methods of managing grade 2 hypotension related to Compound 1 in a cancer patient, wherein the methods comprise administering to the patient a therapeutically effective amount of Compound 1 and a therapeutically effective amount of anakinra. In one embodiment, provided herein is Compound 1 for use in methods of ameliorating grade 2 hypotension related to Compound 1 in a cancer patient, wherein the methods comprise administering to the patient a therapeutically effective amount of Compound 1 and a therapeutically effective amount of anakinra. In certain embodiments, the methods further comprise administering dexamethasone.

In one embodiment, provided herein are methods of treating, preventing, managing, and/or ameliorating grade ≥3 hypotension related to Compound 1 in a cancer patient, wherein the methods comprise administering to the patient a therapeutically effective amount of Compound 1, a therapeutically effective amount of anakinra and a therapeutically effective amount of vasopressor. In one embodiment, provided herein is Compound 1 for use in methods of treating, preventing, managing, and/or ameliorating grade ≥3 hypotension related to Compound 1 in a cancer patient, wherein the methods comprise administering to the patient a therapeutically effective amount of Compound 1, a therapeutically effective amount of anakinra and a therapeutically effective amount of vasopressor. In one embodiment, provided herein is Compound 1 for use in methods of treating grade ≥3 hypotension related to Compound 1 in a cancer patient, wherein the methods comprise administering to the patient a therapeutically effective amount of Compound 1, a therapeutically effective amount of anakinra and a therapeutically effective amount of vasopressor. In one embodiment, provided herein is Compound I for use in methods of preventing grade ≥3 hypotension related to Compound 1 in a cancer patient, wherein the methods comprise administering to the patient a therapeutically effective amount of Compound 1, a therapeutically effective amount of anakinra and a therapeutically effective amount of vasopressor. In one embodiment, provided herein is Compound 1 for use in methods of managing grade ≥3 hypotension related to Compound 1 in a cancer patient, wherein the methods comprise administering to the patient a therapeutically effective amount of Compound 1, a therapeutically effective amount of anakinra and a therapeutically effective amount of vasopressor. In one embodiment, provided herein is Compound 1 for use in methods of ameliorating grade ≥3 hypotension related to Compound 1 in a cancer patient, wherein the methods comprise administering to the patient a therapeutically effective amount of Compound 1, a therapeutically effective amount of anakinra and a therapeutically effective amount of vasopressor. In one embodiment, the methods provided herein comprise administering to the patient a single low-dose vasopressor. In one embodiment, the methods provided herein comprise administering to the patient one or more high-dose vasopressors. In one embodiment, the vasopressor is selected from epinephrine, isoproterenol, phenylephrine, norepinephrine, dobutamine, ephedrine, droxidopa, dopamine, and others known in the art.

In one embodiment, the cancer is a hematological cancer. In one embodiment, the hematological cancer is leukemia. In one embodiment, the leukemia is acute myeloid leukemia (AML). In certain embodiments, the AML, is relapsed or refractory AML.

Compound 1 is known to promote ubiquitination and degradation of G1 to S phase transition 1 (GSPT 1), a protein translation termination factor, resulting in activation of the integrated stress response (ISR), inhibition of nonsense mediated decay, and induction of apoptosis. Without wishing to be bound by any theory, GSPT-1 degradation by Compound 1 induces general control non-derepressible 2 (GCN2) pathway activation that leads to pro-interleukin-1β (pro-IL-1β) upregulation and caspase 8 activation. Activated caspase 8 processes pro-IL-1β, independently of caspase 1, resulting in interleukin-1β (IL-1β) release and subsequent inflammatory response, including hypotension.

In one embodiment, provided herein are methods suppressing Compound 1 mediated interleukin-1β (IL-1β) induction in a cancer patient, wherein the methods comprise administering to the patient a therapeutically effective amount of Compound 1 and a therapeutically effective amount of a glucocorticoid receptor agonist, an interleukin-1 receptor antagonist, or an interleukin-1β blocker. In one embodiment, provided herein is Compound 1 for use in methods suppressing Compound 1 mediated interleukin-1β

(IL-1β) induction in a cancer patient, wherein the methods comprise administering to the patient a therapeutically effective amount of Compound 1 and a therapeutically effective amount of a glucocorticoid receptor agonist, an interleukin-1 receptor antagonist, or an interleukin-1β blocker. In one embodiment, provided herein is Compound I for use in methods suppressing Compound 1 mediated interleukin-1β (IL-1β) induction in a cancer patient, wherein the methods comprise administering to the patient a therapeutically effective amount of Compound 1 and a therapeutically effective amount of a glucocorticoid receptor agonist. In one embodiment, provided herein is Compound 1 for use in methods suppressing Compound 1 mediated interleukin-1β (IL-1β) induction in a cancer patient, wherein the methods comprise administering to the patient a therapeutically effective amount of Compound 1 and a therapeutically effective amount of an interleukin-1 receptor antagonist. In one embodiment, provided herein is Compound I for use in methods suppressing Compound 1 mediated interleukin-1β (IL-1β) induction in a cancer patient, wherein the methods comprise administering to the patient a therapeutically effective amount of Compound 1 and a therapeutically effective amount of an interleukin-1β blocker. In one embodiment, the glucocorticoid receptor agonist is prednisone, prednisolone, methylpredisolone, hydrocortisone, cortisol, triamcinolone, betamethasone, or dexamethasone. In one embodiment, the glucocorticoid receptor agonist is prednisone, prednisolone, methylpredisolone, hydrocortisone, cortisone, cortisol, triamcinolone, betamethasone, or dexamethasone. In one embodiment, the IL-1 receptor antagonist is anakinra. In one embodiment, the IL-1β blocker is canakinumab.

In one embodiment, provided herein are methods suppressing Compound 1 mediated interleukin-1β (IL-1β) induction in a cancer patient, wherein the methods comprise administering to the patient a therapeutically effective amount of Compound 1 and a therapeutically effective amount of dexamethasone. In one embodiment, provided herein is Compound 1 for use in methods suppressing Compound 1 mediated interleukin-1β (IL-1β) induction in a cancer patient, wherein the methods comprise administering to the patient a therapeutically effective amount of Compound 1 and a therapeutically effective amount of dexamethasone. In another embodiment, provided herein are methods suppressing Compound 1 mediated interleukin-1β (IL-1β) induction in a cancer patient, wherein the methods comprise administering to the patient a therapeutically effective amount of Compound 1 and a therapeutically effective amount of prednisone, prednisolone, methylprednisolone, hydrocortisone, cortisol, triamcinolone, or betamethasone. In another embodiment, provided herein are methods suppressing Compound 1 mediated interleukin-1β (IL-1β) induction in a cancer patient, wherein the methods comprise administering to the patient a therapeutically effective amount of Compound 1 and a therapeutically effective amount of prednisone, prednisolone, methylprednisolone, hydrocortisone, cortisone, cortisol, triamcinolone, or betamethasone. In another embodiment, provided herein is Compound 1 for use in methods suppressing Compound 1 mediated interleukin-1β (IL-1β) induction in a cancer patient, wherein the methods comprise administering to the patient a therapeutically effective amount of Compound 1 and a therapeutically effective amount of prednisone, prednisolone, methylprednisolone, hydrocortisone, cortisol, triamcinolone, or betamethasone. In another embodiment, provided herein is Compound 1 for use in methods suppressing Compound 1 mediated interleukin-1β (IL-1β) induction in a cancer patient, wherein the methods comprise administering to the patient a therapeutically effective amount of Compound 1 and a therapeutically effective amount of prednisone, prednisolone, methylprednisolone, hydrocortisone, cortisone, cortisol, triamcinolone, or betamethasone. In one embodiment, provided herein are methods suppressing Compound 1 mediated interleukin-1β (IL-1β) induction in a cancer patient, wherein the methods comprise administering to the patient a therapeutically effective amount of Compound 1 and a therapeutically effective amount of anakinra. In one embodiment, provided herein is Compound 1 for use in methods suppressing Compound 1 mediated interleukin-1β (IL-1β) induction in a cancer patient, wherein the methods comprise administering to the patient a therapeutically effective amount of Compound 1 and a therapeutically effective amount of anakinra. In one embodiment, provided herein are methods suppressing Compound 1 mediated interleukin-1β (IL-1β) induction in a cancer patient, wherein the methods comprise administering to the patient a therapeutically effective amount of Compound 1 and a therapeutically effective amount of canakinumab. In one embodiment, provided herein is Compound 1 for use in methods suppressing Compound 1 mediated interleukin-1β (IL-1β) induction in a cancer patient, wherein the methods comprise administering to the patient a therapeutically effective amount of Compound 1 and a therapeutically effective amount of canakinumab. In one embodiment, the methods provided herein suppress Compound 1 mediated IL-1β induction by about 10% or more. In one embodiment, the methods provided herein suppress Compound 1 mediated IL-1β induction by about 10% to about 90% or more. In one embodiment, the methods provided herein suppress Compound 1 mediated IL-1β induction by about 10%, 20%, 30%, 40%, 50%, 60%, 70%, 80% or 90%. In one embodiment, the methods provided herein suppress Compound 1 mediated IL-1β induction without altering the rate nor depth of cancer cell killing by Compound 1. In one embodiment, the cancer is a hematological cancer. In one embodiment, the hematological cancer is leukemia. In one embodiment, the leukemia is AML. In certain embodiments, the AML, is relapsed or refractory AML.

In one embodiment, provided herein are methods of treating, preventing, managing, and/or ameliorating an inflammatory response related to by Compound 1 in a cancer patient, wherein the methods comprise administering to the patient a therapeutically effective amount of Compound 1 and a therapeutically effective amount of a glucocorticoid receptor agonist. In one embodiment, provided herein is Compound 1 for use in methods of treating, preventing, managing, and/or ameliorating an inflammatory response related to by Compound 1 in a cancer patient, wherein the methods comprise administering to the patient a therapeutically effective amount of Compound 1 and a therapeutically effective amount of a glucocorticoid receptor agonist. In one embodiment, provided herein is Compound I for use in methods of treating an inflammatory response related to by Compound 1 in a cancer patient, wherein the methods comprise administering to the patient a therapeutically effective amount of Compound 1 and a therapeutically effective amount of a glucocorticoid receptor agonist. In one embodiment, provided herein is Compound 1 for use in methods of preventing an inflammatory response related to by Compound 1 in a cancer patient, wherein the methods comprise administering to the patient a therapeutically effective amount of Compound 1 and a therapeutically effective amount of a glucocorticoid receptor agonist. In one embodiment, provided herein is Compound I for use in methods of managing an inflammatory response related to by Compound 1 in a cancer patient, wherein the methods comprise administering to the patient a therapeutically effective amount of Compound 1 and a therapeutically effective amount of a glucocorticoid receptor agonist. In one embodiment, provided herein is Compound 1 for use in methods of ameliorating an inflammatory response related to by Compound 1 in a cancer patient, wherein the methods comprise administering to the patient a therapeutically effective amount of Compound 1 and a therapeutically effective amount of a glucocorticoid receptor agonist. In one embodiment, the glucocorticoid is prednisone, prednisolone, methylpredisone, hydrocortisone, cortisol, triamcinolone, betamethasone, or dexamethasone. In one embodiment, the glucocorticoid is prednisone, prednisolone, methylprediso-lone, hydrocortisone, cortisone, cortisol, triamcinolone, betamethasone, or dexamethasone.

In one embodiment, provided herein are methods of treating, preventing, managing, and/or ameliorating an inflammatory response related to by Compound 1 in a cancer patient, wherein the methods comprise administering to the patient a therapeutically effective amount of Compound 1 and a therapeutically effective amount of an IL-1 receptor antagonist. In one embodiment, provided herein is Compound 1 for use in methods of treating, preventing, managing, and/or ameliorating an inflammatory response related to by Compound 1 in a cancer patient, wherein the methods comprise administering to the patient a therapeutically effective amount of Compound 1 and a therapeutically effective amount of an IL-1 receptor antagonist. In one embodiment, provided herein is Compound 1 for use in methods of treating an inflammatory response related to by Compound 1 in a cancer patient, wherein the methods comprise administering to the patient a therapeutically effective amount of Compound 1 and a therapeutically effective amount of an IL-1 receptor antagonist. In one embodiment, provided herein is Compound I for use in methods of preventing an inflammatory response related to by Compound 1 in a cancer patient, wherein the methods comprise administering to the patient a therapeutically effective amount of Compound 1 and a therapeutically effective amount of an IL-1 receptor antagonist. In one embodiment, provided herein is Compound 1 for use in methods of managing an inflammatory response related to by Compound 1 in a cancer patient, wherein the methods comprise administering to the patient a therapeutically effective amount of Compound 1 and a therapeutically effective amount of an IL-1 receptor antagonist. In one embodiment, provided herein is Compound 1 for use in methods of ameliorating an inflammatory response related to by Compound 1 in a cancer patient, wherein the methods comprise administering to the patient a therapeutically effective amount of Compound 1 and a therapeutically effective amount of an IL-1 receptor antagonist. In one embodiment, the IL-1 receptor antagonist is anakinra.

In one embodiment, provided herein are methods of treating, preventing, managing, and/or ameliorating an inflammatory response related to by Compound 1 in a cancer patient, wherein the methods comprise administering to the patient a therapeutically effective amount of Compound 1 and a therapeutically effective amount of an IL-1β blocker. In one embodiment, provided herein is Compound 1 for use in methods of treating, preventing, managing, and/or ameliorating an inflammatory response related to by Compound 1 in a cancer patient, wherein the methods comprise administering to the patient a therapeutically effective amount of Compound 1 and a therapeutically effective amount of an IL-1β blocker. In one embodiment, provided herein is Compound 1 for use in methods of treating an inflammatory response related to by Compound 1 in a cancer patient, wherein the methods comprise administering to the patient a therapeutically effective amount of Compound 1 and a therapeutically effective amount of an IL-1β blocker. In one embodiment, provided herein is Compound 1 for use in methods of preventing an inflammatory response related to by Compound 1 in a cancer patient, wherein the methods comprise administering to the patient a therapeutically effective amount of Compound 1 and a therapeutically effective amount of an IL-1β blocker. In one embodiment, provided herein is Compound I for use in methods of managing, an inflammatory response related to by Compound 1 in a cancer patient, wherein the methods comprise administering to the patient a therapeutically effective amount of Compound 1 and a therapeutically effective amount of an IL-1β blocker. In one embodiment, provided herein is Compound 1 for use in methods of ameliorating an inflammatory response related to by Compound 1 in a cancer patient, wherein the methods comprise administering to the patient a therapeutically effective amount of Compound 1 and a therapeutically effective amount of an IL-1β blocker. In one embodiment, the IL-1β blocker is canakinumab.

In one embodiment, provided herein are methods of treating, preventing, managing, and/or ameliorating an inflammatory response related to by Compound 1 in a cancer patient, wherein the methods comprise administering to the patient a therapeutically effective amount of Compound 1 and a therapeutically effective amount of dexamethasone. In one embodiment, provided herein is Compound 1 for use in methods of treating, preventing, managing, and/or ameliorating an inflammatory response related to by Compound 1 in a cancer patient, wherein the methods comprise administering to the patient a therapeutically effective amount of Compound 1 and a therapeutically effective amount of dexamethasone. In one embodiment, provided herein is Compound 1 for use in methods of treating an inflammatory response related to by Compound 1 in a cancer patient, wherein the methods comprise administering to the patient a therapeutically effective amount of Compound 1 and a therapeutically effective amount of dexamethasone. In one embodiment, provided herein is Compound 1 for use in methods of preventing an inflammatory response related to by Compound 1 in a cancer patient, wherein the methods comprise administering to the patient a therapeutically effective amount of Compound 1 and a therapeutically effective amount of dexamethasone. In one embodiment, provided herein is Compound 1 for use in methods of managing an inflammatory response related to by Compound 1 in a cancer patient, wherein the methods comprise administering to the patient a therapeutically effective amount of Compound 1 and a therapeutically effective amount of dexamethasone. In one embodiment, provided herein is Compound 1 for use in methods of ameliorating an inflammatory response related to by Compound 1 in a cancer patient, wherein the methods comprise administering to the patient a therapeutically effective amount of Compound 1 and a therapeutically effective amount of dexamethasone. In other embodiments, provided herein are methods of treating, preventing, managing, and/or ameliorating an inflammatory response related to by Compound 1 in a cancer patient, wherein the methods comprise administering to the patient a therapeutically effective amount of Compound 1 and a therapeutically effective amount of prednisone, prednisolone, methylprednisolone, hydrocortisone, cortisol, triamcinolone, or betamethasone. In other embodiments, provided herein are methods of treating, preventing, managing, and/or ameliorating an inflammatory response related to by Compound 1 in a cancer patient, wherein the methods comprise administering to the patient a therapeutically effective amount of Compound 1 and a therapeutically effective amount of prednisone, prednisolone, methylprednisolone, hydrocortisone, cortisone, cortisol, triamcinolone, or betamethasone. In other embodiments, provided herein is Compound 1 for use in methods of treating, preventing, managing, and/or ameliorating an inflammatory response related to by Compound 1 in a cancer patient, wherein the methods comprise administering to the patient a therapeutically effective amount of Compound 1 and a therapeutically effective amount of prednisone, prednisolone, methylprednisolone, hydrocortisone, cortisol, triamcinolone, or betamethasone. In other embodiments, provided herein is Compound 1 for use in methods of treating, preventing, managing, and/or ameliorating an inflammatory response related to by Compound 1 in a cancer patient, wherein the methods comprise administering to the patient a therapeutically effective amount of Compound 1 and a therapeutically effective amount of prednisone, prednisolone, methylprednisolone, hydrocortisone, cortisone, cortisol, triamcinolone, or betamethasone. In other embodiments, provided herein is Compound I for use in methods of treating an inflammatory response related to by Compound 1 in a cancer patient, wherein the methods comprise administering to the patient a therapeutically effective amount of Compound 1 and a therapeutically effective amount of prednisone, prednisolone, methylprednisolone, hydrocortisone, cortisol, triamcinolone, or betamethasone. In other embodiments, provided herein is Compound I for use in methods of treating an inflammatory response related to by Compound 1 in a cancer patient, wherein the methods comprise administering to the patient a therapeutically effective amount of Compound 1 and a therapeutically effective amount of prednisone, prednisolone, methylprednisolone, hydrocortisone, cortisone, cortisol, triamcinolone, or betamethasone. In other embodiments, provided herein is Compound 1 for use in methods of preventing an inflammatory response related to by Compound 1 in a cancer patient, wherein the methods comprise administering to the patient a therapeutically effective amount of Compound 1 and a therapeutically effective amount of prednisone, prednisolone, methylprednisolone, hydrocortisone, cortisol, triamcinolone, or betamethasone. In other embodiments, provided herein is Compound 1 for use in methods of preventing an inflammatory response related to by Compound 1 in a cancer patient, wherein the methods comprise administering to the patient a therapeutically effective amount of Compound 1 and a therapeutically effective amount of prednisone, prednisolone, methylprednisolone, hydrocortisone, cortisone, cortisol, triamcinolone, or betamethasone. In other embodiments, provided herein is Compound 1 for use in methods of managing an inflammatory response related to by Compound 1 in a cancer patient, wherein the methods comprise administering to the patient a therapeutically effective amount of Compound 1 and a therapeutically effective amount of prednisone, prednisolone, methylprednisolone, hydrocortisone, cortisol, triamcinolone, or betamethasone. In other embodiments, provided herein is Compound 1 for use in methods of managing an inflammatory response related to by Compound 1 in a cancer patient, wherein the methods comprise administering to the patient a therapeutically effective amount of Compound 1 and a therapeutically effective amount of prednisone, prednisolone, methylprednisolone, hydrocortisone, cortisone, cortisol, triamcinolone, or betamethasone. In other embodiments, provided herein is Compound 1 for use in methods of ameliorating an inflammatory response related to by Compound 1 in a cancer patient, wherein the methods comprise administering to the patient a therapeutically effective amount of Compound 1 and a therapeutically effective amount of prednisone, prednisolone, methylprednisolone, hydrocortisone, cortisol, triamcinolone, or betamethasone. In other embodiments, provided herein is Compound 1 for use in methods of ameliorating an inflammatory response related to by Compound 1 in a cancer patient, wherein the methods comprise administering to the patient a therapeutically effective amount of Compound 1 and a therapeutically effective amount of prednisone, prednisolone, methylprednisolone, hydrocortisone, cortisone, cortisol, triamcinolone, or betamethasone. In one embodiment, the cancer is a hematological cancer. In one embodiment, the hematological cancer is leukemia. In one embodiment, the leukemia is acute myeloid leukemia (AML). In certain embodiments, the AML is relapsed or refractory AML.

In one embodiment, provided herein are methods of treating, preventing, managing, and/or ameliorating an inflammatory response related to by Compound 1 in a cancer patient, wherein the methods comprise administering to the patient a therapeutically effective amount of Compound 1 and a therapeutically effective amount of anakinra. In one embodiment, provided herein is Compound 1 for use methods of treating, preventing, managing, and/or ameliorating an inflammatory response related to by Compound 1 in a cancer patient, wherein the methods comprise administering to the patient a therapeutically effective amount of Compound 1 and a therapeutically effective amount of anakinra. In one embodiment, provided herein is Compound I for use methods of treating an inflammatory response related to by Compound 1 in a cancer patient, wherein the methods comprise administering to the patient a therapeutically effective amount of Compound 1 and a therapeutically effective amount of anakinra. In one embodiment, provided herein is Compound 1 for use methods of preventing an inflammatory response related to by Compound 1 in a cancer patient, wherein the methods comprise administering to the patient a therapeutically effective amount of Compound 1 and a therapeutically effective amount of anakinra. In one embodiment, provided herein is Compound 1 for use methods of managing an inflammatory response related to by Compound 1 in a cancer patient, wherein the methods comprise administering to the patient a therapeutically effective amount of Compound 1 and a therapeutically effective amount of anakinra. In one embodiment, provided herein is Compound 1 for use methods of ameliorating an inflammatory response related to by Compound 1 in a cancer patient, wherein the methods comprise administering to the patient a therapeutically effective amount of Compound 1 and a therapeutically effective amount of anakinra. In one embodiment, the cancer is a hematological cancer. In one embodiment, the hematological cancer is leukemia. In one embodiment, the leukemia is acute myeloid leukemia (AML). In certain embodiments, the AML, is relapsed or refractory AML.

In one embodiment, provided herein are methods of treating, preventing, managing, and/or ameliorating an inflammatory response related to by Compound 1 in a cancer patient, wherein the methods comprise administering to the patient a therapeutically effective amount of Compound 1 and a therapeutically effective amount of canakinumab. In one embodiment, provided herein is Compound 1 for use in methods of treating, preventing, managing, and/or ameliorating an inflammatory response related to by Compound 1 in a cancer patient, wherein the methods comprise administering to the patient a therapeutically effective amount of Compound 1 and a therapeutically effective amount of canakinumab. In one embodiment, provided herein is Compound 1 for use in methods of treating an inflammatory response related to by Compound 1 in a cancer patient, wherein the methods comprise administering to the patient a therapeutically effective amount of Compound 1 and a therapeutically effective amount of canakinumab. In one embodiment, provided herein is Compound 1 for use in methods of preventing an inflammatory response related to by Compound 1 in a cancer patient, wherein the methods comprise administering to the patient a therapeutically effective amount of Compound 1 and a therapeutically effective amount of canakinumab. In one embodiment, provided herein is Compound 1 for use in methods of managing an inflammatory response related to by Compound 1 in a cancer patient, wherein the methods comprise administering to the patient a therapeutically effective amount of Compound 1 and a therapeutically effective amount of canakinumab. In one embodiment, provided herein is Compound 1 for use in methods of ameliorating an inflammatory response related to by Compound 1 in a cancer patient, wherein the methods comprise administering to the patient a therapeutically effective amount of Compound 1 and a therapeutically effective amount of canakinumab. In one embodiment, the cancer is a hematological cancer. In one embodiment, the hematological cancer is leukemia. In one embodiment, the leukemia is acute myeloid leukemia (AML). In certain embodiments, the AML is relapsed or refractory AML.

Also provided herein is Compound 1 for use in methods of treating any disease provided herein related to by Compound 1, wherein the methods comprise administering to the patient a therapeutically effective amount of Compound 1 and a therapeutically effective amount of any glucocorticoid receptor agonist, interleukin-1 receptor antagonist, or interleukin-1β blocker disclosed herein.

In certain embodiments, the methods provided herein further comprise administering an additional agent selected from JAK inhibitors, FLT3 inhibitors, mTOR inhibitors, spliceosome inhibitors, BET inhibitors, SMG1 inhibitors, ERK inhibitors, LSD1 inhibitors, BH3 mimetics, topoisomerase inhibitors, and RTK inhibitors.

In certain embodiments, the cancer patients in the methods provided herein are those who have been previously treated for cancer but are non-responsive to cancer therapies, as well as those who have not previously been treated. Also encompassed are methods of treating patients regardless of patient's age, although some diseases or disorders are more common in certain age groups. Further encompassed are methods of treating patients who have undergone surgery in an attempt to treat the cancer at issue, as well as those who have not. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

In certain embodiments, the cancer is a solid tumor or a hematological cancer. In certain embodiments, the cancer is interleukin-3 (IL-3) independent. In certain embodiments, the cancer is a solid tumor. In certain embodiments, the solid tumor is metastatic. In certain embodiments, the solid tumor is drug-resistant.

In certain embodiments, cancer refers to a disease of skin tissues, organs, blood, and vessels. In certain embodiments, the cancer is a solid tumor, including, but not limited to, cancers of the bladder, bone, blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, colorectal cancer, including stage 3 and stage 4, unresectable colorectal carcinoma, metastatic hepatocellular carcinoma, Kaposi's sarcoma, karyotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, carcinoma, including papillary thyroid carcinoma, follicular thyroid carcinoma, and medullary thyroid carcinoma, and leiomyoma.

In certain embodiments, the cancer is a solid tumor, including, but not limited to, cancers of the skin, central nervous system, soft tissue, salivary gland, ovary, kidney, lung, bone, stomach, endometrium, pancreas, urinary tract, thyroid, upper aerodigestive tract, breast, large intestine, oesophagus, prostate, liver, autonomic ganglia, and malignant pleural mesothelioma.

In certain embodiments, the solid tumor is hepatocellular carcinoma, prostate cancer, ovarian cancer, or glioblastoma.

In certain embodiments, the solid tumor is breast cancer, kidney cancer, pancreatic cancer, gastrointestinal cancer, lung cancer, neuroendocrine tumor (NET), or renal cell carcinoma (RCC).

In certain embodiments, the cancer is a hematological cancer. In certain embodiments, the hematological cancer is metastatic. In certain embodiments, the hematological cancer is drug resistant to at least one anti-cancer therapy. In certain embodiments the hematological cancer is relapsed or refractory to at least one anti-cancer therapy.

In one embodiment, the hematological cancer is multiple myeloma (MM). In one embodiment, the hematological cancer is relapsed/refractory (R/R) MM. In one embodiment, the patient having R/R MM has impaired renal function.

In one embodiment, the hematological cancer is acute myelogenous leukemia (AML). In one embodiment, the hematological cancer is acute lymphocytic leukemia (ALL). In one embodiment, the hematological cancer is adult T-cell leukemia. In one embodiment, the hematological cancer is chronic lymphocytic leukemia (CLL). In one embodiment, the hematological cancer is hairy cell leukemia. In one embodiment, the hematological cancer is myelodysplasia. In one embodiment, the hematological cancer is a myeloproliferative disorder or myeloproliferative neoplasm (MPN).

In one embodiment, the hematological cancer is chronic myelogenous leukemia (CML). In one embodiment, the hematological cancer is myelodysplastic syndrome (MDS). In one embodiment, the hematological cancer is human lymphotropic virus-type 1 (HTLV-1) leukemia. In one embodiment, the hematological cancer is mastocytosis. In one embodiment, the hematological cancer is B-cell acute lymphoblastic leukemia. In one embodiment, the hematological cancer is CLL.

In one embodiment, the hematological cancer is selected from diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, mantle cell lymphoma (MCL), Hodgkin lymphoma (HL), non-Hodgkin lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter's transformation, nodal marginal zone lymphoma, and ALK-positive large B-cell lymphoma in a subject. In one embodiment, the hematological cancer is HL. In one embodiment, the hematological cancer is NHL. In one embodiment, the hematological cancer is indolent lymphoma including, for example, DLBCL, follicular lymphoma, and marginal zone lymphoma.

In one embodiment, the hematological cancer is leukemia. In one embodiment, the leukemia is acute myeloid leukemia (AML). In one embodiment, the AML is relapsed or refractory AML. In one embodiment, the AML is newly diagnosed AML. In another embodiment, the AML has FAB classification M0/1. In another embodiment, the AML has FAB classification M2. In another embodiment, the AML has FAB classification M3. In another embodiment, the AML has FAB classification M4. In another embodiment, the AML has FAB classification M5. In one embodiment, the AML is AML with at least one recurrent genetic abnormality (for example, AML with translocation between chromosomes 8 and 21; AML with translocation or inversion in chromosome 16; AML with translocation between chromosomes 9 and 11; APL (M3) with translocation between chromosomes 15 and 17; AML with translocation between chromosomes 6 and 9; AML with translocation or inversion in chromosome 3); AML (megakaryoblastic) with a translocation between chromosomes 1 and 22; AML with myelodysplasia-related changes; AML related to previous chemotherapy or radiation (for example, alkylating agent-related AML; or Topoisomerase II inhibitor-related AML); AML not otherwise categorized (for example, AML that does not fall into the above categories, i.e. AML minimally differentiated (M0); AML with minimal maturation (M1); AML with maturation (M2); Acute myelomonocytic leukemia (M4); Acute monocytic leukemia (M5); Acute erythroid leukemia (M6); Acute megakaryoblastic leukemia (M7); Acute basophilic leukemia; or Acute panmyelosis with fibrosis); Myeloid Sarcoma (also known as granulocytic sarcoma, chloroma or extramedullary myeloblastoma); or Undifferentiated and biphenotypic acute leukemias (also known as mixed phenotype acute leukemias). In one embodiment, the AML is characterized by a mutant allele of IDH2. In one aspect of this embodiment, the mutant allele of IDH2 has an R140X mutation. In another aspect of this embodiment, the R140X mutation is a R140Q mutation. In another aspect of this embodiment, the R140X mutation is a R140W mutation. In another aspect of this embodiment, the R140X mutation is a R140L mutation. In another aspect of this embodiment, the mutant allele of IDH2 has an R172X mutation. In another aspect of this embodiment, the R172X mutation is a R172K mutation. In another aspect of this embodiment, the R172X mutation is a R172G mutation.

In one embodiment, the AML is relapsed AML after allogeneic HSCT. In one embodiment, the AML is second or later relapsed AML. In one embodiment, the AML is refractory to initial induction or re-induction treatment. In certain embodiments, the AML is refractory to at least one induction/reinduction or consolidation therapy. In one embodiment, the AML is refractory to or relapsed after hypomethylating agent (HMA). As used herein, HMA failure is defined as primary progression or lack of clinical benefit after a minimum of 6 cycles or unable to tolerate HMA due to toxicity. In one embodiment, the AML is relapsed within 1 year of initial treatment (excluding AML with favorable-risk status).

In some embodiments, the methods comprise administering to the subject Compound 1 and dexamethasone in combination with an additional active agent in amounts effective to treat, prevent and/or manage acute myeloid leukemia.

In one embodiment, the hematological cancer is acute lymphocytic leukemia (ALL). In some embodiments, ALL includes leukemia that originates in the blast cells of the bone marrow (B-cells), thymus (T-cells), and lymph nodes. The ALL can be categorized according to the French-American-British (FAB) Morphological Classification Scheme as L1—Mature-appearing lymphoblasts (T-cells or pre-B-cells), L2—Immature and pleomorphic (variously shaped) lymphoblasts (T-cells or pre-B-cells), and L3—Lymphoblasts (B-cells; Burkitt's cells). In one embodiment, the ALL originates in the blast cells of the bone marrow (B-cells). In one embodiment, the ALL originates in the thymus (T-cells). In one embodiment, the ALL originates in the lymph nodes. In one embodiment, the ALL is L1 type characterized by mature-appearing lymphoblasts (T-cells or pre-B-cells). In one embodiment, the ALL is L2 type characterized by immature and pleomorphic (variously shaped) lymphoblasts (T-cells or pre-B-cells). In one embodiment, the ALL is L3 type characterized by lymphoblasts (B-cells; Burkitt's cells). In certain embodiments, the ALL is T-cell leukemia. In one embodiment, the T-cell leukemia is peripheral T-cell leukemia. In another embodiment, the T-cell leukemia is T-cell lymphoblastic leukemia. In another embodiment, the T-cell leukemia is cutaneous T-cell leukemia. In another embodiment, the T-cell leukemia is adult T-cell leukemia. In certain embodiments, the methods provided herein comprise the step of administering to the subject a therapeutically effective amount of Compound 1 and dexamethasone. In some embodiments, the methods provided herein comprise the step of administering to the subject a therapeutically effective amount of Compound 1 and prednisone, prednisolone, methylprednisolone, hydrocortisone, cortisol, triamcinolone, or betamethasone. In some embodiments, the methods provided herein comprise the step of administering to the subject a therapeutically effective amount of Compound 1 and prednisone, prednisolone, methylprednisolone, hydrocortisone, cortisone, cortisol, triamcinolone, or betamethasone. In some embodiments, the methods comprise the step of administering to the subject Compound 1 and dexamethasone, in combination with an additional active agent in amounts effective to treat, prevent and/or manage ALL. In other embodiments, the methods comprise the step of administering to the subject Compound 1 and prednisone, prednisolone, methylprednisolone, hydrocortisone, cortisol, triamcinolone, or betamethasone, in combination with an additional active agent in amounts effective to treat, prevent and/or manage ALL. In other embodiments, the methods comprise the step of administering to the subject Compound 1 and prednisone, prednisolone, methylprednisolone, hydrocortisone, cortisone, cortisol, triamcinolone, or betamethasone, in combination with an additional active agent in amounts effective to treat, prevent and/or manage ALL.

In certain embodiments, the methods provided herein comprise the step of administering to the subject a therapeutically effective amount of Compound 1 and anakinra. In some embodiments, the methods comprise the step of administering to the subject Compound 1 and anakinra, in combination with an additional active agent in amounts effective to treat, prevent and/or manage ALL.

In certain embodiments, the methods provided herein comprise the step of administering to the subject a therapeutically effective amount of Compound 1 and canakinumab. In some embodiments, the methods comprise the step of administering to the subject Compound 1 and canakinumab, in combination with an additional active agent in amounts effective to treat, prevent and/or manage ALL In one embodiment, the hematological cancer is chronic myelogenous leukemia (CML) in a subject. The methods comprise the step of administering to the subject a therapeutically effective amount of Compound 1 and dexamethasone. In some embodiments, the methods comprise the step of administering to the subject Compound 1 and dexamethasone, in combination with an additional active agent in amounts effective to treat, prevent and/or manage CML. In some embodiments, the methods comprise the step of administering to the subject a therapeutically effective amount of Compound 1 and prednisone, prednisolone, methylprednisolone, hydrocortisone, cortisol, triamcinolone, or betamethasone. In some embodiments, the methods comprise the step of administering to the subject a therapeutically effective amount of Compound 1 and prednisone, prednisolone, methylprednisolone, hydrocortisone, cortisone, cortisol, triamcinolone, or betamethasone. In some embodiments, the methods comprise the step of administering to the subject Compound 1 and prednisone, prednisolone, methylprednisolone, hydrocortisone, cortisol, triamcinolone, or betamethasone, in combination with an additional active agent in amounts effective to treat, prevent and/or manage CML. In some embodiments, the methods comprise the step of administering to the subject Compound 1 and prednisone, prednisolone, methylprednisolone, hydrocortisone, cortisone, cortisol, triamcinolone, or betamethasone, in combination with an additional active agent in amounts effective to treat, prevent and/or manage CML. In some embodiments, the methods comprise the step of administering to the subject a therapeutically effective amount of Compound 1 and anakinra. In some embodiments, the methods comprise the step of administering to the subject Compound 1 and anakinra, in combination with an additional active agent in amounts effective to treat, prevent and/or manage CML. In some embodiments, the methods comprise the step of administering to the subject a therapeutically effective amount of Compound 1 and canakinumab. In some embodiments, the methods comprise the step of administering to the subject Compound 1 and canakinumab, in combination with an additional active agent in amounts effective to treat, prevent and/or manage CML.

In one embodiment, the hematological cancer is chronic lymphocytic leukemia (CLL) in a subject. The methods comprise the step of administering to the subject a therapeutically effective amount of Compound 1 and dexamethasone. In some embodiments, the methods comprise the step of administering to the subject Compound 1 and dexamethasone, in combination with an additional active agent in amounts effective to treat, prevent and/or manage CLL. In some embodiments, the methods comprise the step of administering to the subject a therapeutically effective amount of Compound 1 and prednisone, prednisolone, methylprednisolone, hydrocortisone, cortisol, triamcinolone, or betamethasone. In some embodiments, the methods comprise the step of administering to the subject a therapeutically effective amount of Compound 1 and prednisone, prednisolone, methylprednisolone, hydrocortisone, cortisone, cortisol, triamcinolone, or betamethasone. In some embodiments, the methods comprise the step of administering to the subject Compound 1 and prednisone, prednisolone, methylprednisolone, hydrocortisone, cortisol, triamcinolone, or betamethasone, in combination with an additional active agent in amounts effective to treat, prevent and/or manage CLL. In some embodiments, the methods comprise the step of administering to the subject Compound 1 and prednisone, prednisolone, methylprednisolone, hydrocortisone, cortisone, cortisol, triamcinolone, or betamethasone, in combination with an additional active agent in amounts effective to treat, prevent and/or manage CLL. In some embodiments, the methods comprise the step of administering to the subject a therapeutically effective amount of Compound 1 and anakinra. In some embodiments, the methods comprise the step of administering to the subject Compound 1 and anakinra, in combination with an additional active agent in amounts effective to treat, prevent and/or manage CLL. In some embodiments, the methods comprise the step of administering to the subject a therapeutically effective amount of Compound 1 and canakinumab. In some embodiments, the methods comprise the step of administering to the subject Compound 1 and canakinumab, in combination with an additional active agent in amounts effective to treat, prevent and/or manage CLL.

In one embodiment, the hematological cancer is myelodysplastic syndrome (MDS). In one embodiment, the MDS is relapsed, resistant or refractory MDS. In one embodiment, MDS is refractory anemia (RA); RA with ringed sideroblasts (RARS); RA with excess of blasts (RAEB); refractory cytopenia with multilineage dysplasia (RCMD), refractory cytopenia with unilineage dysplasia (RCUD); unclassifiable myelodysplastic syndrome (MDS-U), myelodysplastic syndrome associated with an isolated del(5q) chromosome abnormality, therapy-related myeloid neoplasms or chronic myelomonocytic leukemia (CMML). In some embodiments, the MDS is very low risk, low risk, intermediate risk, high risk or very high risk MDS. In one embodiment, the MDS is very low risk. In another embodiment, the MDS is low risk. In another embodiment, the MDS is intermediate risk. In another embodiment, the MDS is high risk. In another embodiment, the MDS is very high risk MDS. In one embodiment, the MDS is relapsed or refractory high risk MDS. In one embodiment, the MDS is with a score >3.5 points in the Revised International Prognostic Scoring System (IPSS-R) (eg, IPSS-R intermediate risk (in combination with more than 10% bone marrow blasts or poor or very poor IPSS-R cytogenetic risk), IPSS-R high and IPSS-R very high risk). In one embodiment, the MDS is not suitable for other established therapies (eg, transplant or hypomethylating agent). In some embodiments, the MDS is primary or de novo MDS. In other embodiments, the MDS is secondary MDS. In other embodiments, the MDS is refractory to initial induction or re-induction treatment. In certain embodiments, the MDS is refractory to at least one induction/reinduction or consolidation therapy. In certain embodiments, the methods of treating, preventing and/or managing MDS in a subject comprise the step of administering to the subject a therapeutically effective amount of Compound 1 and dexamethasone. In certain embodiments, the methods of treating, preventing and/or managing MDS in a subject comprise the step of administering to the subject a therapeutically effective amount of Compound 1 and prednisone, prednisolone, methylprednisolone, hydrocortisone, cortisol, triamcinolone, or betamethasone. In certain embodiments, the methods of treating, preventing and/or managing MDS in a subject comprise the step of administering to the subject a therapeutically effective amount of Compound 1 and prednisone, prednisolone, methylprednisolone, hydrocortisone, hydrocortisone, cortisol, triamcinolone, or betamethasone. In certain embodiments, provided herein is Compound 1 for use in methods of treating, preventing and/or managing MDS in a subject, wherein the method comprises the step of administering to the subject a therapeutically effective amount of Compound 1 and prednisone, prednisolone, methylprednisolone, hydrocortisone, cortisol, triamcinolone, or betamethasone. In certain embodiments, provided herein is Compound 1 for use in methods of treating, preventing and/or managing MDS in a subject, wherein the method comprises the step of administering to the subject a therapeutically effective amount of Compound 1 and prednisone, prednisolone, methylprednisolone, hydrocortisone, cortisone, cortisol, triamcinolone, or betamethasone. In certain embodiments, provided herein is Compound 1 for use in methods of treating MDS in a subject, wherein the method comprises the step of administering to the subject a therapeutically effective amount of Compound 1 and prednisone, prednisolone, methylprednisolone, hydrocortisone, cortisol, triamcinolone, or betamethasone. In certain embodiments, provided herein is Compound 1 for use in methods of treating MDS in a subject, wherein the method comprises the step of administering to the subject a therapeutically effective amount of Compound 1 and prednisone, prednisolone, methylprednisolone, hydrocortisone, cortisone, cortisol, triamcinolone, or betamethasone. In certain embodiments, provided herein is Compound 1 for use in methods of preventing MDS in a subject, wherein the method comprises the step of administering to the subject a therapeutically effective amount of Compound 1 and prednisone, prednisolone, methylprednisolone, hydrocortisone, cortisol, triamcinolone, or betamethasone. In certain embodiments, provided herein is Compound 1 for use in methods of preventing MDS in a subject, wherein the method comprises the step of administering to the subject a therapeutically effective amount of Compound 1 and prednisone, prednisolone, methylprednisolone, hydrocortisone, cortisone, cortisol, triamcinolone, or betamethasone. In certain embodiments, provided herein is Compound 1 for use in methods of managing MDS in a subject, wherein the method comprises the step of administering to the subject a therapeutically effective amount of Compound 1 and prednisone, prednisolone, methylprednisolone, hydrocortisone, cortisol, triamcinolone, or betamethasone. In certain embodiments, provided herein is Compound 1 for use in methods of managing MDS in a subject, wherein the method comprises the step of administering to the subject a therapeutically effective amount of Compound 1 and prednisone, prednisolone, methylprednisolone, hydrocortisone, cortisone, cortisol, triamcinolone, or betamethasone. In certain embodiments, the methods of treating, preventing and/or managing MDS in a subject comprise the step of administering to the subject a therapeutically effective amount of Compound 1 and anakinra. In certain embodiments, Compound I for use in methods of treating, preventing and/or managing MDS in a subject comprise the step of administering to the subject a therapeutically effective amount of Compound 1 and anakinra. In certain embodiments, provided herein is Compound 1 for use in methods of treating MDS in a subject, wherein the method comprises the step of administering to the subject a therapeutically effective amount of Compound 1 and anakinra. In certain embodiments, provided herein is Compound 1 for use in methods of preventing MDS in a subject, wherein the method comprises the step of administering to the subject a therapeutically effective amount of Compound 1 and anakinra. In certain embodiments, provided herein is Compound 1 for use in methods of managing MDS in a subject, wherein the method comprises the step of administering to the subject a therapeutically effective amount of Compound 1 and anakinra. In certain embodiments, the methods of treating, preventing and/or managing MDS in a subject comprise the step of administering to the subject a therapeutically effective amount of Compound 1 and canakinumab. In certain embodiments, provided herein is Compound 1 for use in methods of treating, preventing and/or managing MDS in a subject, wherein the method comprises the step of administering to the subject a therapeutically effective amount of Compound 1 and canakinumab. In certain embodiments, provided herein is Compound 1 for use in methods of treating MDS in a subject, wherein the method comprises the step of administering to the subject a therapeutically effective amount of Compound 1 and canakinumab. In certain embodiments, provided herein is Compound 1 for use in methods of preventing MDS in a subject, wherein the method comprises the step of administering to the subject a therapeutically effective amount of Compound 1 and canakinumab. In certain embodiments, provided herein is Compound 1 for use in methods of managing MDS in a subject, wherein the method comprises the step of administering to the subject a therapeutically effective amount of Compound 1 and canakinumab.

In one embodiment, the hematological cancer is a myeloproliferative neoplasm. In one embodiment, the myeloproliferative neoplasm is polycythemia vera, primary or essential thrombocythemia, myelofibrosis, chronic myelogenous leukemia, chronic neutrophilic leukemia, juvenile myelomonocytic leukemia, chronic eosinophilic leukemia, or hyper eosinophilic syndrome. In one embodiment, the myeloproliferative neoplasm is polycythemia vera, primary or essential thrombocythemia, primary or idiopathic myelofibrosis, secondary myeolofibrosis, post polycythemia vera myelofibrosis, post essential thrombocythemia myelofibrosis, chronic myelogenous leukemia, chronic neutrophilic leukemia, juvenile myelomonocytic leukemia, chronic eosinophilic leukemia, or hyper eosinophilic syndrome. In one embodiment, the myeloproliferative neoplasm is polycythemia vera. In one embodiment, the myeloproliferative neoplasm is primary or essential thrombocythemia. In one embodiment, the myeloproliferative neoplasm is myelofibrosis. In one embodiment, the myeloproliferative neoplasm is primary or idiopathic myelofibrosis. In one embodiment, the myeloproliferative neoplasm is secondary myeolofibrosis. In one embodiment, the myeloproliferative neoplasm is post polycythemia vera myelofibrosis. In one embodiment, the myeloproliferative neoplasm is post essential thrombocythemia myelofibrosis. In one embodiment, the myeloproliferative neoplasm is chronic myelogenous leukemia. In one embodiment, the myeloproliferative neoplasm is chronic neutrophilic leukemia. In one embodiment, the myeloproliferative neoplasm is juvenile myelomonocytic leukemia. In one embodiment, the myeloproliferative neoplasm is chronic eosinophilic leukemia. In one embodiment, the myeloproliferative neoplasm is hyper eosinophilic syndrome. In certain embodiments, the myeloproliferative neoplasm is interleukin-3 (IL-3) independent. In some embodiments, the myeloproliferative neoplasm is characterized by a JAK mutation, for example, a V617 mutation, such as V617F.

In one embodiment, the methods provided herein comprise intravenous administration of Compound 1. In one embodiment, a formulation of Compound 1 is dissolved in water to form an aqueous solution for intravenous administration in methods provided herein.

In certain embodiments, the methods provided herein comprise administering Compound 1 and a glucocorticoid receptor agonist, an interleukin-1 receptor antagonist, or an interleukin-1β blocker to patients with impaired renal function. In certain embodiments, provided herein are methods of providing appropriate dose adjustments for patients with impaired renal function due to, but not limited to, disease, aging, or other patient factors.

In certain embodiments, a therapeutically or prophylactically effective amount of Compound 1 is from about 0.005 to about 20 mg per day, from about 0.05 to 20 mg per day, from about 0.01 to about 10 mg per day, from about 0.01 to about 7 mg per day, from about 0.01 to about 5 mg per day, from about 0.01 to about 3 mg per day, from about 0.05 to about 10 mg per day, from about 0.05 to about 7 mg per day, from about 0.05 to about 5 mg per day, from about 0.05 to about 3 mg per day, from about 0.1 to about 15 mg per day, from about 0.1 to about 10 mg per day, from about 0.1 to about 7 mg per day, from about 0.1 to about 5 mg per day, from about 0.1 to about 3 mg per day, from about 0.5 to about 10 mg per day, from about 0.05 to about 5 mg per day, from about 0.5 to about 3 mg per day, from about 0.5 to about 2 mg per day, from about 0.3 to about 10 mg per day, from about 0.3 to about 8.5 mg per day, from about 0.3 to about 8.1 mg per day, from about 0.6 to about 10 mg per day or from about 0.6 to about 5 mg per day. In one embodiment, a therapeutically or prophylactically effective amount of Compound 1 is from about 0.005 to about 20 mg per day. In one embodiment, a therapeutically or prophylactically effective amount of Compound 1 is, from about 0.05 to 20 mg per day. In one embodiment, a therapeutically or prophylactically effective amount of Compound 1 is from about 0.01 to about 10 mg per day. In one embodiment, a therapeutically or prophylactically effective amount of Compound 1 is from about 0.01 to about 7 mg per day. In one embodiment, a therapeutically or prophylactically effective amount of Compound 1 is from about 0.01 to about 5 mg per day. In one embodiment, a therapeutically or prophylactically effective amount of Compound 1 is from about 0.01 to about 3 mg per day. In one embodiment, a therapeutically or prophylactically effective amount of Compound 1 is from about 0.05 to about 10 mg per day. In one embodiment, a therapeutically or prophylactically effective amount of Compound 1 is from about 0.05 to about 7 mg per day. In one embodiment, a therapeutically or prophylactically effective amount of Compound 1 is from about 0.05 to about 5 mg per day. In one embodiment, a therapeutically or prophylactically effective amount of Compound 1 is from about 0.05 to about 3 mg per day. In one embodiment, a therapeutically or prophylactically effective amount of Compound 1 is from about 0.1 to about 15 mg per day. In one embodiment, a therapeutically or prophylactically effective amount of Compound 1 is from about 0.1 to about 10 mg per day. In one embodiment, a therapeutically or prophylactically effective amount of Compound 1 is from about 0.1 to about 7 mg per day. In one embodiment, a therapeutically or prophylactically effective amount of Compound 1 is from about 0.1 to about 5 mg per day. In one embodiment, a therapeutically or prophylactically effective amount of Compound 1 is from about 0.1 to about 3 mg per day. In one embodiment, a therapeutically or prophylactically effective amount of Compound 1 is from about 0.5 to about 10 mg per day. In one embodiment, a therapeutically or prophylactically effective amount of Compound 1 is from about 0.5 to about 5 mg per day. In one embodiment, a therapeutically or prophylactically effective amount of Compound 1 is from about 0.5 to about 3 mg per day. In one embodiment, a therapeutically or prophylactically effective amount of Compound 1 is from about 0.5 to about 2 mg per day. In one embodiment, a therapeutically or prophylactically effective amount of Compound 1 is from about 0.3 to about 10 mg per day. In one embodiment, a therapeutically or prophylactically effective amount of Compound 1 is from about 0.3 to about 8.5 mg per day. In one embodiment, a therapeutically or prophylactically effective amount of Compound 1 is from about 0.3 to about 8.1 mg per day. In one embodiment, a therapeutically or prophylactically effective amount of Compound 1 is from about 0.6 to about 10 mg per day or from about 0.6 to about 5 mg per day.

In certain embodiments, the therapeutically or prophylactically effective amount is about 0.1, about 0.2, about 0.5, about 1, about 2, about 3, about 4, about 5, about 6, about 7, about 8, about 9, or about 10 mg per day. In some such embodiments, the therapeutically or prophylactically effective amount is about 0.5, about 0.6, about 0.75, about 1, about 2, about 3, about 4, about 5, about 6 or about 7 mg per day. In some such embodiments, the therapeutically or prophylactically effective amount is about 0.6, about 1.2, about 1.8, about 2.4, about 3, about 3.6 mg or about 4.5 mg per day. In certain embodiments, the therapeutically or prophylactically effective amount is about 0.1 mg per day. In certain embodiments, the therapeutically or prophylactically effective amount is about 0.2 mg per day. In certain embodiments, the therapeutically or prophylactically effective amount is about 0.5 mg per day. In certain embodiments, the therapeutically or prophylactically effective amount is about 1 mg per day. In certain embodiments, the therapeutically or prophylactically effective amount is about 2 mg per day. In certain embodiments, the therapeutically or prophylactically effective amount is about 3 mg per day. In certain embodiments, the therapeutically or prophylactically effective amount is about 4 mg per day. In certain embodiments, the therapeutically or prophylactically effective amount is about 4.5 mg per day. In certain embodiments, the therapeutically or prophylactically effective amount is about 5 mg per day. In certain embodiments, the therapeutically or prophylactically effective amount is about 6 mg per day. In certain embodiments, the therapeutically or prophylactically effective amount is about 7 mg per day. In certain embodiments, the therapeutically or prophylactically effective amount is about 8 mg per day. In certain embodiments, the therapeutically or prophylactically effective amount is about 9 mg per day. In certain embodiments, the therapeutically or prophylactically effective amount is about 10 mg per day.

In one embodiment, the recommended daily dose range of Compound 1, for the conditions described herein lie within the range of from about 0.01 mg to about 10 mg per day, preferably given as a single once-a-day dose, or in divided doses throughout a day. In some embodiments, the dosage ranges from about 0.1 mg to about 10 mg per day. In other embodiments, the dosage ranges from about 0.5 to about 5 mg per day. Specific doses per day include 0.1, 0.2, 0.5, 0.6, 1, 1.2, 1.5, 1.8, 2, 2.4, 2.5, 3, 3.5, 3.6, 4, 4.5, 5, 5.5, 6, 6.5, 7, 7.5, 8, 8.5, 9, 9.5 or 10 mg per day. In one embodiment, the dose per day is 0.1 mg per day. In one embodiment, the dose per day is 0.2 mg per day. In one embodiment, the dose per day is 0.5 mg per day. In one embodiment, the dose per day is 0.6 mg per day. In one embodiment, the dose per day is 1 mg per day. In one embodiment, the dose per day is 1.2 mg per day. In one embodiment, the dose per day is 1.5 mg per day. In one embodiment, the dose per day is 1.8 mg per day. In one embodiment, the dose per day is 2 mg per day. In one embodiment, the dose per day is 2.4 mg per day. In one embodiment, the dose per day is 2.5 mg per day. In one embodiment, the dose per day is 3 mg per day. In one embodiment, the dose per day is 3.5 mg per day. In one embodiment, the dose per day is 3.6 mg per day. In one embodiment, the dose per day is 4 mg per day. In one embodiment, the dose per day is 4.5 mg per day. In one embodiment, the dose per day is 5 mg per day. In one embodiment, the dose per day is 5.5 mg per day. In one embodiment, the dose per day is 6 mg per day. In one embodiment, the dose per day is 6.5 mg per day. In one embodiment, the dose per day is 7 mg per day. In one embodiment, the dose per day is 7.5 mg per day. In one embodiment, the dose per day is 8 mg per day. In one embodiment, the dose per day is 8.5 mg per day. In one embodiment, the dose per day is 9 mg per day. In one embodiment, the dose per day is 9.5 mg per day. In one embodiment, the dose per day is 10 mg per day.

In a specific embodiment, the recommended starting dosage may be 0.1, 0.5, 0.6, 0.7, 1, 1.2, 1.5, 1.8, 2, 2.4, 2.5, 3, 3.5, 3.6, 4, 4.5, 5, 5.5, 6, 6.5 or 7 mg per day. In another embodiment, the recommended starting dosage may be 0.1, 0.5, 0.6, 1, 1.2, 1.8, 2, 2.4, 3, 3.6, 4, 4.5, or 5 mg per day. The dose may be escalated to 7, 8, 9 or 10 mg/day.

In certain embodiments, the therapeutically or prophylactically effective amount is from about 0.001 to about 20 mg/kg/day, from about 0.01 to about 15 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, from about 0.01 to about 1 mg/kg/day, or from about 0.01 to about 0.05 mg/kg/day. In certain embodiments, the therapeutically or prophylactically effective amount is from about 0.001 to about 20 mg/kg/day. In certain embodiments, the therapeutically or prophylactically effective amount is from about 0.01 to about 15 mg/kg/day. In certain embodiments, the therapeutically or prophylactically effective amount is from about 0.01 to about 10 mg/kg/day. In certain embodiments, the therapeutically or prophylactically effective amount is from about 0.01 to about 9 mg/kg/day. In certain embodiments, the therapeutically or prophylactically effective amount is 0.01 to about 8 mg/kg/day. In certain embodiments, the therapeutically or prophylactically effective amount is from about 0.01 to about 7 mg/kg/day. In certain embodiments, the therapeutically or prophylactically effective amount is from about 0.01 to about 6 mg/kg/day. In certain embodiments, the therapeutically or prophylactically effective amount is from about 0.01 to about 5 mg/kg/day. In certain embodiments, the therapeutically or prophylactically effective amount is from about 0.01 to about 4 mg/kg/day. In certain embodiments, the therapeutically or prophylactically effective amount is from about 0.01 to about 3 mg/kg/day. In certain embodiments, the therapeutically or prophylactically effective amount is from about 0.01 to about 2 mg/kg/day. In certain embodiments, the therapeutically or prophylactically effective amount is from about 0.01 to about 1 mg/kg/day. In certain embodiments, the therapeutically or prophylactically effective amount is from about 0.01 to about 0.05 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both (see, www.fda.gov/cder/cancer/animalframe.htm). For example, a dose of 1 mg/kg/day for a 65 kg human is approximately equal to 38 mg/m$^2$/day.

In certain embodiments, the amount of Compound 1 administered is sufficient to provide a plasma concentration of the compound at steady state, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM. In certain embodiments, the amount of Compound 1 administered is sufficient to provide a plasma concentration of the compound at steady state, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In other embodiments, the amount of Compound 1 administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM. In other embodiments, the amount of Compound 1 administered is sufficient to provide a plasma concentration of the compound at steady state, ranging from about 5 to about 100 nM. In other embodiments, the amount of Compound 1 administered is sufficient to provide a plasma concentration of the compound at steady state, ranging from about 5 to about 50 nM. In other embodiments, the amount of Compound 1 administered is sufficient to provide a plasma concentration of the compound at steady state, ranging from about 10 to about 100 nM. In other embodiments, the amount of Compound 1 administered is sufficient to provide a plasma concentration of the compound at steady state, ranging from about 10 to about 50 nM. In other embodiments, the amount of Compound 1 administered is sufficient to provide a plasma concentration of the compound at steady state, ranging from about 50 to about 100 nM.

As used herein, the term "plasma concentration at steady state" is the concentration reached after a period of administration of a formulation provided herein. Once steady state is reached, there are minor peaks and troughs on the time dependent curve of the plasma concentration of the solid form.

In certain embodiments, the amount of Compound 1 administered is sufficient to provide a maximum plasma concentration (peak concentration) of the compound, ranging from about 0.001 to about 500 µM, about 0.002 to about 200 µM, about 0.005 to about 100 µM, about 0.01 to about 50 µM, from about 1 to about 50 µM, about 0.02 to about 25

µM, from about 0.05 to about 20 µM, from about 0.1 to about 20 µM, from about 0.5 to about 20 µM, or from about 1 to about 20 µM. In certain embodiments, the amount of Compound 1 administered is sufficient to provide a maximum plasma concentration (peak concentration) of the compound, ranging from about 0.001 to about 500 µM. In certain embodiments, the amount of Compound 1 administered is sufficient to provide a maximum plasma concentration (peak concentration) of the compound, ranging from about 0.002 to about 200 µM. In certain embodiments, the amount of Compound 1 administered is sufficient to provide a maximum plasma concentration (peak concentration) of the compound, ranging from about 0.005 to about 100 µM. In certain embodiments, the amount of Compound 1 administered is sufficient to provide a maximum plasma concentration (peak concentration) of the compound, ranging from about 0.01 to about 50 µM. In certain embodiments, the amount of Compound 1 administered is sufficient to provide a maximum plasma concentration (peak concentration) of the compound, ranging from about 1 to about 50 µM. In certain embodiments, the amount of Compound 1 administered is sufficient to provide a maximum plasma concentration (peak concentration) of the compound, ranging from about 0.02 to about 25 µM. In certain embodiments, the amount of Compound 1 administered is sufficient to provide a maximum plasma concentration (peak concentration) of the compound, ranging from about 0.05 to about 20 µM. In certain embodiments, the amount of Compound 1 administered is sufficient to provide a maximum plasma concentration (peak concentration) of the compound, ranging from about 0.1 to about 20 µM. In certain embodiments, the amount of Compound 1 administered is sufficient to provide a maximum plasma concentration (peak concentration) of the compound, ranging from about 0.5 to about 20 µM. In certain embodiments, the amount of Compound 1 administered is sufficient to provide a maximum plasma concentration (peak concentration) of the compound, ranging from about 1 to about 20 µM.

In certain embodiments, the amount of Compound 1 administered is sufficient to provide a minimum plasma concentration (trough concentration) of the compound, ranging from about 0.001 to about 500 µM, about 0.002 to about 200 µM, about 0.005 to about 100 µM, about 0.01 to about 50 µM, from about 1 to about 50 µM, about 0.01 to about 25 µM, from about 0.01 to about 20 µM, from about 0.02 to about 20 µM, from about 0.02 to about 20 µM, or from about 0.01 to about 20 µM. In certain embodiments, the amount of Compound 1 administered is sufficient to provide a minimum plasma concentration (trough concentration) of the compound, ranging from about 0.001 to about 500 µM. In certain embodiments, the amount of Compound 1 administered is sufficient to provide a minimum plasma concentration (trough concentration) of the compound, ranging from about 0.002 to about 200 µM. In certain embodiments, the amount of Compound 1 administered is sufficient to provide a minimum plasma concentration (trough concentration) of the compound, ranging from about 0.005 to about 100 µM. In certain embodiments, the amount of Compound 1 administered is sufficient to provide a minimum plasma concentration (trough concentration) of the compound, ranging from about 0.01 to about 50 µM. In certain embodiments, the amount of Compound 1 administered is sufficient to provide a minimum plasma concentration (trough concentration) of the compound, ranging from about 1 to about 50 µM, about 0.01 to about 25 µM. In certain embodiments, the amount of Compound 1 administered is sufficient to provide a minimum plasma concentration (trough concentration) of the compound, ranging from about 0.01 to about 20 µM. In certain embodiments, the amount of Compound 1 administered is sufficient to provide a minimum plasma concentration (trough concentration) of the compound, ranging from about 0.02 to about 20 µM. In certain embodiments, the amount of Compound 1 administered is sufficient to provide a minimum plasma concentration (trough concentration) of the compound, ranging from about 0.02 to about 20 µM. In certain embodiments, the amount of Compound 1 administered is sufficient to provide a minimum plasma concentration (trough concentration) of the compound, ranging from about 0.01 to about 20 µM.

In certain embodiments, the amount of Compound 1 administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL. In certain embodiments, the amount of Compound 1 administered is sufficient to provide an area under the curve (AUC) of the compound, ranging from about 100 to about 100,000 ng*hr/mL. In certain embodiments, the amount of Compound 1 administered is sufficient to provide an area under the curve (AUC) of the compound, ranging from about 1,000 to about 50,000 ng*hr/mL. In certain embodiments, the amount of Compound 1 administered is sufficient to provide an area under the curve (AUC) of the compound, ranging from about 5,000 to about 25,000 ng*hr/mL. In certain embodiments, the amount of Compound 1 administered is sufficient to provide an area under the curve (AUC) of the compound, ranging from about 5,000 to about 10,000 ng*hr/mL.

In certain embodiments, the patient to be treated with one of the methods provided herein has not been treated with anti-cancer therapy prior to the administration of Compound 1. In certain embodiments, the patient to be treated with one of the methods provided herein has been treated with anti-cancer therapy prior to the administration of Compound 1. In certain embodiments, the patient to be treated with one of the methods provided herein has developed drug resistance to the anti-cancer therapy.

The methods provided herein encompass treating a patient regardless of patient's age, although some diseases or disorders are more common in certain age groups.

Compound 1 can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound is administered once or more than once each day, for example, for a period of time. The term "continuous" is intended to mean that a therapeutic compound is administered daily for an uninterrupted period of at least 10 days to 52 weeks. The term "intermittent" or "intermittently" as used herein is intended to mean stopping and starting at either regular or irregular intervals. For example, intermittent administration of Compound 1 is administration for one to six days per week, administration in cycles (e.g., daily administration for one to ten consecutive days of a 28 day cycle, then a rest period with no administration for rest of the 28 day cycle; or daily administration for two to eight consecutive weeks, then a rest period with no administration for up to one week), or administration on alternate days. Cycling therapy with Compound 1 is discussed elsewhere herein.

In some embodiments, the frequency of administration is in the range of about a daily dose to about a monthly dose.

In certain embodiments, administration is once a day, twice a day, three times a day, four times a day, once every other day, twice a week, once every week, once every two weeks, once every three weeks, or once every four weeks. In one embodiment, Compound 1 is administered once a day. In another embodiment, Compound 1 is administered twice a day. In yet another embodiment, Compound 1 provided herein is administered three times a day. In still another embodiment, Compound 1 provided herein is administered four times a day. In still another embodiment, Compound 1 provided herein is administered once every other day. In still another embodiment, Compound 1 provided herein is administered twice a week. In still another embodiment, Compound 1 provided herein is administered once every week. In still another embodiment, Compound 1 provided herein is administered once every two weeks. In still another embodiment, Compound 1 provided herein is administered once every three weeks. In still another embodiment, Compound 1 provided herein is administered once every four weeks.

In certain embodiments, Compound 1 is administered once per day from one day to six months, from one week to three months, from one week to four weeks, from one week to three weeks, or from one week to two weeks. In certain embodiments, Compound 1 is administered once per day for one week, two weeks, three weeks, or four weeks. In one embodiment, Compound 1 is administered once per day for 1 day. In one embodiment, Compound 1 is administered once per day for 2 days. In one embodiment, Compound 1 is administered once per day for 3 days. In one embodiment, Compound 1 is administered once per day for 4 days. In one embodiment, Compound 1 is administered once per day for 5 days. In one embodiment, Compound 1 is administered once per day for 6 days. In one embodiment, Compound 1 is administered once per day for one week. In one embodiment, Compound 1 is administered once per day for up to 10 days. In another embodiment, Compound 1 is administered once per day for two weeks. In yet another embodiment, Compound 1 is administered once per day for three weeks. In still another embodiment, Compound 1 is administered once per day for four weeks.

Combination Therapy

In one embodiment, Compound 1 and a glucocorticoid receptor agonist (for example, prednisone, prednisolone, methylpredisolone, hydrocortisone, cortisone, cortisol, triamcinolone, betamethasone or dexamethasone), an IL-1β receptor antagonist (for example, anakinra), or an interleukin-1β blocker (for example, canakinumab), are administered in combination with one or more additional agents selected from JAK inhibitors, FLT3 inhibitors, mTOR inhibitors, spliceosome inhibitors, BET inhibitors, SMG1 inhibitors, ERK inhibitors, LSD1 inhibitors, BH3 mimetics, topoisomerase inhibitors, and RTK inhibitors, and optionally in combination with radiation therapy, blood transfusions, or surgery to a patient with cancer. In one embodiment, Compound 1 and a glucocorticoid receptor agonist (for example, prednisone, prednisolone, methylpredisolone, hydrocortisone, cortisone, cortisol, triamcinolone, betamethasone or dexamethasone), an IL-1β receptor antagonist (for example, anakinra), or an interleukin-1β blocker (for example, canakinumab), are administered in combination with one or more additional agents selected from JAK inhibitors, FLT3 inhibitors, mTOR inhibitors, spliceosome inhibitors, BET inhibitors, SMG1 inhibitors, ERK inhibitors, LSD1 inhibitors, BH3 mimetics, topoisomerase inhibitors, and RTK inhibitors, and optionally in combination with radiation therapy, blood transfusions, or surgery to a patient with cancer. Examples of additional active agents are disclosed herein.

In one embodiment, Compound 1 and a glucocorticoid receptor agonist (for example, prednisone, prednisolone, methylpredisolone, hydrocortisone, cortisone, cortisol, triamcinolone, betamethasone or dexamethasone), an IL-1β receptor antagonist (for example, anakinra), or an interleukin-1β blocker (for example, canakinumab), are administered in combination with one or more additional agents selected from JAK inhibitors, FLT3 inhibitors, mTOR inhibitors, spliceosome inhibitors, BET inhibitors, SMG1 inhibitors, ERK inhibitors, LSD1 inhibitors, BH3 mimetics, topoisomerase inhibitors, and RTK inhibitors, and optionally in combination with radiation therapy, blood transfusions, or surgery to a patient with cancer. Examples of additional active agents are disclosed herein. In one embodiment, Compound 1 and a glucocorticoid receptor agonist (for example, prednisone, prednisolone, methylpredisolone, hydrocortisone, cortisol, triamcinolone, betamethasone or dexamethasone), an IL-1β receptor antagonist (for example, anakinra), or an interleukin-1β blocker (for example, canakinumab), are administered in combination with one or more additional agents selected from JAK inhibitors, FLT3 inhibitors, mTOR inhibitors, spliceosome inhibitors, BET inhibitors, SMG1 inhibitors, ERK inhibitors, LSD1 inhibitors, BH3 mimetics, topoisomerase inhibitors, and RTK inhibitors, and optionally in combination with radiation therapy, blood transfusions, or surgery to a patient with cancer. Examples of additional active agents are disclosed herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. E.g., "in combination" may include administration as a mixture, simultaneous administration using separate formulations, and consecutive administration in any order. "Consecutive" means that a specific time has passed between the administration of the active agents. For example, "consecutive" may be that more than 10 minutes have passed between the administration of the separate active agents. The time period can then be more than 10 minutes, more than 30 minutes, more than 1 hour, more than 3 hours, more than 6 hours or more than 12 hours. E.g., a first therapy (e.g., a prophylactic or therapeutic agent such as Compound 1 provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional therapy (e.g., a prophylactic or therapeutic agent) to the subject. Triple therapy is also contemplated herein.

In one embodiment, administration of Compound 1, a glucocorticoid receptor agonist (for example, prednisone, prednisolone, methylpredisolone, hydrocortisone, cortisol, triamcinolone, betamethasone, or dexamethasone), an IL-1 receptor antagonist (for example, anakinra), or an interleukin-1β blocker (for example, canakinumab), and one or more additional active agents to a patient can occur simultaneously or sequentially by the same or different routes of administration. In one embodiment, administration of Compound 1, a glucocorticoid receptor agonist (for example, prednisone, prednisolone, methylpredisolone, hydrocortisone, cortisone, cortisol, triamcinolone, betamethasone, or dexamethasone), an IL-1 receptor antagonist (for example, anakinra), or an interleukin-1β blocker (for example, canakinumab), and one or more additional active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

In one embodiment, administration of Compound 1 and a glucocorticoid receptor agonist (for example, prednisone, prednisolone, methylpredisolone, hydrocortisone, cortisol, triamcinolone, betamethasone, or dexamethasone), an interleukin-1 receptor antagonist (for example, anakinra), or an interleukin-1β blocker (for example, canakinumab), to a patient can occur simultaneously or sequentially by the same or different routes of administration. In one embodiment, administration of Compound 1 and a glucocorticoid receptor agonist (for example, prednisone, prednisolone, methylpredisolone, hydrocortisone, cortisone, cortisol, triamcinolone, betamethasone, or dexamethasone), an interleukin-1 receptor antagonist (for example, anakinra), or an interleukin-1β blocker (for example, canakinumab), to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of Compound 1 is independent of the route of administration of a glucocorticoid receptor agonist (for example, prednisone, prednisolone, methylpredisolone, hydrocortisone, cortisol, triamcinolone, betamethasone, or dexamethasone), an interleukin-1 receptor antagonist (for example, anakinra), or an interleukin-1β blocker (for example, canakinumab), and an additional therapy. The route of administration of Compound 1 is independent of the route of administration of a glucocorticoid receptor agonist (for example, prednisone, prednisolone, methylpredisolone, hydrocortisone, cortisone, cortisol, triamcinolone, betamethasone, or dexamethasone), an interleukin-1 receptor antagonist (for example, anakinra), or an interleukin-1β blocker (for example, canakinumab), and an additional therapy. Thus, in one embodiment, Compound 1 is administered intravenously, a glucocorticoid receptor agonist (for example, prednisone, prednisolone, methylpredisolone, hydrocortisone, cortisol, triamcinolone, betamethasone, or dexamethasone), an interleukin-1 receptor antagonist (for example, anakinra), or an interleukin-1β blocker (for example, canakinumab), can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form and the additional therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, Compound 1, a glucocorticoid receptor agonist (for example, prednisone, prednisolone, methylpredisolone, hydrocortisone, cortisone, cortisol, triamcinolone, betamethasone, or dexamethasone), an interleukin-1 receptor antagonist (for example, anakinra), or an interleukin-1β blocker (for example, canakinumab), and an additional therapy are administered by the same mode of administration, by IV. In another embodiment, Compound 1 is administered by one mode of administration, e.g., by IV, a glucocorticoid receptor agonist (for example, prednisone, prednisolone, methylpredisolone, hydrocortisone, cortisone, cortisol, triamcinolone, betamethasone, or dexamethasone), is administered by another mode of administration, e.g., orally, and the additional agent (an anti-cancer agent) is administered by another mode of administration, e.g., orally. In another embodiment, Compound 1 is administered by one mode of administration, e.g., by IV, an interleukin-1 receptor antagonist (for example, anakinra), or an interleukin-1β blocker (for example, canakinumab), is administered by another mode of administration, e.g., subcutaneously, and the additional agent (an anti-cancer agent) is administered by another mode of administration, e.g., orally.

In one embodiment, the additional active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the additional active agent will depend on the specific agent used, the type of disease being treated and/or managed, the severity and stage of disease, and the amount of Compound 1 and any optional additional active agents concurrently administered to the patient.

One or more additional active ingredients or agents can be used together with Compound 1 and a glucocorticoid in the methods and compositions provided herein. Additional active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies, particularly, therapeutic antibodies to cancer antigens. Typical large molecule active agents are biological molecules, such as naturally occurring or synthetic or recombinant proteins. Proteins that are particularly useful in the methods and compositions provided herein include proteins that stimulate the survival and/or proliferation of hematopoietic precursor cells and immunologically active poietic cells in vitro or in vivo. Other useful proteins stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

In certain embodiments, GM-CSF, G-CSF, SCF or EPO is administered subcutaneously during about five days in a four or six week cycle in an amount ranging from about 1 to about 750 mg/m²/day, from about 25 to about 500 mg/m²/day, from about 50 to about 250 mg/m²/day, or from about 50 to about 200 mg/m²/day. In certain embodiments, GM-CSF may be administered in an amount of from about 60 to about 500 mcg/m² intravenously over 2 hours or from about 5 to about 12 mcg/m²/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In certain embodiments, EPO may be administered subcutaneously in an amount of 10,000 Unit 3 times per week.

Particular proteins that can be used in the methods and compositions include, but are not limited to: filgrastim, which is sold in the United States under the trade name NEUPOGEN® (Amgen, Thousand Oaks, CA); sargramostim, which is sold in the United States under the trade name LEUKINE® (Immunex, Seattle, WA); and recombinant EPO, which is sold in the United States under the trade name EPOGEN® (Amgen, Thousand Oaks, CA).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; the entireties of which are incorporated herein by reference.

Also provided for use in combination with Compound 1 are native, naturally occurring, and recombinant proteins. Further encompassed are mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with Compound 1 include monoclonal and polyclonal antibodies. Examples of antibodies include, but are not limited to, trastuzumab (HERCEPTIN®), rituximab (RITUXAN®), bevacizumab (AVASTIN™), pertuzumab (OMNITARG™), tositumomab (BEXXAR®), edrecolomab (PANOREX®), and G250. In certain embodiments, Compound 1 is combined with, or used in combination with, anti-TNF-α antibodies, and/or anti-EGFR antibodies, such as, for example, ERBITUX® or panitumumab.

Large molecule active agents may be administered in the form of anti-cancer vaccines. For example, vaccines that secrete, or cause the secretion of, cytokines such as IL-2, G-CSF, and GM-CSF can be used in the methods and pharmaceutical compositions provided. See, e.g., Emens, L. A., et al., *Curr. Opinion Mol. Ther.* 3(1):77-84 (2001).

Additional active agents that are small molecules can also be used to alleviate adverse effects associated with the administration of Compound 1. However, like some large molecules, many are believed to be capable of providing a synergistic effect when administered with (e.g., before, after, or simultaneously) Compound 1. Examples of small molecule additional active agents include, but are not limited to, anti-cancer agents, antibiotics, immunosuppressive agents, and steroids.

In certain embodiments, the additional agent is an HSP inhibitor, a proteasome inhibitor, a FLT3 inhibitor or an mTOR inhibitor. In some embodiments, the mTOR inhibitor is a mTOR kinase inhibitor.

Examples of anti-cancer agents to be used within the methods described herein include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; clofarabine; crisnatol mesylate; cyclophosphamide; Ara-C; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; omacetaxine; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sorafenib; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs to be included within the methods herein include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide;

anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; Ara-C ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anti-cancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (GENASENSE®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosane polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

In certain embodiments, the additional agent is selected from one or more checkpoint inhibitors. In one embodiment, one checkpoint inhibitor is used in combination with Compound 1 in the methods provided herein. In another embodiment, two checkpoint inhibitors are used in combination with Compound 1 in the methods provided herein. In yet another embodiment, three or more checkpoint inhibitors are used in combination with Compound 1 in the methods provided herein.

As used herein, the term "immune checkpoint inhibitor" or "checkpoint inhibitor" refers to molecules that totally or partially reduce, inhibit, interfere with or modulate one or more checkpoint proteins. Without being limited by a particular theory, checkpoint proteins regulate T-cell activation or function. Numerous checkpoint proteins are known, such as CTLA-4 and its ligands CD80 and CD86; and PD-1 with its ligands PD-L1 and PD-L2 (Pardoll, *Nature Reviews Cancer*, 2012, 12, 252-264). These proteins appear responsible for co-stimulatory or inhibitory interactions of T-cell responses. Immune checkpoint proteins appear to regulate and maintain self-tolerance and the duration and amplitude of physiological immune responses. Immune checkpoint inhibitors include antibodies or are derived from antibodies.

In one embodiment, the checkpoint inhibitor is a CTLA-4 inhibitor. In one embodiment, the CTLA-4 inhibitor is an anti-CTLA-4 antibody. Examples of anti-CTLA-4 antibodies include, but are not limited to, those described in U.S. Pat. Nos. 5,811,097; 5,811,097; 5,855,887; 6,051,227; 6,207,157; 6,682,736; 6,984,720; and 7,605,238, all of which are incorporated herein in their entireties. In one embodiment, the anti-CTLA-4 antibody is tremelimumab (also known as ticilimumab or CP-675,206). In another embodiment, the anti-CTLA-4 antibody is ipilimumab (also known as MDX-010 or MDX-101). Ipilimumab is a fully human monoclonal IgG antibody that binds to CTLA-4. Ipilimumab is marketed under the trade name YERVOY®.

In one embodiment, the checkpoint inhibitor is a PD-1/PD-L1 inhibitor. Examples of PD-1/PD-L1 inhibitors include, but are not limited to, those described in U.S. Pat. Nos. 7,488,802; 7,943,743; 8,008,449; 8,168,757; 8,217,149, and PCT Patent Application Publication Nos. WO2003042402, WO2008156712, WO2010089411, WO2010036959, WO2011066342, WO2011159877, WO2011082400, and WO2011161699, all of which are incorporated herein in their entireties.

In one embodiment, the checkpoint inhibitor is a PD-1 inhibitor. In one embodiment, the PD-1 inhibitor is an anti-PD-1 antibody. In one embodiment, the anti-PD-1 antibody is BGB-A317, nivolumab (also known as ONO-4538, BMS-936558, or MDX1106) or pembrolizumab (also known as MK-3475, SCH 900475, or lambrolizumab). In one embodiment, the anti-PD-1 antibody is nivolumab. Nivolumab is a human IgG4 anti-PD-1 monoclonal antibody, and is marketed under the trade name OPDIVO®. In another embodiment, the anti-PD-1 antibody is pembrolizumab. Pembrolizumab is a humanized monoclonal IgG4 antibody and is marketed under the trade name KEYTRUIDA®. In yet another embodiment, the anti-PD-1 antibody is CT-011, a humanized antibody. CT-011 administered alone has failed to show response in treating acute myeloid leukemia (AML) at relapse. In yet another embodiment, the anti-PD-1 antibody is AMP-224, a fusion protein. In another embodiment, the PD-1 antibody is BGB-A317. BGB-A317 is a monoclonal antibody in which the ability to bind Fc gamma receptor I is specifically engineered out, and which has a unique binding signature to PD-1 with high affinity and superior target specificity.

In one embodiment, the checkpoint inhibitor is a PD-L1 inhibitor. In one embodiment, the PD-L1 inhibitor is an anti-PD-L1 antibody. In one embodiment, the anti-PD-L1 antibody is MEDI4736 (durvalumab). In another embodiment, the anti-PD-L1 antibody is BMS-936559 (also known as MDX-1105-01). In yet another embodiment, the PD-L1 inhibitor is atezolizumab (also known as MPDL3280A, and TECENTRIQ®).

In one embodiment, the checkpoint inhibitor is a PD-L2 inhibitor. In one embodiment, the PD-L2 inhibitor is an anti-PD-L2 antibody. In one embodiment, the anti-PD-L2 antibody is rHIgM12B7A.

In one embodiment, the checkpoint inhibitor is a lymphocyte activation gene-3 (LAG-3) inhibitor. In one embodiment, the LAG-3 inhibitor is IMP321, a soluble Ig fusion protein (Brignone et al., *J. Immunol.*, 2007, 179, 4202-4211). In another embodiment, the LAG-3 inhibitor is BMS-986016.

In one embodiment, the checkpoint inhibitor is a B7 inhibitor. In one embodiment, the B7 inhibitor is a B7-H3 inhibitor or a B7-H4 inhibitor. In one embodiment, the B7-H3 inhibitor is MGA271, an anti-B7-H3 antibody (Loo et al., *Clin. Cancer Res.*, 2012, 3834).

In one embodiment, the checkpoint inhibitor is a TIM3 (T-cell immunoglobulin domain and mucin domain 3) inhibitor (Fourcade et al., *J. Exp. Med.*, 2010, 207, 2175-86; Sakuishi et al., *J. Exp. Med.*, 2010, 207, 2187-94).

In one embodiment, the checkpoint inhibitor is an OX40 (CD134) agonist. In one embodiment, the checkpoint inhibitor is an anti-OX40 antibody. In one embodiment, the anti-OX40 antibody is anti-OX-40. In another embodiment, the anti-OX40 antibody is MEDI6469.

In one embodiment, the checkpoint inhibitor is a GITR agonist. In one embodiment, the checkpoint inhibitor is an anti-GITR antibody. In one embodiment, the anti-GITR antibody is TRX518.

In one embodiment, the checkpoint inhibitor is a CD137 agonist. In one embodiment, the checkpoint inhibitor is an anti-CD137 antibody. In one embodiment, the anti-CD137 antibody is urelumab. In another embodiment, the anti-CD137 antibody is PF-05082566.

In one embodiment, the checkpoint inhibitor is a CD40 agonist. In one embodiment, the checkpoint inhibitor is an anti-CD40 antibody. In one embodiment, the anti-CD40 antibody is CF-870,893.

In one embodiment, the checkpoint inhibitor is recombinant human interleukin-15 (rhIL-15).

In one embodiment, the checkpoint inhibitor is an IDO inhibitor. In one embodiment, the IDO inhibitor is INCB024360. In another embodiment, the IDO inhibitor is indoximod.

In certain embodiments, the combination therapies provided herein include two or more of the checkpoint inhibitors described herein (including checkpoint inhibitors of the same or different class). Moreover, the combination therapies described herein can be used in combination with additional active agents as described herein where appropriate for treating diseases described herein and understood in the art.

In certain embodiments, Compound 1 can be used in combination with one or more immune cells expressing one or more chimeric antigen receptors (CARs) on their surface (e.g., a modified immune cell). Generally, CARs comprise an extracellular domain from a first protein e.g., an antigen-binding protein), a transmembrane domain, and an intracellular signaling domain. In certain embodiments, once the extracellular domain binds to a target protein such as a tumor-associated antigen (TAA) or tumor-specific antigen (TSA), a signal is generated via the intracellular signaling domain that activates the immune cell, e.g., to target and kill a cell expressing the target protein.

Extracellular domains: The extracellular domains of the CARs bind to an antigen of interest. In certain embodiments, the extracellular domain of the CAR comprises a receptor, or a portion of a receptor, that binds to said antigen. In certain embodiments, the extracellular domain comprises, or is, an antibody or an antigen-binding portion thereof. In specific embodiments, the extracellular domain comprises, or is, a single chain Fv (scFv) domain. The single-chain Fv domain can comprise, for example, a $V_L$ linked to $V_H$ by a flexible linker, wherein said $V_L$ and $V_H$ are from an antibody that binds said antigen.

In certain embodiments, the antigen recognized by the extracellular domain of a polypeptide described herein is a tumor-associated antigen (TAA) or a tumor-specific antigen (TSA). In various specific embodiments, the tumor-associated antigen or tumor-specific antigen is, without limitation, Her2, prostate stem cell antigen (PSCA), alpha-fetoprotein (AFP), carcinoembryonic antigen (CEA), cancer antigen-125 (CA-125), CA19-9, calretinin, MUC-1, B cell maturation antigen (BCMA), epithelial membrane protein (EMA), epithelial tumor antigen (ETA), tyrosinase, melanoma-associated antigen (MAGE), CD19, CD22, CD27, CD30, CD34, CD45, CD70, CD99, CD117, EGFRvIII (epidermal growth factor variant III), mesothelin, PAP (prostatic acid phosphatase), prostein, TARP (T cell receptor gamma alternate reading frame protein), Trp-p8, STEAPI (six-transmembrane epithelial antigen of the prostate 1), chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-I), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein. In certain other embodiments, the TAA or TSA recognized by the extracellular domain of a CAR is integrin αvβ3 (CD61), galactin, or Ral-B.

In certain embodiments, the TAA or TSA recognized by the extracellular domain of a CAR is a cancer/testis (CT) antigen, e.g., BAGE, CAGE, CTAGE, FATE, GAGE, HCA661, HOM-TES-85, MAGEA, MAGEB, MAGEC, NA88, NY-ESO-1, NY-SAR-35, OY-TES-1, SPANXBI, SPA17, SSX, SYCPI, or TPTE.

In certain other embodiments, the TAA or TSA recognized by the extracellular domain of a CAR is a carbohydrate or ganglioside, e.g., fuc-GMI, GM2 (oncofetal antigen-immunogenic-1; OFA-I-1); GD2 (OFA-I-2), GM3, GD3, and the like.

In certain other embodiments, the TAA or TSA recognized by the extracellular domain of a CAR is alpha-actinin-4, Bage-1, BCR-ABL, Bcr-Abl fusion protein, beta-catenin, CA 125, CA 15-3 (CA 27.29\BCAA), CA 195, CA 242, CA-50, CAM43, Casp-8, cdc27, cdk4, cdkn2a, CEA, coa-1, dek-can fusion protein, EBNA, EF2, Epstein Barr virus antigens, ETV6-AML1 fusion protein, HLA-A2, HLA-All, hsp70-2, KIAA0205, Mart2, Mum-1, 2, and 3, neo-PAP, myosin class I, OS-9, pml-RARa fusion protein, PTPRK, K-ras, N-ras, triosephosphate isomerase, Gage 3,4,5,6,7, GnTV, Herv-K-mel, Lage-1, NA-88, NY-Eso-1/Lage-2, SP17, SSX-2, TRP2-Int2, gp100 (Pme117), tyrosinase, TRP-1, TRP-2, MAGE-1, MAGE-3, RAGE, GAGE-1, GAGE-2, p15(58), RAGE, SCP-1, Horn/Mel-40, PRAME, p53, HRas, HER-2/neu, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, 13-Catenin, Mum-1, p16, TAGE, PSMA, CT7, telomerase, 43-9F, 5T4, 791Tgp72, 13HCG, BCA225, BTAA, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90, TAAL6, TAG72, TLP, or TPS.

In various specific embodiments, the tumor-associated antigen or tumor-specific antigen is an AML-related tumor antigen, as described in S. Anguille et al, *Leukemia* (2012), 26, 2186-2196.

Other tumor-associated and tumor-specific antigens are known to those in the art.

Receptors, antibodies, and scFvs that bind to TSAs and TAAs, useful in constructing chimeric antigen receptors, are known in the art, as are nucleotide sequences that encode them.

In certain specific embodiments, the antigen recognized by the extracellular domain of a chimeric antigen receptor is an antigen not generally considered to be a TSA or a TAA, but which is nevertheless associated with tumor cells, or damage caused by a tumor. In certain embodiments, for example, the antigen is, e.g., a growth factor, cytokine or interleukin, e.g., a growth factor, cytokine, or interleukin associated with angiogenesis or vasculogenesis. Such growth factors, cytokines, or interleukins can include, e.g., vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8). Tumors can also create a hypoxic environment local to the tumor. As such, in other specific embodiments, the antigen is a hypoxia-associated factor, e.g., HIF-1α, HIF-1β, HIF-2α, HIF-2β, HIF-3α, or HIF-3β. Tumors can also cause localized damage to normal tissue, causing the release of molecules known as damage associated molecular pattern molecules (DAMPs; also known as alarmins). In certain other specific embodiments, therefore, the antigen is a DAMP, e.g., a heat shock protein, chromatin-associated protein high mobility group box 1 (HMGB 1), S100A8 (MRP8, calgranulin A), S100A9 (MRP14, calgranulin B), serum amyloid A (SAA), or can be a deoxyribonucleic acid, adenosine triphosphate, uric acid, or heparin sulfate.

Transmembrane domain: In certain embodiments, the extracellular domain of the CAR is joined to the transmembrane domain of the polypeptide by a linker, spacer or hinge polypeptide sequence, e.g., a sequence from CD28 or a sequence from CTLA4. The transmembrane domain can be obtained or derived from the transmembrane domain of any transmembrane protein, and can include all or a portion of such transmembrane domain. In specific embodiments, the transmembrane domain can be obtained or derived from, e.g., CD8, CD16, a cytokine receptor, and interleukin receptor, or a growth factor receptor, or the like.

Intracellular signaling domains: In certain embodiments, the intracellular domain of a CAR is or comprises an intracellular domain or motif of a protein that is expressed on the surface of T cells and triggers activation and/or proliferation of said T cells. Such a domain or motif is able to transmit a primary antigen-binding signal that is necessary for the activation of a T lymphocyte in response to the antigen's binding to the CAR's extracellular portion. Typically, this domain or motif comprises, or is, an ITAM (immunoreceptor tyrosine-based activation motif). ITAM-containing polypeptides suitable for CARs include, for example, the zeta CD3 chain (CD3) or ITAM-containing portions thereof. In a specific embodiment, the intracellular domain is a CD3 intracellular signaling domain. In other specific embodiments, the intracellular domain is from a lymphocyte receptor chain, a TCR/CD3 complex protein, an Fe receptor subunit or an IL-2 receptor subunit. In certain embodiments, the CAR additionally comprises one or more co-stimulatory domains or motifs, e.g., as part of the intracellular domain of the polypeptide. The one or more co-stimulatory domains or motifs can be, or can comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence, or other costimulatory domain or motif, or any combination thereof.

The CAR may also comprise a T cell survival motif. The T cell survival motif can be any polypeptide sequence or motif that facilitates the survival of the T lymphocyte after stimulation by an antigen. In certain embodiments, the T cell survival motif is, or is derived from, CD3, CD28, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor β (TGFβ) receptor.

The modified immune cells expressing the CARs can be, e.g., T lymphocytes (T cells, e.g., CD4+ T cells or CD8+ T cells), cytotoxic lymphocytes (CTLs) or natural killer (NK) cells. T lymphocytes used in the compositions and methods provided herein may be naïve T lymphocytes or MHC-restricted T lymphocytes. In certain embodiments, the T lymphocytes are tumor infiltrating lymphocytes (TILs). In certain embodiments, the T lymphocytes have been isolated from a tumor biopsy, or have been expanded from T lymphocytes isolated from a tumor biopsy. In certain other embodiments, the T cells have been isolated from, or are expanded from T lymphocytes isolated from, peripheral blood, cord blood, or lymph. Immune cells to be used to generate modified immune cells expressing a CAR can be isolated using art-accepted, routine methods, e.g., blood collection followed by apheresis and optionally antibody-mediated cell isolation or sorting.

The modified immune cells are preferably autologous to an individual to whom the modified immune cells are to be administered. In certain other embodiments, the modified immune cells are allogeneic to an individual to whom the modified immune cells are to be administered. Where allogeneic T lymphocytes or NK cells are used to prepare modified T lymphocytes, it is preferable to select T lymphocytes or NK cells that will reduce the possibility of graft-versus-host disease (GVHD) in the individual. For example, in certain embodiments, virus-specific T lymphocytes are selected for preparation of modified T lymphocytes; such lymphocytes will be expected to have a greatly reduced native capacity to bind to, and thus become activated by, any recipient antigens. In certain embodiments, recipient-mediated rejection of allogeneic T lymphocytes can be reduced by co-administration to the host of one or more immunosuppressive agents, e.g., cyclosporine, tacrolimus, sirolimus, cyclophosphamide, or the like.

T lymphocytes, e.g., unmodified T lymphocytes, or T lymphocytes expressing CD3 and CD28, or comprising a polypeptide comprising a CD3ζ signaling domain and a CD28 co-stimulatory domain, can be expanded using antibodies to CD3 and CD28, e.g., antibodies attached to beads; see, e.g., U.S. Pat. Nos. 5,948,893; 6,534,055; 6,352,694; 6,692,964; 6,887,466; and 6,905,681.

The modified immune cells, e.g., modified T lymphocytes, can optionally comprise a "suicide gene" or "safety switch" that enables killing of substantially all of the modified immune cells when desired. For example, the modified T lymphocytes, in certain embodiments, can comprise an HSV thymidine kinase gene (HSV-TK), which causes death of the modified T lymphocytes upon contact with gancyclovir. In another embodiment, the modified T lymphocytes comprise an inducible caspase, e.g., an inducible caspase 9 (icaspase9), e.g., a fusion protein between caspase 9 and human FK506 binding protein allowing for dimerization using a specific small molecule pharmaceutical. See Straathof et al., *Blood* 105(11):4247-4254 (2005).

Specific additional active agents useful in the methods include, but are not limited to, rituximab, oblimersen (GENASENSE®), remicade, docetaxel, celecoxib, melphalan, steroids, gemcitabine, cisplatinum, temozolomide, etoposide, cyclophosphamide, temodar, carboplatin, procarbazine, GLIADEL®, tamoxifen, topotecan, methotrexate, ARISA®, taxol, taxotere, fluorouracil, leucovorin, irinotecan, xeloda, interferon alpha, pegylated interferon alpha (e.g., PEG INTRON-A), capecitabine, cisplatin, thiotepa, fludarabine, carboplatin, liposomal daunorubicin, Ara-C, doxetaxol, paclitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (DOXIL®), paclitaxel, ganciclovir, adriamycin, estramustine sodium phosphate (EMCYT®), sulindac, and etoposide.

In certain embodiments of the methods provided herein, use of an additional active agent in combination with Compound 1 may be modified or delayed during or shortly following administration of Compound 1 provided herein, as deemed appropriate by the practitioner of skill in the art. In certain embodiments, subjects being administered Compound 1, alone or in combination with other therapies may receive supportive care including antiemetics, myeloid growth factors, and transfusions of platelets, when appropriate. In some embodiments, subjects being administered Compound 1 may be administered a growth factor as an additional active agent according to the judgment of the practitioner of skill in the art. In some embodiments, provided is administration of Compound 1 in combination with erythropoietin or darbepoetin (Aranesp).

In one aspect, the methods provided herein comprise administering Compound 1 and a glucocorticoid receptor agonist, an interleukin-1 receptor antagonist, or an interleukin-1β blocker in combination with gemcitabine, cisplatinum, 5-fluorouracil, mitomycin, methotrexate, vinblastine, doxorubicin, carboplatin, thiotepa, paclitaxel, docetaxel, atezolizumab, avelumab, durvalumab, KEYTRUDA® (pembrolizumab) and/or nivolumab in patients having locally advanced or metastatic transitional cell bladder cancer.

In one aspect, the methods provided herein comprise administering Compound 1 and a glucocorticoid receptor agonist, an interleukin-1 receptor antagonist, or an interleukin-1β blocker in combination with an additional active ingredient as follows: temozolomide to pediatric patients with relapsed or progressive brain tumors or recurrent neuroblastoma; celecoxib, etoposide and cyclophosphamide for relapsed or progressive CNS cancer; temodar to patients with recurrent or progressive meningioma, malignant meningioma, hemangiopericytoma, multiple brain metastases, relapsed brain tumors, or newly diagnosed glioblastoma multiforms; irinotecan to patients with recurrent glioblastoma; carboplatin to pediatric patients with brain stem glioma; procarbazine to pediatric patients with progressive malignant gliomas; cyclophosphamide to patients with poor prognosis malignant brain tumors, newly diagnosed or recurrent glioblastoma multiforms; GLIADEL® for high grade recurrent malignant gliomas; temozolomide and tamoxifen for anaplastic astrocytoma; or topotecan for gliomas, glioblastoma, anaplastic astrocytoma or anaplastic oligodendroglioma.

In one aspect, the methods provided herein comprise administering Compound 1 and a glucocorticoid receptor agonist, an interleukin-1 receptor antagonist, or an interleukin-1β blocker, in combination with methotrexate, cyclophosphamide, capecitabine, 5-fluorouracil, taxane, temsirolimus, ABRAXANE® (paclitaxel protein-bound particles for injectable suspension) (albumin-bound), lapatinib, herceptin, pamidronate disodium, eribulin mesylate, everolimus, gemcitabine, palbociclib, ixabepilone, kadcyla, pertuzumab, theotepa, anastrozole, docetaxel, doxorubicin hydrochloride, epirubicin hydrochloride, toremifene, fulvestrant, goserelin acetate, ribociclib, megestrol acetate, vinblastin, aromatase inhibitors, such as letrozole, exemestane, selective estrogen modulators, estrogen receptor antagonists, anthracyclines, emtansine, and/or pexidartinib to patients with metastatic breast cancer.

In one aspect, the methods provided herein comprise administering Compound 1 and a glucocorticoid receptor agonist, an interleukin-1 receptor antagonist, or an interleukin-1β blocker in combination with at least one of everolimus, avelumab, sunitinib, nexavar, leucovorin, oxaliplatin, temozolomide, capecitabine, bevacizumab, doxorubicin (Adriamycin), fluorouracil (Adrucil, 5-fluorouracil), streptozocin (Zanosar), dacarbazine, sandostatin, lanreotide, and/or pasireotide to patients with neuroendocrine tumors.

In one aspect, the methods provided herein comprise administering Compound 1 and a glucocorticoid receptor agonist, an interleukin-1 receptor antagonist, or an interleukin-1β blocker in combination with methotrexate, gemcitabine, cisplatin, cetuximab, 5-fluorouracil, bleomycin, docetaxel, carboplatin, hydroxyurea, pembrolizumab and/or nivolumab to patients with recurrent or metastatic head or neck cancer.

In one aspect, the methods provided herein comprise administering Compound 1 and a glucocorticoid receptor agonist, an interleukin-1 receptor antagonist, or an interleukin-1β blocker in combination with gemcitabine, ABRAXANE®, 5-fluorouracil, afinitor, irinotecan, mitomycin C, sunitinib, sunitinibmalate, and/or tarceva to patients with pancreatic cancer.

In one aspect, the methods provided herein comprise administering Compound 1 and a glucocorticoid receptor antagonist, an interleukin-1 receptor antagonist, or an interleukin-1β blocker in combination with ARISA®, avastain, oxaliplatin, 5-fluorouracil, irinotecan, capecitabine, cetuximab, ramucirumab, panitumumab, bevacizumab, leucovorin calcium, lonsurf, regorafenib, ziv-aflibercept, taxol, and/or taxotere to patients with colon or rectal cancer.

In one aspect, the methods provided herein comprise administering Compound 1 and a glucocorticoid receptor agonist, an interleukin-1 receptor antagonist, or an interleukin-1β blocker in combination with capecitabine and/or vemurafenib to patients with refractory colorectal cancer, or patients who fail first line therapy or have poor performance in colon or rectal adenocarcinoma.

In one aspect, the methods provided herein comprise administering Compound 1 and a glucocorticoid receptor agonist, an interleukin-1 receptor antagonist, or an interleukin-1β blocker in combination with fluorouracil, leucovorin, and/or irinotecan to patients with colorectal cancer, including stage 3 and stage 4, or to patients who have been previously treated for metastatic colorectal cancer.

In one aspect, the methods provided herein comprise administering Compound 1 and a glucocorticoid receptor agonist, an interleukin-1 receptor antagonist, or an interleukin-1β blocker in combination with capecitabine, xeloda, and/or irinotecan to patients with refractory colorectal cancer or to patients with unresectable or metastatic colorectal carcinoma.

In one aspect, the methods provided herein comprise administering Compound 1 and a glucocorticoid receptor agonist, an interleukin-1 receptor antagonist, or an interleukin-1β blocker in combination with interferon alpha or capecitabine to patients with unresectable or metastatic hepatocellular carcinoma; or with cisplatin and thiotepa, or with sorafenib tosylate to patients with primary or metastatic liver cancer.

In one aspect, the methods provided herein comprise administering Compound 1 and a glucocorticoid receptor agonist, an interleukin-1 receptor antagonist, or an interleukin-1β blocker in combination with doxorubicin, paclitaxel, vinblastine, pegylated interferon alpha and/or recombinant interferon alpha-2b to patients with Kaposi's sarcoma.

In one aspect, the methods provided herein comprise administering Compound 1 and a glucocorticoid receptor agonist, an interleukin-1 receptor antagonist, or an interleukin-1β blocker in combination with at least one of enasidenib, arsenic trioxide, fludarabine, carboplatin, daunorubicin, cyclophosphamide, cytarabine, doxorubicin, idarubicin, mitoxantrone hydrochloride, thioguanine, vincristine, midostaurin and/or topotecan to patients with acute myeloid leukemia, including refractory or relapsed or high-risk acute myeloid leukemia.

In one aspect, the methods provided herein comprise administering Compound 1 and a glucocorticoid receptor agonist, an interleukin-1 receptor antagonist, or an interleukin-1β blocker in combination with at least one of enasidenib, liposomal daunorubicin, topotecan and/or cytarabine to patients with unfavorable karyotype acute myeloblastic leukemia.

In one aspect, the methods provided herein comprise administering Compound 1 and a glucocorticoid receptor agonist, an interleukin-1 receptor antagonist, or an interleukin-1β blocker in combination with an IDH2 inhibitor to a patient having leukemia, wherein the leukemia is characterized by the presence of a mutant allele of IDH2. Exemplary IDH2 inhibitors are disclosed in U.S. Pat. Nos. 9,732,062; 9,724,350; 9,738,625; and 9,579,324; and US Publication Nos. 2016-0159771 and US 2016-0158230 A1. In one aspect, the methods provided herein comprise administering Compound 1 and dexamethasone in combination with enasidenib to a patient having leukemia, wherein the leukemia is characterized by the presence of a mutant allele of IDH2. In certain embodiments, the combination of Compound 1 and an IDH2 inhibitor increases differentiated cells (CD34-/CD38) and erythroblasts in a patient having acute myeloid leukemia, wherein the acute myeloid leukemia is characterized by the presence of IDH2 R140Q. In certain embodiments, the combination of Compound 1 and an IDH2 inhibitor reduces progenitor cells (CD34+/CD38+) and HSC in a patient having acute myeloid leukemia, wherein the acute myeloid leukemia is characterized by the presence of IDH2 R140Q.

In one aspect, the methods provided herein comprise administering Compound 1 and a glucocorticoid receptor agonist, an interleukin-1 receptor antagonist, or an interleukin-1β blocker in combination with enasidenib to a patient having acute myeloid leukemia, wherein the acute myeloid leukemia is characterized by the presence of a mutant allele of IDH2. In one embodiment, the mutant allele of IDH2 is IDH2 R140Q or R172K.

In one aspect, the methods provided herein comprise administering Compound 1 and a glucocorticoid receptor agonist, an interleukin-1 receptor antagonist, or an interleukin-1β blocker in combination with enasidenib to a patient having leukemia, wherein the leukemia is characterized by the presence of a mutant allele of IDH2. In one aspect, the methods provided herein comprise administering Compound 1 and dexamethasone in combination with with enasidenib to a patient having acute myeloid leukemia, wherein the acute myeloid leukemia is characterized by the presence of a mutant allele of IDH2. In one embodiment, the mutant allele of IDH2 is IDH2 R140Q or R172K.

In one aspect, the methods provided herein comprise administering Compound 1 and a glucocorticoid receptor agonist, an interleukin-1 receptor antagonist, or an interleukin-1β blocker in combination with methotrexate, mechlorethamine hydrochloride, afatinib dimaleate, pemetrexed, bevacizumab, carboplatin, cisplatin, ceritinib, crizotinib, ramucirumab, pembrolizumab, docetaxel, vinorelbine tartrate, gemcitabine, ABRAXANE®, erlotinib, geftinib, irinotecan, everolimus, alectinib, brigatinib, nivolumab, osimertinib, atezolizumab, necitumumab and/or to patients with non-small cell lung cancer.

In one aspect, the methods provided herein comprise administering Compound 1 and a glucocorticoid receptor agonist, an interleukin-1 receptor antagonist, or an interleukin-1β blocker in combination with carboplatin and irinotecan to patients with non-small cell lung cancer.

In one aspect, the methods provided herein comprise administering Compound 1 and dexam a glucocorticoid receptor agonist, an interleukin-1 receptor antagonist, or an interleukin-1β blocker ethasone in combination with doxetaxol to patients with non-small cell lung cancer who have been previously treated with carbo/etoposide and radiotherapy.

In one aspect, the methods provided herein comprise administering Compound 1 and a glucocorticoid receptor agonist, an interleukin-1 receptor antagonist, or an interleukin-1β blocker in combination with carboplatin and/or taxotere, or in combination with carboplatin, paclitaxel and/or thoracic radiotherapy to patients with non-small cell lung cancer.

In one aspect, the methods provided herein comprise administering Compound 1 and a glucocorticoid receptor agonist, an interleukin-1 receptor antagonist, or an interleukin-1β blocker in combination with taxotere to patients with stage IIIB or IV non-small cell lung cancer.

In one aspect, the methods provided herein comprise administering Compound 1 and a glucocorticoid receptor agonist, an interleukin-1 receptor antagonist, or an interleukin-1β blocker in combination with oblimersen (GENASENSE®), methotrexate, mechlorethamine hydrochloride, etoposide, topotecan and/or doxorubicin to patients with small cell lung cancer.

In one aspect, the methods provided herein comprise administering Compound 1 and a glucocorticoid receptor agonist, an interleukin-1 receptor antagonist, or an interleukin-1β blocker in combination with venetoclax, ABT-737 (Abbott Laboratories) and/or obatoclax (GX15-070) to patients with lymphoma and other blood cancers.

In one aspect, the methods provided herein comprise administering Compound 1 and a glucocorticoid receptor agonist, an interleukin-1 receptor antagonist, or an interleukin-1β blocker in combination with an additional active ingredient such as vinblastine or fludarabine adcetris, ambochlorin, becenum, bleomycin, brentuximab vedotin, carmustinem chlorambucil, cyclophosphamide, dacarbazine, doxorubicin, lomustine, matulane, mechlorethamine hydrochloride, prednisone, procarbazine hydrochloride, vincristine, methotrexate, nelarabin, belinostat, bendamustine HCl, tositumomab, and iodine 131 tositumomab, denileukin diftitox, pralatrexate, prelixafor, obinutuzumab, ibritumomab, tiuxefan, ibritinib, idelasib, INTRON® A, romidepsin, lenalidomide, rituximab, and/or vorinostat to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In one aspect, the methods provided herein comprise administering Compound 1 and a glucocorticoid receptor agonist, an interleukin-1 receptor antagonist, or an interleukin-1β blocker in combination with taxotere, dabrafenib, imlygic, ipilimumab, pembrolizumab, nivolumab, trametinib, vemurafenib, talimogene laherparepvec, IL-2, IFN, GM-CSF, and/or dacarbazine, aldesleukin, cobimetinib, INTRON A®, peginterferon Alfa-2b, and/or trametinib to patients with various types or stages of melanoma.

In one aspect, the methods provided herein comprise administering Compound 1 and a glucocorticoid receptor agonist, an interleukin-1 receptor antagonist, or an interleukin-1β blocker in combination with vinorelbine or pemetrexed disodium to patients with malignant mesothelioma, or stage IIIB non-small cell lung cancer with pleural implants or malignant pleural effusion mesothelioma syndrome.

In one aspect, the methods provided herein comprise administering Compound 1 and a glucocorticoid receptor agonist, an interleukin-1 receptor antagonist, or an interleukin-1β blocker in combination with zoledronic acid, palmitronate, GM-CSF, biaxin, vinblastine, melphalan, busulphan, cyclophosphamide, IFN, prednisone, bisphosphonate, celecoxib, arsenic trioxide, PEG INTRON-A, vincristine, becenum, bortezomib, carfilzomib, doxorubicin, panobinostat, lenalidomide, pomalidomide, thalidomide, mozobil, carmustine, daratumumab, elotuzumab, ixazomib citrate, plerixafor or a combination thereof to patients with various types or stages of multiple myeloma.

In one aspect, the methods provided herein comprise administering Compound 1 and a glucocorticoid receptor agonist, an interleukin-1 receptor antagonist, or an interleukin-1β blocker in combination with chimeric antigen receptor (CAR) T-cells to patients with various types or stages of multiple myeloma. In certain embodiments the CAR T cell in the combination targets B cell maturation antigen (BCMA), and in more specific embodiments, the CAR T cell is bb2121 or bb21217. In some embodiments, the CAR T cell is JCARH125.

In certain embodiments, the methods provided herein comprise administering Compound 1 and d a glucocorticoid receptor agonist, an interleukin-1 receptor antagonist, or an interleukin-1β blocker examethasone in combination with doxorubicin (DOXIL®) and/or vincristine to patients with relapsed or refractory multiple myeloma.

In certain embodiments, the methods provided herein comprise administering Compound 1 and a glucocorticoid receptor agonist, an interleukin-1 receptor antagonist, or an interleukin-1β blocker in combination with taxol, carboplatin, doxorubicin, gemcitabine, cisplatin, xeloda, paclitaxel, avastin, cyclophosphamide, topotecan, olaparib, thiotepa, melphalan, niraparib tosylate monohydrate, rubraca or a combination thereof to patients with various types or stages of ovarian cancer such as peritoneal carcinoma, papillary serous carcinoma, refractory ovarian cancer or recurrent ovarian cancer.

In certain embodiments, the methods provided herein comprise administering Compound 1 and a glucocorticoid receptor agonist, an interleukin-1 receptor antagonist, or an interleukin-1β blocker in combination with xeloda, 5 FU/LV, gemcitabine, irinotecan plus gemcitabine, cyclophosphamide, vincristine, GM-CSF, celecoxib, taxotere, ganciclovir, paclitaxel, adriamycin, docetaxel, estramustine, Emcyt, denderon, zytiga, bicalutamide, cabazitaxel, degarelix, enzalutamide, zoladex, leuprolide acetate, mitoxantrone hydrochloride, prednisone, sipuleucel-T, radium 223 dichloride, or a combination thereof to patients with various types or stages of prostate cancer.

In certain embodiments, the methods provided herein comprise administering Compound 1 and a glucocorticoid receptor agonist, an interleukin-1 receptor antagonist, or an interleukin-1β blocker in combination with capecitabine, IFN, tamoxifen, IL-2, GM-CSF, CELEBREX flutamide, goserelin acetate, nilutamide or a combination thereof to patients with various types or stages of renal cell cancer.

In certain embodiments, the methods provided herein comprise administering Compound 1 and a glucocorticoid receptor agonist, an interleukin-1 receptor antagonist, or an interleukin-1β blocker in combination with IFN, dactinomycin, doxorubicin, imatinib mesylate, pazopanib, hydrochloride, trabectedin, eribulin mesylate, olaratumab, a COX-2 inhibitor such as celecoxib, and/or sulindac to patients with various types or stages of gynecologic, uterus or soft tissue sarcoma cancer.

In one aspect, the methods provided herein comprise administering Compound 1 and a glucocorticoid receptor agonist, an interleukin-1 receptor antagonist, or an interleukin-1β blocker in combination with celecoxib, etoposide, cyclophosphamide, docetaxel, apecitabine, IFN, tamoxifen, IL-2, GM-CSF, or a combination thereof to patients with various types or stages of solid tumors.

In one aspect, the methods provided herein comprise administering Compound 1 and a glucocorticoid receptor agonist, an interleukin-1 receptor antagonist, or an interleukin-1β blocker in combination with celebrex, etoposide, cyclophosphamide, docetaxel, apecitabine, IFN, tamoxifen, IL-2, GM-CSF, or a combination thereof to patients with scleroderma or cutaneous vasculitis.

In one aspect, the methods provided herein comprise administering Compound 1 and a glucocorticoid receptor agonist, an interleukin-1 receptor antagonist, or an interleukin-1β blocker in combination with azacitidine, cytarabine, daunorubicin, decitabine, idarubicin, lenalidomide, enasidenib, or a combination thereof to patients with MDS.

In one aspect, the methods provided herein comprise administering Compound 1 and a glucocorticoid receptor agonist, an interleukin-1 receptor antagonist, or an interleukin-1β blocker to patients with hematological cancer in combination with one or more additional agents selected from JAK inhibitors, FLT3 inhibitors, mTOR inhibitors, spliceosome inhibitors, BET inhibitors, SMG1 inhibitors, ERK inhibitors, LSD1 inhibitors, BH3 mimetics, topoisomerase inhibitors, and RTK inhibitors.

In one aspect, the methods provided herein comprise administering Compound 1 and a glucocorticoid receptor agonist, an interleukin-1 receptor antagonist, or an interleukin-1β blocker to patients with leukemia in combination with one or more additional agents selected from JAK inhibitors, FLT3 inhibitors, mTOR inhibitors, spliceosome inhibitors, BET inhibitors, SMG1 inhibitors, ERK inhibitors, LSD1 inhibitors, BH3 mimetics, topoisomerase inhibitors, and RTK inhibitors.

In one aspect, the methods provided herein comprise administering Compound 1 and a glucocorticoid receptor agonist, an interleukin-1 receptor antagonist, or an interleukin-1β blocker to patients with AML in combination with one or more additional agents selected from JAK inhibitors, FLT3 inhibitors, mTOR inhibitors, spliceosome inhibitors, BET inhibitors, SMG1 inhibitors, ERK inhibitors, LSD1 inhibitors, BH3 mimetics, topoisomerase inhibitors, and RTK inhibitors.

In one aspect, the methods provided herein comprise administering Compound 1 and a glucocorticoid receptor agonist, an interleukin-1 receptor antagonist, or an interleukin-1β blocker in combination with an mTOR inhibitor to patients with leukemia. In certain embodiments, the mTOR inhibitor is selected from everolimus, MLN-0128 and AZD8055. In some embodiments, the mTOR inhibitor is an mTOR kinase inhibitor. In certain embodiments, the mTOR kinase inhibitor is selected from 7-(6-(2-hydroxypropan-2-yl)pyridin-3-yl)-1-((trans)-4-methoxycyclohexyl)-3,4-dihydropyrazino[2,3-b]pyrazin-2(1H)-one (CC-223) and 1-ethyl-7-(2-methyl-6-(1H-1,2,4-triazol-3-yl)pyridin-3-yl)-3,4-dihydropyrazino[2,3-b]pyrazin-2(1H)-one (CC-115). In certain embodiments, Compound 1 and a glucocorticoid receptor agonist, an interleukin-1 receptor antagonist, or an interleukin-1β blocker are administered to patients with leukemia in combination with 7-(6-(2-hydroxypropan-2-yl)pyridin-3-yl)-1-((trans)-4-methoxycyclohexyl)-3,4-dihydropyrazino[2,3-b]pyrazin-2(1H)-one (CC-223). In certain embodiments, Compound 1 and a glucocorticoid receptor agonist, an interleukin-1 receptor antagonist, or an interleukin-1β blocker are administered to patients with leukemia in combination with 1-ethyl-7-(2-methyl-6-(1H-1,2,4-triazol-3-yl)pyridin-3-yl)-3,4-dihydropyrazino[2,3-b]pyrazin-2(1H)-one (CC-115). In certain embodiments, Compound 1 and a glucocorticoid receptor agonist, an interleukin-1 receptor antagonist, or an interleukin-1β blocker are administered to patients with leukemia in combination with everolimus. In certain embodiments, Compound 1 and a glucocorticoid receptor agonist, an interleukin-1 receptor antagonist, or an interleukin-1β blocker are administered to patients with leukemia in combination with MLN-0128. In certain embodiments, Compound 1 and a glucocorticoid receptor agonist, an interleukin-1 receptor antagonist, or an interleukin-1β blocker are administered to patients with leukemia in combination with AZD8055.

In one aspect, the methods provided herein comprise administering Compound 1 and a glucocorticoid receptor agonist, an interleukin-1 receptor antagonist, or an interleukin-1β blocker to patients with AML in combination with an mTOR inhibitor. In certain embodiments, the mTOR inhibitor is selected from everolimus, MLN-0128 and AZD8055. In some embodiments, the mTOR inhibitor is an mTOR kinase inhibitor. In certain embodiments, the mTOR kinase inhibitor is selected from 7-(6-(2-hydroxypropan-2-yl)pyridin-3-yl)-1-((trans)-4-methoxycyclohexyl)-3,4-dihydropyrazino[2,3-b]pyrazin-2(1H)-one (CC-223) and 1-ethyl-7-(2-methyl-6-(1H-1,2,4-triazol-3-yl)pyridin-3-yl)-3,4-dihydropyrazino[2,3-b]pyrazin-2(1H)-one (CC-115). In certain embodiments, Compound 1 and a glucocorticoid receptor agonist, an interleukin-1 receptor antagonist, or an interleukin-1β blocker are administered to patients with AML in combination with 1-ethyl-7-(2-methyl-6-(1H-1,2,4-triazol-3-yl)pyridin-3-yl)-3,4-dihydropyrazino[2,3-b]pyrazin-2(1H)-one. In certain embodiments, Compound 1 and a glucocorticoid receptor agonist, an interleukin-1 receptor antagonist, or an interleukin-1β blocker are administered to patients with AML in combination with everolimus. In certain embodiments, everolimus is administered to patients with AML prior to administration of Compound 1 and dexamethasone. In certain embodiments, Compound 1 and a glucocorticoid receptor agonist, an interleukin-1 receptor antagonist, or an interleukin-1β blocker are administered to patients with AML in combination with MLN-0128. In certain embodiments, Compound 1 and a glucocorticoid receptor agonist, an interleukin-1 receptor antagonist, or an interleukin-1β blocker are administered to patients with AML in combination with AZD8055.

In one aspect, the methods provided herein comprise administering Compound 1 and a glucocorticoid receptor agonist, an interleukin-1 receptor antagonist, or an interleukin-1β blocker to patients with MPN in combination with a JAK inhibitor. In one aspect the JAK inhibitor is selected from a JAK1 inhibitor, a JAK2 inhibitor and a JAK3 inhibitor. In certain embodiments, the JAK inhibitor is selected from tofacitinib, momelotinib, filgotinib, decernotinib, barcitinib, ruxolitinib, fedratinib, NS-018 and pacritinib. In certain embodiments, the JAK inhibitor is selected from tofacitinib, momelotinib, ruxolitinib, fedratinib, NS-018 and pacritinib. In certain embodiments, Compound 1 and a glucocorticoid receptor agonist, an interleukin-1 receptor antagonist, or an interleukin-1β blocker are administered to patients with MPN in combination with tofacitinib. In certain embodiments, Compound 1 and a glucocorticoid receptor agonist, an interleukin-1 receptor antagonist, or an interleukin-1β blocker are administered to patients with MPN in combination with momelotinib. In certain embodiments, Compound 1 and a glucocorticoid receptor agonist, an interleukin-1 receptor antagonist, or an interleukin-1β blocker are administered to patients with MPN in combination with filgotinib. In certain embodiments, Compound 1 and a glucocorticoid receptor agonist, an interleukin-1 receptor antagonist, or an interleukin-1β blocker are administered to patients with MPN in combination with decernotinib. In certain embodiments, Compound 1 and a glucocorticoid receptor agonist, an interleukin-1 receptor antagonist, or an interleukin-1β blocker are administered to patients with MPN in combination with barcitinib. In certain embodiments, Compound 1 and a glucocorticoid receptor agonist, an interleukin-1 receptor antagonist, or an interleukin-1β blocker are administered to patients with MPN in combination with ruxolitinib. In certain embodiments, Compound 1 and a glucocorticoid receptor agonist, an interleukin-1 receptor antagonist, or an interleukin-1β blocker are administered to patients with MPN in combination with fedratinib. In certain embodiments, Compound 1 and a glucocorticoid receptor agonist, an interleukin-1 receptor antagonist, or an interleukin-1β blocker are administered to patients with MPN in combination with NS-018. In certain embodiments, Compound 1 and a glucocorticoid receptor agonist, an interleukin-1 receptor antagonist, or an interleukin-1β blocker are administered to patients with MPN in combination with pacritinib. In certain embodiments, the MPN is IL-3 independent. In certain embodiments, the MPN is characterized by a JAK 2 mutation, for example, a JAK2$^{V617F}$ mutation.

In one aspect, the methods provided herein comprise administering Compound 1 and a glucocorticoid receptor agonist, an interleukin-1 receptor antagonist, or an interleukin-1β blocker to patients with myelofibrosis in combination with a JAK inhibitor. In one aspect the JAK inhibitor is selected from a JAK1 inhibitor, a JAK2 inhibitor and a JAK3 inhibitor. In certain embodiments, the JAK inhibitor is selected from tofacitinib, momelotinib, ruxolitinib, fedratinib, NS-018 and pacritinib. In certain embodiments, Compound 1 and a glucocorticoid receptor agonist, an interleukin-1 receptor antagonist, or an interleukin-1β blocker are administered to patients with myelofibrosis in combination with tofacitinib. In certain embodiments, Compound 1 and a glucocorticoid receptor agonist, an interleukin-1 receptor antagonist, or an interleukin-1β blocker are administered to patients with myelofibrosis in combination with momelotinib. In certain embodiments, Compound 1 and a glucocorticoid receptor agonist, an interleukin-1 receptor antagonist, or an interleukin-1β blocker are administered to patients with myelofibrosis in combination with ruxolitinib. In certain embodiments, Compound 1 and a glucocorticoid receptor agonist, an interleukin-1 receptor antagonist, or an interleukin-1β blocker are administered to patients with myelofibrosis in combination with fedratinib. In certain embodiments, Compound 1 and a glucocorticoid receptor agonist, an interleukin-1 receptor antagonist, or an interleukin-1β blocker are administered to patients with myelofibrosis in combination with NS-018. In certain embodiments, Compound 1 and a glucocorticoid receptor agonist, an interleukin-1 receptor antagonist, or an interleukin-1β blocker are administered to patients with myelofibrosis in combination with pacritinib. In certain embodiments, the myeolofibrosis is characterized by a JAK 2 mutation, for example, a JAK2V617F mutation. In some embodiments, the myelofibrosis is primary myelofibrosis. In other embodiments, the myelofibrosis is secondary myelofibrosis. In some such embodiments, the secondary myelofibrosis is post polycythemia vera myelofibrosis. In other embodiments, the secondary myelofibrosis is post essential thrombocythemia myelofibrosis.

In one aspect, the methods provided herein comprise administering Compound 1 and a glucocorticoid receptor agonist, an interleukin-1 receptor antagonist, or an interleukin-1β blocker to patients with leukemia in combination with a JAK inhibitor. In one aspect the JAK inhibitor is selected from a JAK1 inhibitor, a JAK2 inhibitor and a JAK3 inhibitor. In certain embodiments, the JAK inhibitor is selected from tofacitinib, momelotinib, filgotinib, decernotinib, barcitinib, ruxolitinib, fedratinib, NS-018 and pacritinib. In certain embodiments, the JAK inhibitor is selected from momelotinib, ruxolitinib, fedratinib, NS-018 and pacritinib. In certain embodiments, Compound 1 and a glucocorticoid receptor agonist, an interleukin-1 receptor antagonist, or an interleukin-1β blocker are administered to patients with leukemia in combination with tofacitinib. In certain embodiments, Compound 1 and a glucocorticoid receptor agonist, an interleukin-1 receptor antagonist, or an interleukin-1β blocker are administered to patients with leukemia in combination with momelotinib. In certain embodiments, Compound 1 and a glucocorticoid receptor agonist, an interleukin-1 receptor antagonist, or an interleukin-1β blocker are administered to patients with leukemia in combination with filgotinib. In certain embodiments, Compound 1 and a glucocorticoid receptor agonist, an interleukin-1 receptor antagonist, or an interleukin-1β blocker are administered to patients with leukemia in combination with decernotinib. In certain embodiments, Compound 1 and a glucocorticoid receptor agonist, an interleukin-1 receptor antagonist, or an interleukin-1β blocker are administered to patients with leukemia in combination with barcitinib. In certain embodiments, Compound 1 and a glucocorticoid receptor agonist, an interleukin-1 receptor antagonist, or an interleukin-1β blocker are administered to patients with leukemia in combination with ruxolitinib. In certain embodiments, Compound 1 and a glucocorticoid receptor agonist, an interleukin-1 receptor antagonist, or an interleukin-1β blocker are administered to patients with leukemia in combination with fedratinib. In certain embodiments, Compound 1 and a glucocorticoid receptor agonist, an interleukin-1 receptor antagonist, or an interleukin-1β blocker are administered to patients with leukemia in combination with NS-018. In certain embodiments, Compound 1 and a glucocorticoid receptor agonist, an interleukin-1 receptor antagonist, or an interleukin-1β blocker are administered to patients with leukemia in combination with pacritinib. In certain embodiments, the MPN is characterized by a JAK 2 mutation, for example, a JAK2V617F mutation.

In one aspect, the methods provided herein comprise administering Compound 1 and a glucocorticoid receptor agonist, an interleukin-1 receptor antagonist, or an interleukin-1β blocker to patients with AML in combination with a JAK inhibitor. In one aspect the JAK inhibitor is selected from a JAK1 inhibitor, a JAK2 inhibitor and a JAK3 inhibitor. In certain embodiments, the JAK inhibitor is selected from tofacitinib, momelotinib, filgotinib, decernotinib, barcitinib, ruxolitinib, fedratinib, NS-018 and pacritinib. In certain embodiments, the JAK inhibitor is selected from momelotinib, ruxolitinib, fedratinib, NS-018 and pacritinib. In certain embodiments, Compound 1 and a glucocorticoid receptor agonist, an interleukin-1 receptor antagonist, or an interleukin-1β blocker are administered to patients with AML in combination with tofacitinib. In certain embodiments, Compound 1 and a glucocorticoid receptor agonist, an interleukin-1 receptor antagonist, or an interleukin-1β blocker are administered to patients with AML in combination with momelotinib. In certain embodiments, Compound 1 and a glucocorticoid receptor agonist, an interleukin-1 receptor antagonist, or an interleukin-1β blocker are administered to patients with AML, in combination with filgotinib. In certain embodiments, Compound 1 and a glucocorticoid receptor agonist, an interleukin-1 receptor antagonist, or an interleukin-1β blocker are administered to patients with AML in combination with decernotinib. In certain embodiments, Compound 1 and a glucocorticoid receptor agonist, an interleukin-1 receptor antagonist, or an interleukin-1β blocker are administered to patients with AML in combination with barcitinib. In certain embodiments, Compound 1 and dexametha a glucocorticoid receptor agonist, an interleukin-1 receptor antagonist, or an interleukin-1β blocker sone are administered to patients with AML in combination with ruxolitinib. In certain embodiments, Compound 1 and a glucocorticoid receptor agonist, an interleukin-1 receptor antagonist, or an interleukin-1β blocker are administered to patients with AML in combination with fedratinib. In certain embodiments, Compound 1 and a glucocorticoid receptor agonist, an interleukin-1 receptor antagonist, or an interleukin-1β blocker are administered to patients with AML in combination with NS-018. In certain embodiments, Compound 1 and a glucocorticoid receptor agonist, an interleukin-1 receptor antagonist, or an interleukin-1β blocker are administered to patients with AML in combination with pacritinib. In certain embodiments, the MPN is characterized by a JAK 2 mutation, for example, a JAK2V617F mutation.

In one aspect, the methods provided herein comprise administering Compound 1 and a glucocorticoid receptor agonist, an interleukin-1 receptor antagonist, or an interleukin-1β blocker to patients with leukemia in combination with a FLT3 kinase inhibitor. In certain embodiments, the FLT3 kinase inhibitor is selected from quizartinib, sunitinib, sunitinib malate, midostaurin, pexidartinib, lestaurtinib, tandutinib, and crenolanib. In certain embodiments, Compound 1 and a glucocorticoid receptor agonist, an interleukin-1 receptor antagonist, or an interleukin-1β blocker are administered to patients with leukemia in combination with quizartinib. In certain embodiments, Compound 1 and a glucocorticoid receptor agonist, an interleukin-1 receptor antagonist, or an interleukin-1β blocker are administered to patients with leukemia in combination with sunitinib. In certain embodiments, Compound 1 and a glucocorticoid receptor agonist, an interleukin-1 receptor antagonist, or an interleukin-1β blocker are administered to patients with leukemia in combination with midostaurin. In certain embodiments, Compound 1 and a glucocorticoid receptor agonist, an interleukin-1 receptor antagonist, or an interleukin-1β blocker are administered to patients with leukemia in combination with pexidartinib. In certain embodiments, Compound 1 and a glucocorticoid receptor agonist, an interleukin-1 receptor antagonist, or an interleukin-1β blocker are administered to patients with leukemia in combination with lestaurtinib. In certain embodiments, Compound 1 and a glucocorticoid receptor agonist, an interleukin-1 receptor antagonist, or an interleukin-1β blocker are administered to patients with leukemia in combination with tandutinib. In certain embodiments, Compound 1 and a glucocorticoid receptor agonist, an interleukin-1 receptor antagonist, or an interleukin-1β blocker are administered to patients with leukemia in combination with crenolanib. In certain embodiments, the patient carries a FLT3-ITD mutation.

In one aspect, the methods provided herein comprise administering Compound 1 and a glucocorticoid receptor agonist, an interleukin-1 receptor antagonist, or an interleukin-1β blocker to patients with AML in combination with a FLT3 kinase inhibitor. In certain embodiments, the FLT3 kinase inhibitor is selected from quizartinib, sunitinib, sunitinib malate, midostaurin, pexidartinib, lestaurtinib, tandutinib, quizartinib and crenolanib. In certain embodiments, Compound 1 and a glucocorticoid receptor agonist, an interleukin-1 receptor antagonist, or an interleukin-1β blocker are administered to patients with AML in combination with quizartinib. In certain embodiments, Compound 1 and dexamet a glucocorticoid receptor agonist, an interleukin-1 receptor antagonist, or an interleukin-1β blocker hasone are administered to patients with AML in combination with sunitinib. In certain embodiments, Compound 1 and a glucocorticoid receptor agonist, an interleukin-1 receptor antagonist, or an interleukin-1β blocker are administered to patients with AML in combination with midostaurin. In certain embodiments, Compound 1 and a glucocorticoid receptor agonist, an interleukin-1 receptor antagonist, or an interleukin-1β blocker are administered to patients with AML in combination with pexidartinib. In certain embodiments, Compound 1 and a glucocorticoid receptor agonist, an interleukin-1 receptor antagonist, or an interleukin-1β blocker are administered to patients with AML in combination with lestaurtinib. In certain embodiments, Compound 1 and a glucocorticoid receptor agonist, an interleukin-1 receptor antagonist, or an interleukin-1β blocker are administered to patients with AML in combination with tandutinib. In certain embodiments, Compound 1 and a glucocorticoid receptor agonist, an interleukin-1 receptor antagonist, or an interleukin-1β blocker are administered to patients with AML in combination with crenolanib. In certain embodiments, the patient carries a FLT3-ITD mutation.

In certain embodiments, Compound 1 and a glucocorticoid receptor agonist, an interleukin-1 receptor antagonist, or an interleukin-1β blocker are administered to patients with leukemia in combination with a spliceosome inhibitor. In certain embodiments, Compound 1 and a glucocorticoid receptor agonist, an interleukin-1 receptor antagonist, or an interleukin-1β blocker are administered to patients with AML in combination with a spliceosome inhibitor. In certain embodiments, the spliceosome inhibitor is pladienolide B, 6-deoxypladienolide D, or H3B-8800.

In one aspect, the methods provided herein comprise administering Compound 1 and a glucocorticoid receptor agonist, an interleukin-1 receptor antagonist, or an interleukin-1β blocker to patients with leukemia in combination with an SMG1 kinase inhibitor. In one aspect, the methods provided herein comprise administering Compound 1 and a glucocorticoid receptor agonist, an interleukin-1 receptor antagonist, or an interleukin-1β blocker to patients with AML in combination with an SMG1 kinase inhibitor. In certain embodiments, the SMG1 inhibitor is 1-ethyl-7-(2-methyl-6-(1H-1,2,4-triazol-3-yl)pyridin-3-yl)-3,4-dihydropyrazino[2,3-b]pyrazin-2(1H)-one, chloro-N,N-diethyl-5-((4-(2-(4-(3-methylureido)phenyl)pyridin-4-yl)pyrimidin-2-yl)amino)benzenesulfonamide (compound Ii), or a compound disclosed in A. Gopalsamy et al, *Bioorg. Med Chem Lett.* 2012, 22:6636-66412 (for example, chloro-N,N-diethyl-5-((4-(2-(4-(3-methylureido)phenyl)pyridin-4-yl)pyrimidin-2-yl)amino)benzenesulfonamide.

In one aspect, the methods provided herein comprise administering Compound 1 and dexam a glucocorticoid receptor agonist, an interleukin-1 receptor antagonist, or an interleukin-1β blocker ethasone to patients with leukemia in combination with a BCL2 inhibitor. In certain embodiments, Compound 1 and a glucocorticoid receptor agonist, an interleukin-1 receptor antagonist, or an interleukin-1β blocker methasone are administered to patients with AML in combination with a BCL2 inhibitor. In certain embodiments, Compound 1 and a glucocorticoid receptor agonist, an interleukin-1 receptor antagonist, or an interleukin-1β blocker are administered to patients with AML in combination with a BCL2 inhibitor, for example, venetoclax or navitoclax. In certain embodiments, the BCL2 inhibitor is venetoclax.

In one embodiment, the AML is resistant to treatment with a BCL2 inhibitor. In one embodiment, the AML that has acquired resistance to Venetoclax treatment. In one embodiment, the methods provided herein comprising administering a combination of Compound 1, a glucocorticoid receptor agonist, an interleukin-1 receptor antagonist, or an interleukin-1β blocker and a BCL2 inhibitor to a patient having an AML that has acquired resistance to Venetoclax treatment. In one embodiment, the methods provided herein comprising administering a combination of Compound 1, a glucocorticoid receptor agonist, an interleukin-1 receptor antagonist, or an interleukin-1β blocker and Venetoclax to a patient having AML that has acquired resistance to Venetoclax treatment.

In one aspect, the methods provided herein comprise administering Compound 1 and a glucocorticoid receptor agonist, an interleukin-1 receptor antagonist, or an interleukin-1β blocker to patients with leukemia in combination with a topoisomerase inhibitor. In certain embodiments, Compound 1 and a glucocorticoid receptor agonist, an interleukin-1 receptor antagonist, or an interleukin-1β blocker are administered to patients with AML in combination with a topoisomerase inhibitor, for example, irinotecan, topotecan, camptothecin, lamellarin D, etoposide, teniposide, doxorubicin, daunorubicin, mitoxantrone, amsacrine, ellipticines, aurintricarboxylic acid, or HU-331. In certain embodiments, the topoisomerase inhibitor is topotecan.

In certain embodiments, Compound 1 and a glucocorticoid receptor agonist, an interleukin-1 receptor antagonist, or an interleukin-1β blocker are administered to patients with leukemia in combination with a BET inhibitor. In certain embodiments, Compound 1 and a glucocorticoid receptor agonist, an interleukin-1 receptor antagonist, or an interleukin-1β blocker are administered to patients with AML in combination with a BET inhibitor. In certain embodiments, the BET inhibitor is selected from GSK525762A, OTX015, BMS-986158, TEN-010, CPI-0610, INCB54329, BAY1238097, FT-1101, C90010, ABBV-075, BI 894999, GS-5829, GSK1210151A (I-BET-151), CPI-203, RVX 208, XD46, MS436, PFI-1, RVX2135, ZEN3365, XD14, ARV-771, MZ-1, PLX5117, 4-[2-(cyclopropylmethoxy)-5-(methanesulfonyl)phenyl]-2-methylisoquinolin-1(2H)-one (Compound A), EP11313 and EP11336.

In certain embodiments, Compound 1 and a glucocorticoid receptor agonist, an interleukin-1 receptor antagonist, or an interleukin-1β blocker are administered to patients with leukemia in combination with an LSD1 inhibitor. In certain embodiments, Compound 1 and a glucocorticoid receptor agonist, an interleukin-1 receptor antagonist, or an interleukin-1β blocker are administered to patients with AML in combination with an LSD1 inhibitor. In certain embodiments, the LSD1 inhibitor is selected from ORY-1001, ORY-2001, INCB-59872, INCB 054329, IMG-7289, TAK 418, GSK-2879552, and 4-[2-(4-amino-piperidin-1-yl)-5-(3-fluoro-4-methoxy-phenyl)-1-methyl-6-oxo-1,6-dihydropyrimidin-4-yl]-2-fluoro-benzonitrile or a salt thereof (e.g. besylate salt, Compound B).

In one aspect, the methods provided herein comprise administering Compound 1 and a glucocorticoid receptor agonist, an interleukin-1 receptor antagonist, or an interleukin-1β blocker to patients with leukemia in combination with triptolide, retaspimycin, alvespimycin, 7-(6-(2-hydroxypropan-2-yl)pyridin-3-yl)-1-((trans)-4-methoxycyclohexyl)-3,4-dihydropyrazino[2,3-b]pyrazin-2(1H)-one (CC-223), 1-ethyl-7-(2-methyl-6-(1H-1,2,4-triazol-3-yl)pyridin-3-yl)-3,4-dihydropyrazino[2,3-b]pyrazin-2(1H)-one (CC-115), rapamycin, MLN-0128, everolimus, AZD8055, pladienolide B, topotecan, thioguanine, mitoxantrone, etoposide, decitabine, daunorubicin, clofarabine, cladribine, 6-mercaptopurine, chloro-N,N-diethyl-5-((4-(2-(4-(3-methylureido)phenyl)pyridin-4-yl)pyrimidin-2-yl)amino) benzenesulfonamide (compound Ii), fedratinib, sunitinib, pexidartinib, midostaurin, lestaurtinib, momelotinib, quizartinib, and crenolanib.

In one aspect, the methods provided herein comprise administering Compound 1 and a glucocorticoid receptor agonist, an interleukin-1 receptor antagonist, or an interleukin-1β blocker to patients with AML in combination with triptolide, retaspimycin, alvespimycin, 7-(6-(2-hydroxypropan-2-yl)pyridin-3-yl)-1-((trans)-4-methoxycyclohexyl)-3,4-dihydropyrazino[2,3-b]pyrazin-2(1H)-one (CC-223), 1-ethyl-7-(2-methyl-6-(1H-1,2,4-triazol-3-yl)pyridin-3-yl)-3,4-dihydropyrazino[2,3-b]pyrazin-2(1H)-one (CC-115), rapamycin, MLN-0128, everolimus, AZD8055, pladienolide B, topotecan, thioguanine, mitoxantrone, etoposide, decitabine, daunorubicin, clofarabine, cladribine, 6-mercaptopurine, chloro-N,N-diethyl-5-((4-(2-(4-(3-methylureido)phenyl)pyridin-4-yl)pyrimidin-2-yl)amino) benzenesulfonamide (compound Ii), fedratinib, sunitinib, pexidartinib, midostaurin, lestaurtinib, momelotinib, quizartinib, and crenolanib.

In one aspect, the methods provided herein comprise administering Compound 1 and a glucocorticoid receptor agonist, an interleukin-1 receptor antagonist, or an interleukin-1β blocker to patients with cancer in combination with an mTOR inhibitor, wherein the cancer is selected from breast cancer, kidney cancer, pancreatic cancer, gastrointestinal cancer, lung cancer, neuroendocrine tumor (NET), and renal cell carcinoma (RCC). In certain embodiments, the mTOR inhibitor is selected from everolimus, MLN-0128 and AZD8055. In some embodiments, the mTOR inhibitor is an mTOR kinase inhibitor. In certain embodiments, the mTOR kinase inhibitor is selected from 7-(6-(2-hydroxypropan-2-yl)pyridin-3-yl)-1-((trans)-4-methoxycyclohexyl)-3,4-dihydropyrazino[2,3-b]pyrazin-2(1H)-one (CC-223) and 1-ethyl-7-(2-methyl-6-(1H-1,2,4-triazol-3-yl)pyridin-3-yl)-3,4-dihydropyrazino[2,3-b]pyrazin-2(1H)-one (CC-115). In one embodiment, the mTOR kinase inhibitor is 7-(6-(2-hydroxypropan-2-yl)pyridin-3-yl)-1-((trans)-4-methoxycyclohexyl)-3,4-dihydropyrazino[2,3-b]pyrazin-2(1H)-one (CC-223). In one embodiment, the mTOR kinase inhibitor is 1-ethyl-7-(2-methyl-6-(1H-1,2,4-triazol-3-yl)pyridin-3-yl)-3,4-dihydropyrazino[2,3-b]pyrazin-2(1H)-one (CC-115). In one embodiment, the mTOR inhibitor is everolimus. In one embodiment, the mTOR inhibitor is temsirolimus. In one embodiment, the mTOR inhibitor is MLN-0128. In one embodiment, the mTOR inhibitor is AZD8055.

In certain embodiments, Compound 1 and a glucocorticoid receptor agonist, an interleukin-1 receptor antagonist, or an interleukin-1β blocker are administered to breast cancer patients in combination with everolimus.

In certain embodiments, Compound 1 and a glucocorticoid receptor agonist, an interleukin-1 receptor antagonist, or an interleukin-1β blocker methasone are administered to kidney cancer patients in combination with everolimus.

In certain embodiments, Compound 1 and a glucocorticoid receptor agonist, an interleukin-1 receptor antagonist, or an interleukin-1β blocker are administered to pancreatic cancer patients in combination with everolimus.

In certain embodiments, Compound 1 and a glucocorticoid receptor agonist, an interleukin-1 receptor antagonist, or an interleukin-1β blocker are administered to gastrointestinal cancer patients in combination with everolimus.

In certain embodiments, Compound 1 and a glucocorticoid receptor agonist, an interleukin-1 receptor antagonist, or an interleukin-1β blocker are administered to lung cancer patients in combination with everolimus.

In certain embodiments, Compound 1 and a glucocorticoid receptor agonist, an interleukin-1 receptor antagonist, or an interleukin-1β blocker are administered to neuroendocrine tumor patients in combination with everolimus.

In certain embodiments, Compound 1 and a glucocorticoid receptor agonist, an interleukin-1 receptor antagonist, or an interleukin-1β blocker are administered to renal cell carcinoma patients in combination with everolimus.

In one embodiment, Compound 1 is administered daily in an amount ranging from about 0.1 to about 20 mg, from about 1 to about 15 mg, from about 1 to about 10 mg, or from about 1 to about 15 mg prior to, during, or after the occurrence of the adverse effect associated with the administration of an anti-cancer drug to a patient. In certain embodiments, Compound 1 is administered in combination with specific agents such as heparin, aspirin, coumadin, or G-CSF to avoid adverse effects that are associated with anti-cancer drugs such as but not limited to neutropenia or thrombocytopenia.

In one embodiment, Compound 1 and a glucocorticoid receptor agonist, an interleukin-1 receptor antagonist, or an interleukin-1β blocker are administered to patients with diseases and disorders associated with or characterized by, undesired angiogenesis in combination with additional active ingredients, including, but not limited to, anti-cancer drugs, anti-inflammatories, antihistamines, antibiotics, and steroids.

In certain embodiments, the methods provided herein further comprise administration of one or more of calcium, calcitriol, or vitamin D supplementation with Compound 1. In certain embodiments, the methods provided herein comprise administration of calcium, calcitriol, and vitamin D supplementation prior to the treatment with Compound 1. In certain embodiments, the methods provided herein comprise administration of calcium, calcitriol, and vitamin D supplementation prior to the administration of first dose of Compound 1 in each cycle. In certain embodiments, the methods provided herein comprise administration of calcium, calcitriol, and vitamin D supplementation at least up to 3 days prior to the treatment with Compound 1. In certain embodiments, the methods provided herein comprise administration of calcium, calcitriol, and vitamin D supplementation prior to the administration of first dose of Compound 1 in each cycle. In certain embodiments, the methods provided herein comprise administration of calcium, calcitriol, and vitamin D supplementation at least up to 3 days prior to the administration of first dose of Compound 1 in each cycle. In certain embodiments, the methods provided herein comprise administration of calcium, calcitriol, and vitamin D supplementation prior to administration of first dose of Compound 1 in each cycle and continues after administration of the last dose of Compound 1 in each cycle. In certain embodiments, the methods provided herein comprise administration of calcium, calcitriol, and vitamin D supplementation at least up to 3 days prior to administration of first dose of Compound 1 in each cycle and continues until at least up to 3 days after administration of the last dose of Compound 1 in each cycle (e.g., at least up to day 8 when Compound 1 is administered on Days 1-5). In one embodiment, the methods provided herein comprise administration of calcium, calcitriol, and vitamin D supplementation at least up to 3 days prior to administration of day 1 of each cycle and continue until ≥3 days after the last dose of Compound 1 in each cycle (eg, ≥Day 8 when Compound 1 is administered on Days 1-5, ≥Day 13 when Compound 1 is administered on Days 1-3 and Days 8-10).

In certain embodiments, calcium supplementation is administered to deliver at least 1200 mg of elemental calcium per day given in divided doses. In certain embodiments, calcium supplementation is administered as calcium carbonate in a dose of 500 mg administered three times a day per orally (PO).

In certain embodiments, calcitriol supplementation is administered to deliver 0.25 µg calcitriol (PO) once daily.

In certain embodiments, vitamin D supplementation is administered to deliver about 500 IU to about 50,000 IU vitamin D once daily. In certain embodiments, vitamin D supplementation is administered to deliver about 1000 IU vitamin D once daily. In certain embodiments, vitamin D supplementation is administered to deliver about 50,000 IU vitamin D weekly. In certain embodiments, vitamin D supplementation is administered to deliver about 1000 IU vitamin D2 or D3 once daily. In certain embodiments, vitamin D supplementation is administered to deliver about 500 IU vitamin D once daily. In certain embodiments, vitamin D supplementation is administered to deliver about 50,000 IU vitamin D weekly. In certain embodiments, vitamin D supplementation is administered to deliver about 20,000 IU vitamin D weekly. In certain embodiments, vitamin D supplementation is administered to deliver about 1000 IU vitamin D2 or D3 once daily. In certain embodiments, vitamin D supplementation is administered to deliver about 50,000 IU vitamin D2 or D3 weekly. In certain embodiments, vitamin D supplementation is administered to deliver about 20,000 IU vitamin D2 or D3 weekly.

In certain embodiments, Compound 1 and a glucocorticoid receptor agonist, an interleukin-1 receptor antagonist, or an interleukin-1β blocker are administered in combination with doxetaxol to patients with non-small cell lung cancer who were previously treated with carbo/VP 16 and radiotherapy.

Use with Transplantation Therapy

Compound 1 and a glucocorticoid receptor agonist, an interleukin-1 receptor antagonist, or an interleukin-1β blocker can be used to reduce the risk of Graft Versus Host Disease (GVHD). In certain embodiments of the methods provided herein, Compound 1 and a glucocorticoid receptor agonist, an interleukin-1 receptor antagonist, or an interleukin-1β blocker is administered in conjunction with transplantation therapy.

As those of ordinary skill in the art are aware, the treatment of cancer is often based on the stages and mechanism of the disease. For example, as inevitable leukemic transformation develops in certain stages of cancer, transplantation of peripheral blood stem cells, hematopoietic stem cell preparation or bone marrow may be necessary. The combined use of Compound 1 provided herein, and transplantation therapy provides a unique and unexpected synergism. In particular, Compound 1 exhibits immunomodulatory activity that may provide additive or synergistic effects when given concurrently with transplantation therapy in patients with cancer.

Compound 1 and a glucocorticoid receptor agonist, an interleukin-1 receptor antagonist, or an interleukin-1β blocker can work in combination with transplantation therapy reducing complications associated with the invasive procedure of transplantation and risk of GVHD. Encompassed herein is a method of treating, preventing and/or managing cancer which comprises administering to a patient (e.g., a human) Compound 1 a glucocorticoid receptor agonist, an interleukin-1 receptor antagonist, or an interleukin-1β blocker before, during, or after the transplantation of umbilical cord blood, placental blood, peripheral blood stem cell, hematopoietic stem cell preparation, or bone marrow. Some examples of stem cells suitable for use in the methods provided herein are disclosed in U.S. Pat. No. 7,498,171, the disclosure of which is incorporated herein by reference in its entirety.

In one embodiment, Compound 1 and a glucocorticoid receptor agonist, an interleukin-1 receptor antagonist, or an interleukin-1β blocker is administered to patients with acute myeloid leukemia before, during, or after transplantation.

In one embodiment, Compound 1 and a glucocorticoid receptor agonist, an interleukin-1 receptor antagonist, or an interleukin-1β blocker is administered to patients with multiple myeloma before, during, or after the transplantation of autologous peripheral blood progenitor cells.

In one embodiment, Compound 1 and a glucocorticoid receptor agonist, an interleukin-1 receptor antagonist, or an interleukin-1β blocker is administered to patients with NHL (e.g., DLBCL) before, during, or after the transplantation of autologous peripheral blood progenitor cells.

Cycling Therapy

In certain embodiments, Compound 1 is cyclically administered to a patient independent of the cancer treated. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improve the efficacy of the treatment.

In certain embodiments, Compound 1 is administered daily in a single or divided dose in a four to six week cycle with a rest period of about a week or two weeks. In certain embodiments, Compound 1 is administered daily in a single or divided doses for one to ten consecutive days of a 28 day cycle, then a rest period with no administration for rest of the 28 day cycle. The cycling method further allows the frequency, number, and length of dosing cycles to be increased. Thus, encompassed herein in certain embodiments is the administration of Compound 1 for more cycles than are typical when it is administered alone. In certain embodiments, Compound 1 is administered for a greater number of cycles that would typically cause dose-limiting toxicity in a patient to whom an additional active ingredient is not also being administered.

In one embodiment, Compound 1 is administered daily and continuously for three or four weeks to administer a dose of Compound 1 from about 0.1 to about 20 mg/d followed by a break of one or two weeks.

In another embodiment, Compound 1 is administered intravenously and an additional active ingredient is administered orally, with administration of Compound 1 occurring 30 to 60 minutes prior to an additional active ingredient, during a cycle of four to six weeks. In certain embodiments, the combination of Compound 1 and an additional active ingredient is administered by intravenous infusion over about 90 minutes every cycle. In certain embodiments, one cycle comprises the administration from about 0.1 to about 150 mg/day of Compound 1 and from about 50 to about 200 mg/m$^2$/day of an additional active ingredient daily for three to four weeks and then one or two weeks of rest. In certain embodiments, the number of cycles during which the combinatorial treatment is administered to a patient is ranging from about one to about 24 cycles, from about two to about 16 cycles, or from about four to about three cycles.

In one embodiment, a cycling therapy provided herein comprises administering Compound 1 in a treatment cycle which includes an administration period of up to 3 days followed by a rest period. In one embodiment, the treatment cycle includes an administration period of 3 days followed by a rest period. In one embodiment, a cycling therapy provided herein comprises administering Compound 1 in a treatment cycle which includes an administration period of up to 5 days followed by a rest period. In one embodiment, the treatment cycle includes an administration period of 5 days followed by a rest period. In one embodiment, the treatment cycle includes an administration period of up to 7 days followed by a rest period. In one embodiment, the treatment cycle includes an administration period of 7 days followed by a rest period. In one embodiment, the treatment cycle includes an administration period of up to 10 days followed by a rest period. In one embodiment, the rest period is from about 10 days up to about 40 days. In one embodiment, the treatment cycle includes an administration period of up to 10 days followed by a rest period from about 10 days up to about 40 days. In one embodiment, the treatment cycle includes an administration period of up to 10 days followed by a rest period from about 23 days up to about 37 days. In one embodiment, the rest period is from about 23 days up to about 37 days. In one embodiment, the rest period is 23 days. In one embodiment, the treatment cycle includes an administration period of up to 10 days followed by a rest period of 23 days. In one embodiment, the rest period is 37 days. In one embodiment, the treatment cycle includes an administration period of up to 10 days followed by a rest period of 37 days.

In one embodiment, the treatment cycle includes an administration of Compound 1 on days 1 to 3 of a 28 day cycle. In one embodiment, the treatment cycle includes an administration of Compound 1 on days 1 to 5 of a 28 day cycle. In another embodiment, the treatment cycle includes an administration of Compound 1 on days 1-7 of a 28 day cycle. In another embodiment, the treatment cycle includes an administration of Compound 1 on days 1-10 of a 28 day cycle. In one embodiment, the treatment cycle includes an administration on days 1 to 5 of a 42 day cycle. In another embodiment, the treatment cycle includes an administration on days 1-10 of a 42 day cycle. In another embodiment, the treatment cycle includes an administration on days 1-5 and 15-19 of a 28 day cycle. In another embodiment, the treatment cycle includes an administration on days 1-3 and 8-10 of a 28 day cycle.

In one embodiment, the treatment cycle includes an administration of Compound 1 on days 1 to 21 of a 28 day cycle. In another embodiment, the treatment cycle includes an administration on days 1 to 5 of a 7 day cycle. In another embodiment, the treatment cycle includes an administration on days 1 to 7 of a 7 day cycle. In one embodiment, the treatment cycle includes an administration of Compound 1 on days 1 to 5 of a 21 day cycle. In one embodiment, the treatment cycle includes an administration of Compound 1 on days 1 to 7 of a 21 day cycle. In one embodiment, the treatment cycle includes an administration of Compound 1 on days 1 to 7 of a 28 day cycle.

Any treatment cycle described herein can be repeated for at least 2, 3, 4, 5, 6, 7, 8, or more cycles. In certain instances, the treatment cycle as described herein includes from 1 to about 24 cycles, from about 2 to about 16 cycles, or from about 2 to about 4 cycles. In certain instances a treatment cycle as described herein includes from 1 to about 4 cycles. In certain embodiments, cycle 1 to 4 are all 28 day cycles. In certain embodiments, cycle 1 is a 42 day cycle and cycles 2 to 4 are 28 day cycles. In some embodiments, Compound 1 is administered for 1 to 13 cycles of 28 days (e.g. about 1 year). In certain instances, the cycling therapy is not limited to the number of cycles, and the therapy is continued until disease progression. Cycles, can in certain instances, include varying the duration of administration periods and/or rest periods described herein.

In one embodiment the treatment cycle includes administering Compound 1 at a dosage amount of about 0.3 mg/day, 0.6 mg/day, 1.2 mg/day, 1.8 mg/day, 2.4 mg/day, 3 mg/day, 3.6 mg/day, 4.5 mg/day, 5.4 mg/day, 7.2 mg/day, 8.1 mg/day, 9.0 mg/day, 10.0 mg/day, 10.8 mg/day, or 12.2 mg/day administered once per day. In one embodiment the treatment cycle includes administering Compound 1 at a dosage amount of about 0.3 mg/day, 0.6 mg/day, 1.2 mg/day, 1.8 mg/day, 2.4 mg/day, 3 mg/day, 3.6 mg/day, 4.5 mg/day, 5.4 mg/day, 7.2 mg/day, 8.1 mg/day, 9.0 mg/day, 10.0 mg/day, 10.8 mg/day, 12.2 mg/day, or 20 mg/day administered once per day. In one embodiment the treatment cycle includes administering Compound 1 at a dosage amount of about 0.6 mg/day, 1.2 mg/day, 1.8 mg/day, 2.4 mg/day, 3 mg/day, or 3.6 mg/day, administered once per day. In some such embodiments, the treatment cycle includes administering Compound 1 at a dosage amount of about 0.6 mg, 1.2 mg, 1.8 mg, 2.4 mg, 3 mg/day, or 3.6 mg on days 1 to 3 of a 28 day cycle. In other embodiments, the treatment cycle includes administering Compound 1 at a dosage amount of about 0.6 mg/day, 1.2 mg, 1.8 mg, 2.4 mg, 3 mg/day, or 3.6 mg on days 1 to 5 and 15 to 19 of a 28 day cycle. In other embodiments, the treatment cycle includes administering Compound 1 at a dosage amount of about 0.6 mg, 1.2 mg, 1.8 mg, 2.4 mg, 3 mg/day, 3.6 mg, 4.5 mg/day, 5.4 mg/day, 7.2 mg/day, 8.1 mg/day, 9.0 mg/day, or 10.0 mg/day, on days 1 to 5 and 15 to 19 of a 28 day cycle.

In some such embodiments, the treatment cycle includes administering Compound 1 at a dosage amount of about 2.4 mg on days 1 to 5 of a 28 day cycle. In some such embodiments, the treatment cycle includes administering Compound 1 at a dosage amount of about 3.6 mg on days 1 to 5 of a 28 day cycle.

Compound 1 can be administered at the same amount for all administration periods in a treatment cycle. Alternatively, in one embodiment, the compound is administered at different doses in the administration periods.

In some embodiments, the treatment cycle includes administering Compound 1 at a first dosage amount on days 1 to 3, and at a second dosage amount on days 8 to 10 of a 28 day cycle, wherein the first and the second dosage amounts are the same or different. In some such embodiments, the treatment cycle includes administering Compound 1 at a dosage amount of about 2.4 mg on days 1 to 3, and at a dosage amount of about 3.6 mg on days 8 to 10 of a 28 day cycle.

In one embodiment, Compound 1 is administered to a subject in a cycle, wherein the cycle comprises administering for at least 5 days in a 28 day cycle. In one embodiment, Compound 1 is administered to a subject in a cycle, wherein the cycle comprises administering on days 1 to 5 of a 28 day cycle. In one embodiment, Compound 1 is administered in a dose of about 0.1 mg to about 20 mg on days 1 to 5 of a 28 day cycle. In one embodiment, Compound 1 is administered in a dose of about 0.5 mg to about 5 mg on days 1 to 5 of a 28 day cycle. In one embodiment, Compound 1 is administered in a dose of about 0.5 mg to about 10 mg on days 1 to 5 of a 28 day cycle. In one embodiment, Compound 1 is administered to a subject in a cycle, wherein the cycle comprises administering on days 1 to 5 and 15 to 19 of a 28 day cycle. In one embodiment, Compound 1 is administered in a dose of about 0.1 mg to about 20 mg on days 1 to 5 and 15 to 19 of a 28 day cycle. In one embodiment, Compound 1 is administered in a dose of about 0.5 mg to about 5 mg on days 1 to 5 and 15 to 19 of a 28 day cycle. In one embodiment, Compound 1 is administered in a dose of about 0.5 mg to about 10 mg on days 1 to 5 and 15 to 19 of a 28 day cycle.

Patient Population

In certain embodiments of the methods provided herein, the subject is an animal, preferably a mammal, more preferably a non-human primate. In particular embodiments, the subject is a human. The subject can be a male or female subject.

Particularly useful subjects for the methods provided herein include human cancer patients, for example, those who have been diagnosed with leukemia, including acute myeloid leukemia, acute lymphocytic leukemia, chronic myelogenous leukemia, and chronic myelogenous leukemia. In certain embodiments, the subject has not been diagnosed with acute promyelocytic leukemia.

In some embodiments, the subject has a higher than normal blast population. In some embodiments, the subject has a blast population of at least 10%. In some embodiments, the subject has a blast population of between 10 and 15%. In some embodiments, the subject has a blast population of at least 15%. In some embodiments, the subject has a blast population of between 15 and 20%. In some embodiments, the subject has a blast population of at least 20%. In some embodiments, the subject has a blast population of about 10-15%, about 15-20%, or about 20-25%. In other embodiments, the subject has a blast population of less than 10%. In the context of the methods described herein, useful subjects having a blast population of less than 10% includes those subjects that, for any reason according to the judgment of the skilled practitioner in the art, are in need of treatment with a compound provided herein, alone or in combination with an additional active agent.

In some embodiments, the subject is treated based on the Eastern Cooperative Oncology Group (ECOG) performance status score of the subject for leukemia. ECOG performance status can be scored on a scale of 0 to 5, with 0 denoting asymptomatic; 1 denoting symptomatic but completely ambulant; 2 denoting symptomatic and <50% in bed during the day; 3 denoting symptomatic and >50% in bed, but not bed bound; 4 denoting bed bound; and 5 denoting death. In some embodiments, the subject has an ECOG performance status score of 0 or 1. In some embodiments, the subject has an ECOG performance status score of 0. In some embodiments, the subject has an ECOG performance status score of 1. In other embodiments, the subject has an ECOG performance status score of 2.

In certain embodiments, the methods provided herein encompass the treatment of subjects who have not been previously treated for leukemia. In some embodiments, the subject has not undergone allogeneic bone marrow transplantation. In some embodiments, the subject has not undergone a stem cell transplantation. In some embodiments, the subject has not received hydroxyurea treatment. In some embodiments, the subject has not been treated with any investigational products for leukemia. In some embodiments, the subject has not been treated with systemic glucocorticoids.

In other embodiments, the methods encompass treating subjects who have been previously treated or are currently being treated for leukemia. For example, the subject may have been previously treated or are currently being treated with a standard treatment regimen for leukemia. The subject may have been treated with any standard leukemia treatment regimen known to the practitioner of skill in the art. In certain embodiments, the subject has been previously treated with at least one induction/reinduction or consolidation AML, regimen. In some embodiments, the subject has undergone autologous bone marrow transplantation or stem cell transplantation as part of a consolidation regimen. In some embodiments, the bone marrow or stem cell transplantation occurred at least 3 months prior to treatment according to the methods provided herein. In some embodiments, the subject has undergone hydroxyurea treatment. In some embodiments, the hydroxyurea treatment occurred no later than 24 hours prior to treatment according to the methods provided herein. In some embodiments, the subject has undergone prior induction or consolidation therapy with cytarabine (Ara-C). In some embodiments, the subject has undergone treatment with systemic glucocorticosteroids. In some embodiments, the glucocorticosteroid treatment occurred no later 24 hours prior to treatment according to the methods described herein. In other embodiments, the methods encompass treating subjects who have been previously treated for cancer, but are non-responsive to standard therapies.

In some embodiments, the subject has been diagnosed with a relapsed or refractory AML subtype, as defined by the World Health Organization (WHO). Relapsed or refractory disease may be de novo AML or secondary AML, e.g., therapy-related AML (t-AML).

In some embodiments, the subject has been diagnosed with leukemia, characterized by presence of a mutant allele of IDH2. In one embodiment, the mutant allele of IDH2 is IDH2 R140Q or R172K.

In some embodiments, the subject has been diagnosed with AML, characterized by presence of a mutant allele of IDH2. In one embodiment, the mutant allele of IDH2 is IDH2 R140Q or R172K.

Thus, treatment with Compound 1 and a glucocorticoid receptor agonist, an interleukin-1 receptor antagonist, or an interleukin-1β blocker provided herein could provide an alternative for patients who do not respond to other methods of treatment. In some embodiments, such other methods of treatment encompass treatment with GLEEVEC® (imatinib mesylate). In some embodiments, provided herein are methods of treatment of Philadelphia chromosome positive chronic myelogenous leukemia (Ph+CML). In some embodiments, provided herein is Compound I for use in methods of treatment of Philadelphia chromosome positive chronic myelogenous leukemia (Ph+CML). In some embodiments, provided herein are methods of treatment of GLEEVEC® (imatinib mesylate) resistant Philadelphia chromosome positive chronic myelogenous leukemia (Ph+CML). In some embodiments, provided herein is Compound I for use in methods of treatment of GLEEVEC® (imatinib mesylate) resistant Philadelphia chromosome positive chronic myelogenous leukemia (Ph+CML).

In some embodiments, the subject has been diagnosed with drug resistant leukemias, such as CML. Thus, treatment with Compound 1 and a glucocorticoid receptor agonist, an interleukin-1 receptor antagonist, or an interleukin-1β blocker provided herein could provide an alternative for patients who do not respond to other methods of treatment. In some embodiments, such other methods of treatment encompass treatment with GLEEVEC® (imatinib mesylate). In some embodiments, provided herein are methods of treatment of Ph+CML. In some embodiments, provided herein are methods of treatment of GLEEVEC® (imatinib mesylate) resistant Ph+CML. In some embodiments, provided herein is Compound I for use in methods of treatment of Ph+CML. In some embodiments, provided herein is Compound I for use in methods of treatment of GLEEVEC® (imatinib mesylate) resistant Ph+CML.

Also encompassed are methods of treating a subject regardless of the subject's age, although some diseases or disorders are more common in certain age groups. In some embodiments, the subject is at least 18 years old. In some embodiments, the subject is more than 18, 25, 35, 40, 45, 50, 55, 60, 65, or 70 years old. In other embodiments, the subject is less than 65 years old. In some embodiments, the subject is less than 18 years old. In some embodiments, the subject is less than 18, 15, 12, 10, 9, 8 or 7 years old.

In some embodiments, the methods may find use in subjects at least 50 years of age, although younger subjects could benefit from the method as well. In other embodiments, the subjects are at least 55, at least 60, at least 65, and at least 70 years of age. In another embodiment, the subject has a cancer with adverse cytogenetics. "Adverse cytogenetics" is defined as any nondiploid karyotype, or greater than or equal to 3 chromosomal abnormalities. In another embodiment, the subjects are at least 60 years of age and have a cancer with adverse cytogenetics. In another embodiment, the subjects are 60-65 years of age and have a cancer with adverse cytogenetics. In another embodiment, the subjects are 65-70 years of age and have a cancer with adverse cytogenetics.

In certain embodiments, the subject treated has no history of myocardial infarction within three months of treatment according to the methods provided herein. In some embodiments, the subject has no history of cerebrovascular accident or transient ischemic attack within three months of treatment according to the methods provided herein. In some embodiments, the subject has no suffered no thromboembelic event, including deep vein thrombosis or pulmonary embolus, within 28 days of treatment according to the methods provided herein. In other embodiments, the subject has not experienced or is not experiencing uncontrolled disseminated intravascular coagulation.

Because subjects with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual subject with cancer.

It will be appreciated that every suitable combination of the compounds provided herein with one or more of the aforementioned compounds and optionally one or more further pharmacologically active substances is contemplated herein.

Formulations of Compound 1

Exemplary formulations comprising Compound 1, for use in the methods provided herein, are described in U.S. Pat. No. 10,052,315 and US Publication No. US-2019-003018-A1, the disclosure of which is incorporated herein by reference in its entirety.

In one embodiment, the formulations of Compound 1 comprise a solid form of 2-(4-chlorophenyl)-N-((2-(2,6-dioxopiperidin-3-yl)-1-oxoisoindolin-5-yl)methyl)-2,2-difluoroacetamide. In one embodiment, the formulations of Compound 1 comprise an amorphous form of 2-(4-chlorophenyl)-N-((2-(2,6-dioxopiperidin-3-yl)-1-oxoisoindolin-5-yl)methyl)-2,2-difluoroacetamide.

In certain embodiments, the formulations are prepared with dimethylsulfoxide as a co-solvent or a processing aid. In certain embodiments, the formulations are prepared with formic acid as co-solvent or a processing aid. In certain embodiments, the formulations are prepared without any co-solvent or processing aid.

In certain embodiments, the formulations comprise dimethylsulfoxide as a co-solvent or a processing aid. In certain embodiments, the formulations comprise formic acid as a co-solvent or a processing aid. In certain embodiments, the formulations do not comprise any co-solvent or processing aid.

In certain embodiments, the formulations provided herein are lyophilized formulations. In certain embodiments, the formulations provided herein are reconstituted formulations obtained in a pharmaceutically acceptable solvent to produce a pharmaceutically acceptable solution.

Formulation Ia

In one embodiment, the formulations comprise Compound 1 in an amount of about 0.05-0.2%, a citrate buffer in an amount of about 3%-6%, and hydroxypropyl β-cyclodextrin (HPBCD) in an amount of about 92-98% based on total weight of the formulation.

In one embodiment, the formulations comprise Compound 1 in an amount of about 0.05-0.2%, a citrate buffer in an amount of about 3%-6%, and sulfobutyl ether-beta-cyclodextrin in an amount of about 92-98% based on total weight of the formulation.

In one embodiment, the formulations comprise Compound 1 in an amount of about 0.05-0.2%, a citrate buffer in an amount of about 3%-6%, HPBCD in an amount of about 92-98%, and no more than about 1% dimethyl sulfoxide based on total weight of the formulation.

In one embodiment, the formulations comprise Compound 1 in an amount of about 0.05-0.2%, a citrate buffer in an amount of about 3%-6%, sulfobutyl ether-beta-cyclodextrin in an amount of about 92-98%, and no more than about 1% dimethyl sulfoxide based on total weight of the formulation.

In one embodiment, the formulations comprise Compound 1 in an amount of about 0.08-0.15%, a citrate buffer in an amount of about 3%-6%, and HPBCD in an amount of about 94-96%, based on total weight of the formulation.

In one embodiment, the formulations comprise Compound 1 in an amount of about 0.08-0.15%, a citrate buffer in an amount of about 3%-6%, and sulfobutyl ether-beta-cyclodextrin in an amount of about 94-96%, and based on total weight of the formulation.

In one embodiment, the formulations comprise Compound 1 in an amount of about 0.08-0.15%, a citrate buffer in an amount of about 3%-6%, HPBCD in an amount of about 94-96%, and no more than about 1% dimethyl sulfoxide based on total weight of the formulation.

In one embodiment, the formulations comprise Compound 1 in an amount of about 0.08-0.15%, a citrate buffer in an amount of about 3%-6%, sulfobutyl ether-beta-cyclodextrin in an amount of about 94-96%, and no more than about 1% dimethyl sulfoxide based on total weight of the formulation.

In one aspect, the formulation provided herein comprises Compound 1 in an amount of about 0.08 to about 0.15% based on the total weight of the formulation. In certain embodiments, the amount of Compound 1 is from about 0.09% to about 0.15%, about 0.1% to about 0.13% or about 0.11% to about 0.12% based on the total weight of the formulation. In certain embodiments, the amount of Compound 1 is about 0.05%, 0.07%, 0.09%, 0.11%, 0.12%, 0.13%, or 0.15% based on the total weight of the formulation. In one embodiment, the amount of Compound 1 in the formulation is about 0.12% based on the total weight of the formulation.

In another aspect, provided herein is a formulation that comprises Compound 1 in an amount of about 0.5 mg to about 2 mg in a 20 cc vial. In still another aspect is a formulation that comprises Compound 1 in an amount of about 0.5 mg to about 1.5 mg, about 0.75 mg to about 1.25 mg, or about 0.8 mg to about 1.1 mg in a 20 cc vial. In one aspect Compound 1 is present in an amount of about 0.7, 0.75, 0.76, 0.8, 0.9, 1.0, 1.05 or 1.2 mg in a 20 cc vial. In one aspect Compound 1 is present in an amount of about 1.05 mg in a 20 cc vial.

In one aspect, the formulations provided herein contain a citrate buffer. In one aspect, the amount of citrate buffer in the formulations provided herein is from about 3% to about 6% based on total weight of the formulation. In one aspect, the amount of citrate buffer in the formulations provided herein is about 3%, 3.5%, 4%, 4.2%, 4.5% or 5% based on total weight of the formulation. In one aspect, the amount of citrate buffer in the formulations provided herein is about 4.2% based on total weight of the formulation. In one aspect, the amount of citrate buffer in the formulations provided herein is about 37 mg in a 20 cc vial.

In one embodiment, the citrate buffer comprises anhydrous citric acid and anhydrous sodium citrate. In certain embodiments, the amount of anhydrous citric acid is from about 1.5% to about 3%, about 1.75% to about 2.75%, or about 2% to about 2.5% based on total weight of the formulation. In certain embodiments, the amount of anhydrous citric acid in the formulation is about 1.5%, 1.75%, 2%, 2.1%, or 2.5% based on total weight of the formulation. In one embodiment, the amount of anhydrous citric acid in the formulation is about 2%, 2.1%, 2.22% or 2.3% based on total weight of the formulation. In one embodiment, the amount of anhydrous citric acid in the formulation is about 2.10% based on total weight of the formulation.

In still another aspect is a formulation that comprises anhydrous citric acid in an amount of about 16 mg to about 20 mg in a 20 cc vial. In one embodiment, the amount of anhydrous citric acid is about 16, 17, 18, 18.2, 18.4, 18.6, 18.8, 19 or 20 mg in a 20 cc vial. In one embodiment, the amount of anhydrous citric acid is about 18.6 mg in a 20 cc vial.

In certain embodiments, the amount of anhydrous sodium citrate is from about 1.5% to about 3%, about 1.75% to about 2.75%, or about 2% to about 2.5% based on total weight of the formulation. In certain embodiments, the amount of anhydrous sodium citrate in the formulation is about 1.5%, 1.75%, 2%, 2.1%, or 2.5% based on total weight of the formulation. In one embodiment, the amount of anhydrous sodium citrate in the formulation is about 2%, 2.05%, 2.08% or 2.1% based on total weight of the formulation. In one embodiment, the amount of anhydrous sodium citrate in the formulation is about 2.08% based on total weight of the formulation.

In still another aspect is a formulation that comprises anhydrous sodium citrate in an amount of about 16 mg to about 20 mg in a 20 cc vial. In one embodiment, the amount of anhydrous sodium citrate is about 16, 17, 18, 18.2, 18.4, 18.6, 18.8, 19 or 20 mg in a 20 cc vial. In one embodiment, the amount of anhydrous sodium citrate is about 18.4 mg in a 20 cc vial.

In certain embodiments, the amount of HPBCD in the formulations provided herein is about 94 to about 97% based on total weight of the formulation. In one embodiment, the amount of HPBCD in the formulations provided herein is about 94.5%, 95%, 95.5%, or 96% based on total weight of the formulation. In one embodiment, the amount of HPBCD in the formulations provided herein is about 95% based on total weight of the formulation.

In certain embodiments, the amount of sulfobutyl ether-beta-cyclodextrin in the formulations provided herein is about 94 to about 97% based on total weight of the formulation. In one embodiment, the amount of sulfobutyl ether-beta-cyclodextrin in the formulations provided herein is about 94.5%, 95%, 95.5%, or 96% based on total weight of the formulation. In one embodiment, the amount of sulfobutyl ether-beta-cyclodextrin in the formulations provided herein is about 95% based on total weight of the formulation.

In another aspect is a formulation that comprises HPBCD in an amount of about 800-900 mg in a 20 cc vial. In another aspect is a formulation that comprises HPBCD in an amount of about 810-880 mg, 820-860 mg or 830-850 mg in a 20 cc vial. In another aspect is a formulation that comprises HPBCD in an amount of about 840 mg in a 20 cc vial.

In another aspect is a formulation that comprises sulfobutyl ether-beta-cyclodextrin in an amount of about 800-900 mg in a 20 cc vial. In another aspect is a formulation that comprises sulfobutyl ether-beta-cyclodextrin in an amount of about 810-880 mg, 820-860 mg or 830-850 mg in a 20 cc vial. In another aspect is a formulation that comprises sulfobutyl ether-beta-cyclodextrin in an amount of about 840 mg in a 20 cc vial.

In another aspect is a formulation that comprises KLEPTOSE®HPB in an amount of about 840 mg in a 20 cc vial.

In one embodiment, the formulations comprise dimethyl sulfoxide in an amount of no more than about 1.5% based on total weight of the formulation. In one embodiment, the formulations comprise dimethyl sulfoxide in an amount of up to 0.1%, 0.2%, 0.3%, 0.4%, 0.6%, 0.7%, 0.8%, 0.9% or 1% based on total weight of the formulation. In one embodiment, the formulations comprise no more than about 0.1%, 0.2%, 0.3%, 0.4%, 0.6%, 0.7%, 0.8%, 0.9% or 1% dimethyl sulfoxide based on total weight of the formulation. In one embodiment, the formulations comprise dimethyl sulfoxide in an amount of up to about 0.1 to about 1.5% based on total weight of the formulation. In one embodiment, the amount of dimethyl sulfoxide in the formulations provided herein is about 0.1 to about 1.3% based on total weight of the formulation. In one embodiment, the amount of dimethyl sulfoxide in the formulations provided herein is about 0.1%, 0.2%, 0.3%, 0.4%, 0.6%, 0.7%, 0.8%, 0.9% or 1% based on total weight of the formulation. In one embodiment, the formulations provided herein do not contain any dimethyl sulfoxide. In one embodiment, the amount of dimethyl sulfoxide in the formulations provided herein is about 0.4% to 0.8% based on total weight of the formulation.

In another aspect is a formulation that comprises dimethyl sulfoxide in an amount of about 4 to 7 mg in a 20 cc vial. In another aspect is a formulation that comprises dimethyl sulfoxide in an amount of about 4.5-6.5 mg, or 5 to 6 mg in a 20 cc vial.

In certain embodiments, the formulation provided herein is lyophilized, and the lyophilized formulation upon reconstitution has a pH of about 4 to 5. In certain embodiments, the formulation upon reconstitution has a pH of about 4.2 to 4.4. In one embodiment, the lyophilized formulation upon reconstitution has a pH of about 4, 4.1, 4.2, 4.3, 4.4, 4.5, 4.6, 4.7, 4.8, 4.9 or 5.

In certain embodiments, the lyophilized formulation upon reconstitution has an osmolality of about 250-290 mOsm/kg. In certain embodiments, the lyophilized formulation upon reconstitution has an osmolality of about 260-280 mOsm/kg.

In certain embodiments, provided herein is a container comprising a formulation provided herein. In one aspect, the container is a glass vial. In one aspect, the container is a 20 cc glass vial.

In one aspect provided herein is a formulation in a 20 cc vial that comprises: Compound 1 at an amount that provides 1.05 mg 2-(4-chlorophenyl)-N-((2-(2,6-dioxopiperidin-3-yl)-1-oxoisoindolin-5-yl)methyl)-2,2-difluoroacetamide and a pharmaceutically acceptable carrier or excipient that includes a bulking agent as described herein. In one embodiment, the formulation further comprises no more than about 7 mg dimethyl sulfoxide as residual solvent. In one embodiment, the formulation comprises no more than about 6 mg dimethyl sulfoxide as residual solvent. In one embodiment, the formulation comprises no more than about 5 mg dimethyl sulfoxide as residual solvent. In one embodiment, the formulation comprises no more than about 4 mg dimethyl sulfoxide as residual solvent. In one embodiment, the formulation comprises from about 3 mg to about 7 mg, about 4 mg to about 6 mg, about 4 mg to about 5 mg or about 5 mg to about 6 mg dimethyl sulfoxide as residual solvent. In one embodiment, the formulation comprises about 4, 4.5, 5, 5.3, 5.5, 5.7, 6 or 6.5 mg dimethyl sulfoxide as residual solvent.

In one embodiment, the formulations consist essentially of Compound 1 in an amount of about 0.05-0.2%, a citrate buffer in an amount of about 3%-6%, and HPBCD in an amount of about 92-98% based on total weight of the formulation.

In one embodiment, the formulations consist essentially of Compound 1 in an amount of about 0.05-0.2%, a citrate buffer in an amount of about 3%-6%, and sulfobutyl ether-beta-cyclodextrin in an amount of about 92-98% based on total weight of the formulation.

In one embodiment, the formulations consist essentially of Compound 1 in an amount of about 0.05-0.2%, a citrate buffer in an amount of about 3%-6%, HPBCD in an amount of about 92-98%, and no more than about 1% dimethyl sulfoxide based on total weight of the formulation.

In one embodiment, the formulations consist essentially of Compound 1 in an amount of about 0.05-0.2%, a citrate buffer in an amount of about 3%-6%, sulfobutyl ether-beta-cyclodextrin in an amount of about 92-98%, and no more than about 1% dimethyl sulfoxide based on total weight of the formulation.

In one aspect, the formulation is in a 20 cc vial that comprises: Compound 1 at an amount that provides 1.05 mg 2-(4-chlorophenyl)-N-((2-(2,6-dioxopiperidin-3-yl)-1-oxoisoindolin-5-yl)methyl)-2,2-difluoroacetamide, a pharmaceutically acceptable carrier or excipient that includes a buffer and bulking agent as described herein, and about 5 mg to about 6 mg dimethyl sulfoxide as residual solvent. The buffer and bulking agent can be present at an amount as described herein.

In one aspect the formulation is in a 20 cc vial that comprises: Compound 1 at an amount that provides 1.05 mg 2-(4-chlorophenyl)-N-((2-(2,6-dioxopiperidin-3-yl)-1-oxoisoindolin-5-yl)methyl)-2,2-difluoroacetamide, 18.6 mg anhydrous citric acid, 18.4 mg anhydrous sodium citrate, 840 mg HPBCD, and about 5 mg to about 6 mg dimethyl sulfoxide as residual solvent as described herein. In one embodiment, the formulation in a 20 cc vial is reconstituted with 3.8 mL sterile water for injection.

In one aspect the formulation is in a 20 cc vial that consists essentially of: Compound 1 at an amount that provides 1.05 mg 2-(4-chlorophenyl)-N-((2-(2,6-dioxopiperidin-3-yl)-1-oxoisoindolin-5-yl)methyl)-2,2-difluoroacetamide, 18.6 mg anhydrous citric acid, 18.4 mg anhydrous sodium citrate, 840 mg HPBCD, and about 5 mg to about 6 mg dimethyl sulfoxide as residual solvent as described herein. In one embodiment, the formulation in a 20 cc vial is reconstituted with 3.8 mL sterile water for injection.

In one aspect the formulation is in a 20 cc vial that consists of: Compound 1 at an amount that provides 1.05 mg 2-(4-chlorophenyl)-N-((2-(2,6-dioxopiperidin-3-yl)-1-oxoisoindolin-5-yl)methyl)-2,2-difluoroacetamide, 18.6 mg anhydrous citric acid, 18.4 mg anhydrous sodium citrate, 840 mg HPBCD, and about 5 mg to about 6 mg dimethyl sulfoxide as residual solvent as described herein. In one embodiment, the formulation in a 20 cc vial is reconstituted with 3.8 mL sterile water for injection.

In one embodiment, provided herein is an aqueous formulation comprising Compound 1 in an amount of about 0.05-0.2% based on total weight of the solids, a citrate buffer in an amount of about 3%-6% based on total weight of the solids, HPBCD in an amount of about 92-98% based on total weight of the solids, and a diluent.

In one embodiment, provided herein is an aqueous formulation consisting essentially of Compound 1 in an amount of about 0.05-0.2% based on total weight of the solids, a citrate buffer in an amount of about 3%-6% based on total weight of the solids, HPBCD in an amount of about 92-98% based on total weight of the solids, and a diluent.

In one aspect provided herein is an aqueous formulation that comprises: Compound 1 at an amount that provides 1.05 mg 2-(4-chlorophenyl)-N-((2-(2,6-dioxopiperidin-3-yl)-1-oxoisoindolin-5-yl)methyl)-2,2-difluoroacetamide, 18.6 mg anhydrous citric acid, 18.4 mg anhydrous sodium citrate, 840 mg HPBCD, and about 5 mg to about 6 mg dimethyl sulfoxide as residual solvent and about 3.8 mL diluent.

In one aspect provided herein is an aqueous formulation that consists essentially of: Compound 1 at an amount that provides 1.05 mg 2-(4-chlorophenyl)-N-((2-(2,6-dioxopiperidin-3-yl)-1-oxoisoindolin-5-yl)methyl)-2,2-difluoroacetamide, 18.6 mg anhydrous citric acid, 18.4 mg anhydrous sodium citrate, 840 mg HPBCD, and about 5 mg to about 6 mg dimethyl sulfoxide as residual solvent and about 3.8 mL diluent.

In one aspect provided herein is an aqueous formulation that consists of: Compound 1 at an amount that provides 1.05 mg 2-(4-chlorophenyl)-N-((2-(2,6-dioxopiperidin-3-yl)-1-oxoisoindolin-5-yl)methyl)-2,2-difluoroacetamide, 18.6 mg anhydrous citric acid, 18.4 mg anhydrous sodium citrate, 840 mg HPBCD, and about 5 mg to about 6 mg dimethyl sulfoxide as residual solvent and about 3.8 mL diluent.

In certain embodiments, the formulation has a composition as described in Table A.

Formulation Ib

In one embodiment, the formulations comprise Compound 1 in an amount of about 0.01-0.15%, hydroxypropyl β-cyclodextrin in an amount of about 99.1-99.99%. In one embodiment, the formulations comprise Compound 1 in an amount of about 0.01-0.15%, hydroxypropyl β-cyclodextrin in an amount of about 99.1-99.99%, and no more than about 0.5% formic acid based on total weight of the formulation.

In one embodiment, the formulations comprise Compound 1 in an amount of about 0.05-0.25% and HPBCD in an amount of about 99.1-99.9% based on total weight of the formulation.

In one embodiment, the formulations comprise Compound 1 in an amount of about 0.05-0.25%, HPBCD in an amount of about 99.1-99.9%, and no more than about 0.5% formic acid based on total weight of the formulation.

In one embodiment, the formulations comprise Compound 1 in an amount of about 0.05-0.25% and HPBCD in an amount of about 99.75-99.9% based on total weight of the formulation.

In one embodiment, the formulations comprise Compound 1 in an amount of about 0.05-0.25%, HPBCD in an amount of about 99.75-99.9%, and no more than about 0.5% formic acid based on total weight of the formulation.

In one embodiment, the formulations comprise Compound 1 in an amount of about 0.05-0.25%, HPBCD in an amount of about 99.75-99.9%, and no more than about 0.2% formic acid based on total weight of the formulation.

In one embodiment, the formulations comprise Compound 1 in an amount of about 0.08-0.15% and HPBCD in an amount of about 99.8-99.9% based on total weight of the formulation.

In one embodiment, the formulations comprise Compound 1 in an amount of about 0.08-0.15%, HPBCD in an amount of about 99.8-99.9%, and no more than about 0.5% formic acid based on total weight of the formulation.

In one embodiment, the formulations comprise Compound 1 in an amount of about 0.08-0.15%, HPBCD in an amount of about 99.8-99.9%, and no more than about 0.12% formic acid based on total weight of the formulation.

In one embodiment, the formulations comprise Compound 1 in an amount of about 0.12% and HPBCD in an amount of about 99.88% based on total weight of the formulation.

In one embodiment, the formulations comprise Compound 1 in an amount of about 0.05-0.25% and sulfobutyl ether-beta-cyclodextrin in an amount of about 99.1-99.9%, based on total weight of the formulation.

In one embodiment, the formulations comprise Compound 1 in an amount of about 0.05-0.25%, sulfobutyl ether-beta-cyclodextrin in an amount of about 99.1-99.9%, and no more than about 0.5% formic acid based on total weight of the formulation.

In one embodiment, the formulations comprise Compound 1 in an amount of about 0.05-0.25% and sulfobutyl ether-beta-cyclodextrin in an amount of about 99.75-99.9%, based on total weight of the formulation.

In one embodiment, the formulations comprise Compound 1 in an amount of about 0.08-0.15% and sulfobutyl ether-beta-cyclodextrin in an amount of about 99.8-99.9% based on total weight of the formulation.

In one embodiment, the formulations comprise Compound 1 in an amount of about 0.08-0.15%, sulfobutyl ether-beta-cyclodextrin in an amount of about 99.8-99.9%, and no more than about 0.5% formic acid based on total weight of the formulation.

In one embodiment, the formulations comprise Compound 1 in an amount of about 0.12% and sulfobutyl ether-beta-cyclodextrin in an amount of about 99.88% based on total weight of the formulation.

In one aspect, the formulation provided herein comprises Compound 1 in an amount of about 0.08 to about 0.15% based on the total weight of the formulation. In certain embodiments, the amount of Compound 1 is from about 0.09% to about 0.15%, about 0.1% to about 0.13% or about 0.11% to about 0.12% based on the total weight of the formulation. In certain embodiments, the amount of Compound 1 is about 0.05%, 0.07%, 0.09%, 0.11%, 0.12%, 0.13%, or 0.15% based on the total weight of the formulation. In one embodiment, the amount of Compound 1 in the formulation is about 0.12% based on the total weight of the formulation.

In another aspect, the formulation comprises Compound 1 in an amount of about 0.5 mg to about 2 mg in a 20 cc vial. In still another aspect is a formulation that comprises Compound 1 in an amount of about 0.5 mg to about 1.5 mg, about 0.75 mg to about 1.25 mg, or about 0.8 mg to about 1.1 mg in a 20 cc vial. In one aspect Compound 1 is present in an amount of about 0.7, 0.75, 0.76, 0.8, 0.9, 1.0, 1.05 or 1.2 mg in a 20 cc vial. In one aspect Compound 1 is present in an amount of about 1 mg in a 20 cc vial.

In one embodiment, the amount of HPBCD in the formulations provided herein is about 97 to about 99.9% based on total weight of the formulation. In one embodiment, the amount of HPBCD in the formulations provided herein is about 98 to about 99.9% based on total weight of the formulation. In one embodiment, the amount of HPBCD in the formulations provided herein is about 99.1%, 99.3%, 99.5%, 99.7% or 99.9% based on total weight of the formulation. In one embodiment, the amount of HPBCD in the formulations provided herein is about 99.5% based on total weight of the formulation. In another aspect is a formulation that comprises HPBCD in an amount of about 750-850 mg in a 20 cc vial. In another aspect is a formulation that comprises HPBCD in an amount of about 790-840 mg, 780-830 mg or 790-810 mg in a 20 cc vial. In another aspect is a formulation that comprises HPBCD in an amount of about 800 mg in a 20 cc vial.

In another aspect is a formulation that comprises KLEPTOSE®HPB in an amount of about 800 mg in a 20 cc vial.

In one embodiment, the amount of sulfobutyl ether-beta-cyclodextrin in the formulations provided herein is about 97 to about 99.9% based on total weight of the formulation. In one embodiment, the amount of sulfobutyl ether-beta-cyclodextrin in the formulations provided herein is about 98 to about 99.9% based on total weight of the formulation. In one embodiment, the amount of sulfobutyl ether-beta-cyclodextrin in the formulations provided herein is about 99.1%, 99.3%, 99.5%, 99.7% or 99.9% based on total weight of the formulation. In one embodiment, the amount of sulfobutyl ether-beta-cyclodextrin in the formulations provided herein is about 99.5% based on total weight of the formulation.

In another aspect is a formulation that comprises sulfobutyl ether-beta-cyclodextrin in an amount of about 750-850 mg in a 20 cc vial. In another aspect is a formulation that comprises sulfobutyl ether-beta-cyclodextrin in an amount of about 790-840 mg, 780-830 mg or 790-810 mg in a 20 cc vial. In another aspect is a formulation that comprises sulfobutyl ether-beta-cyclodextrin in an amount of about 800 mg in a 20 cc vial.

In another aspect is a formulation that comprises KLEPTOSE®HPB in an amount of about 800 mg in a 20 cc vial.

In one embodiment, the formulations comprise formic acid in no more than about 0.5% based on total weight of the formulation. In one embodiment, the formulations comprise formic acid in an amount of up to about 0.05%, 0.07%, 0.09%, 0.1%, 0.2%, 0.3%, 0.4% or 0.5% based on total weight of the formulation. In one embodiment, the formulations comprise formic acid in no more than about 0.05%, 0.07%, 0.09%, 0.1%, 0.2%, 0.3%, 0.4% or 0.5% based on total weight of the formulation. In one embodiment, the amount of formic acid in the formulations provided herein is about 0.05 to about 0.5% based on total weight of the formulation. In one embodiment, the amount of formic acid in the formulations provided herein is about 0.05 to about 0.1% based on total weight of the formulation. In one embodiment, the amount of formic acid in the formulations provided herein is about 0.05%, 0.07%, 0.09%, 0.1%, 0.2%, 0.3%, 0.4% or 0.5% based on total weight of the formulation. In one embodiment, the formulations provided herein do not contain any formic acid. In one embodiment, the amount of formic acid in the formulations provided herein is about 0.05% to 0.09% based on total weight of the formulation.

In another aspect is a formulation that comprises formic acid in an amount of no more than about 1 mg in a 20 cc vial. In another aspect is a formulation that comprises formic acid in an amount of up to about 0.2, 0.5, 0.7, 0.9 mg or 1 mg in a 20 cc vial. In another aspect is a formulation that comprises formic acid in an amount of about 0.3-0.9 mg, or 0.4 to 0.8 mg in a 20 cc vial.

In another aspect, the formulation comprises Compound 1 in an amount of about 1 mg and HPBCD in an amount of about 800 mg in a 20 cc vial.

In another aspect, the formulation comprises Compound 1 in an amount of about 1 mg, HPBCD in an amount of about 800 mg and formic acid in an amount of about 0.9 mg in a 20 cc vial.

In certain embodiments, the formulation has a composition as described in Table A

TABLE A

Compositions of formulations Ia and Ib

|  | Formulation Ia* | Formulation Ib |
|---|---|---|
| Compound 1 | 1.05 mg/vial | 1.0 mg/vial |
| Citric acid anhydrous, USP | 18.6 mg/vial | — |
| Sodium citrate anhydrous, USP | 18.4 mg/vial | — |
| KLEPTOSE ® HPB (HP-β-CD), parenteral grade | 840 mg/vial | 800 mg/vial |
| Dimethyl sulfoxide (processing aid) | Partially removed upon drying | — |
| Formic acid (processing aid) | — | Partially removed upon drying |
| Water for injection (processing aid) | Removed upon drying | Removed upon drying |

*with 5% overfill

Formulation Ic

In one embodiment, the formulations comprise Compound 1 in an amount of about 0.01-0.08% and HPBCD in an amount of about 99.40-99.99% based on total weight of the formulation.

In one embodiment, the formulations comprise Compound 1 in an amount of about 0.01-0.08%, HPBCD in an amount of about 99.40-99.99%, and no more than about 0.5% formic acid based on total weight of the formulation.

In one embodiment, the formulations comprise Compound 1 in an amount of about 0.03-0.06% and HPBCD in an amount of about 99.60-99.99% based on total weight of the formulation.

In one embodiment, the formulations comprise Compound 1 from about 0.01 to about 0.08%, hydroxypropyl β-cyclodextrin from about 99.40% to about 99.99%, and formic acid from about 0.1 to about 0.3% based on total weight of the formulation In one aspect, the formulation provided herein comprises Compound 1 in an amount of about 0.02 to about 0.06% based on the total weight of the formulation. In certain embodiments, the amount of Compound 1 is from about 0.03% to about 0.06%, or about 0.04% to about 0.06% based on the total weight of the formulation. In certain embodiments, the amount of Compound 1 is about 0.03%, 0.04%, 0.05% or 0.06% based on the total weight of the formulation. In one embodiment, the amount of Compound 1 in the formulation is about 0.05% based on the total weight of the formulation.

In another aspect, provided herein is a formulation that comprises Compound 1 in an amount of about 0.75 mg to about 1.5 mg in a 20 cc vial. In still another aspect is a formulation that comprises Compound 1 in an amount of about 0.75 mg to about 1.25 mg in a 20 cc vial. In one aspect Compound 1 is present in an amount of about 0.75, 0.8, 0.9, 1.0, 1.05 or 1.2 mg in a 20 cc vial. In one aspect Compound 1 is present in an amount of about 1 mg in a 20 cc vial.

In one embodiment, the amount of HPBCD in the formulations provided herein is about 99.40 to about 99.99% based on total weight of the formulation. In one embodiment, the amount of HPBCD in the formulations provided herein is about 99.5, 99.6, 99.7, 99.8, 99.9, 99.95, or 99.99% based on total weight of the formulation. In another aspect is a formulation that comprises HPBCD in an amount of about 1800-1900 mg in a 20 cc vial. In another aspect is a formulation that comprises HPBCD in an amount of about 1850-1900 mg in a 20 cc vial. In another aspect is a formulation that comprises HPBCD in an amount of about 1875 mg in a 20 cc vial.

In one embodiment, the formulations comprise formic acid in no more than about 0.5% based on total weight of the formulation. In one embodiment, the formulations comprise formic acid in an amount of up to about 0.05%, 0.07%, 0.09%, 0.1%, 0.2%, 0.3%, 0.4% or 0.5% based on total weight of the formulation. In one embodiment, the formulations comprise formic acid in no more than about 0.05%, 0.07%, 0.09%, 0.1%, 0.2%, 0.3%, 0.4% or 0.5% based on total weight of the formulation. In one embodiment, the amount of formic acid in the formulations provided herein is about 0.05 to about 0.3% based on total weight of the formulation. In one embodiment, the amount of formic acid in the formulations provided herein is about 0.05 to about 0.25% based on total weight of the formulation. In one embodiment, the amount of formic acid in the formulations provided herein is about 0.05%, 0.07%, 0.09%, 0.1%, 0.2%, or 0.3% based on total weight of the formulation. In one embodiment, the formulations provided herein do not contain any formic acid. In one embodiment, the amount of formic acid in the formulations provided herein is about 0.11% to 0.3% based on total weight of the formulation.

In another aspect is a formulation that comprises formic acid in an amount of no more than about 4 mg in a 20 cc vial. In another aspect is a formulation that comprises formic acid in an amount of up to about 1, 1.8, 2, 2.1, 2.5, 3, 3.5, 3.8, 3.9, 4, 4.5, 4.9 mg or 5 mg in a 20 cc vial. In another aspect is a formulation that comprises formic acid in an amount of about 1-1.8 mg, 2.1-3.8 mg, or 3.9-4.9 mg in a 20 cc vial.

In another aspect, provided herein is a formulation that comprises Compound 1 in an amount of about 1 mg, and HPBCD in an amount of about 1875 mg in a 20 cc vial.

In another aspect, provided herein is a formulation that comprises Compound 1 in an amount of about 1 mg, HPBCD in an amount of about 1875 mg and formic acid in an amount of about 2.1-3.8 mg in a 20 cc vial.

In certain embodiments, the formulation has a composition as described in the Table B below:

TABLE B

|  | Formulation Ic |
|---|---|
| Compound 1 | 1.0 mg/vial |
| KLEPTOSE ® HPB (HP-β-CD), parenteral grade | 1875 mg/vial |
| Formic acid (in process solvent) | Partially removed upon drying |
| Water for injection (in process media) | Removed upon drying |

Formulations without Co-Solvent

In one embodiment, the formulations comprise Compound 1 in an amount of about 0.15-0.5%, a citrate buffer in an amount of about 15% to about 35%, and HPBCD in an amount of about 92% to about 98%, based on total weight of the formulation. In one embodiment, the citrate buffer comprises anhydrous citric acid and anhydrous sodium citrate.

In one embodiment, the formulations comprise Compound 1 in an amount of about 0.25-0.30%, a citrate buffer in an amount of about 30-32%, and HPBCD in an amount of about 67-69%, based on total weight of the formulation.

In one embodiment, the formulations comprise Compound 1 in an amount of about 0.30-0.33%, a citrate buffer in an amount of about 17-18%, and HPBCD in an amount of about 80-85%, based on total weight of the formulation.

Exemplary Formulations of Compound 1

In one embodiment, the formulations consist essentially of Compound 1 in an amount of about 0.05-0.25% and HPBCD in an amount of about 99.75-99.95% based on total weight of the formulation.

In one embodiment, the formulations consist essentially of Compound 1 in an amount of about 0.05-0.25% and HPBCD in an amount of about 99.75-99.99% based on total weight of the formulation.

In one embodiment, the formulations consist essentially of Compound 1 in an amount of about 0.05-0.25% and sulfobutyl ether-beta-cyclodextrin in an amount of about 99.75-99.95%, based on total weight of the formulation.

In one aspect, the formulation is in a 20 cc vial that comprises: Compound 1 at an amount that provides 1 mg 2-(4-chlorophenyl)-N-((2-(2,6-dioxopiperidin-3-yl)-1-oxoisoindolin-5-yl)methyl)-2,2-difluoroacetamide, 800 mg HPBCD, and about 0.6 mg formic acid as described herein. In one embodiment, the formulation in a 20 cc vial is reconstituted with 4.5 mL sterile water for injection.

In one aspect, the formulation is in a 20 cc vial that consists essentially of: Compound 1 at an amount that provides 1 mg 2-(4-chlorophenyl)-N-((2-(2,6-dioxopiperidin-3-yl)-1-oxoisoindolin-5-yl)methyl)-2,2-difluoroacetamide, 800 mg HPBCD, and about 0.6 mg formic acid as described herein. In one embodiment, the formulation in a 20 cc vial is reconstituted with 4.5 mL sterile water for injection.

In one aspect, the formulation is in a 20 cc vial that consists of: Compound 1 at an amount that provides 1 mg 2-(4-chlorophenyl)-N-((2-(2,6-dioxopiperidin-3-yl)-1-oxoisoindolin-5-yl)methyl)-2,2-difluoroacetamide, 800 mg HPBCD, and about 0.6 mg formic acid as described herein. In one embodiment, the formulation in a 20 cc vial is reconstituted with 4.5 mL sterile water for injection.

In one aspect, the formulation is in a 20 cc vial that comprises: Compound 1 at an amount that provides 1 mg 2-(4-chlorophenyl)-N-((2-(2,6-dioxopiperidin-3-yl)-1-oxoisoindolin-5-yl)methyl)-2,2-difluoroacetamide, 800 mg sulfobutyl ether-beta-cyclodextrin, and about 0.6 mg formic acid as described herein. In one embodiment, the formulation in a 20 cc vial is reconstituted with 4.5 mL sterile water for injection.

In one aspect, the formulation is in a 20 cc vial that consists essentially of: Compound 1 at an amount that provides 1 mg 2-(4-chlorophenyl)-N-((2-(2,6-dioxopiperidin-3-yl)-1-oxoisoindolin-5-yl)methyl)-2,2-difluoroacetamide, 800 mg sulfobutyl ether-beta-cyclodextrin, and about 0.6 mg formic acid as described herein. In one embodiment, the formulation in a 20 cc vial is reconstituted with 4.5 mL sterile water for injection.

In one aspect, the formulation is in a 20 cc vial that consists of: Compound 1 at an amount that provides 1 mg 2-(4-chlorophenyl)-N-((2-(2,6-dioxopiperidin-3-yl)-1-oxoisoindolin-5-yl)methyl)-2,2-difluoroacetamide, 800 mg sulfobutyl ether-beta-cyclodextrin, and about 0.6 mg formic acid as described herein. In one embodiment, the formulation in a 20 cc vial is reconstituted with 4.5 mL sterile water for injection.

In one aspect, the formulation is in a 20 cc vial that comprises: Compound 1 at an amount that provides 1 mg 2-(4-chlorophenyl)-N-((2-(2,6-dioxopiperidin-3-yl)-1-oxoisoindolin-5-yl)methyl)-2,2-difluoroacetamide, 1875 mg HPBCD, and about 2.1-3.8 mg formic acid as described herein. In one embodiment, the formulation in a 20 cc vial is reconstituted with 12.5 ml Normal Saline for injection.

In one aspect, the formulation is in a 20 cc vial that consists essentially of: Compound 1 at an amount that provides 1 mg 2-(4-chlorophenyl)-N-((2-(2,6-dioxopiperidin-3-yl)-1-oxoisoindolin-5-yl)methyl)-2,2-difluoroacetamide, 1875 mg HPBCD, and about 2.1-3.8 mg formic acid as described herein. In one embodiment, the formulation in a 20 cc vial is reconstituted with 12.5 ml Normal Saline for injection.

In one aspect, the formulation is in a 20 cc vial that consists of: Compound 1 at an amount that provides 1 mg 2-(4-chlorophenyl)-N-((2-(2,6-dioxopiperidin-3-yl)-1-oxoisoindolin-5-yl)methyl)-2,2-difluoroacetamide, 1875 mg HPBCD, and about 2.1-3.8 mg formic acid as described herein. In one embodiment, the formulation in a 20 cc vial is reconstituted with 12.5 ml Normal Saline for injection.

In one embodiment, the methods provided herein comprise administering an aqueous formulation comprising Compound 1 in an amount of about 0.05-0.25% based on total weight of the solids, and HPBCD in an amount of about 99.1-99.9% based on total weight of the solids, and a diluent.

In one embodiment, the methods provided herein comprise administering an aqueous formulation comprising Compound 1 in an amount of about 0.05-0.25% based on total weight of the solids, and HPBCD in an amount of about 99.75-99.95% based on total weight of the solids, and a diluent.

In one embodiment, the methods provided herein comprise administering an aqueous formulation consisting essentially of Compound 1 in an amount of about 0.05-0.25% based on total weight of the solids, and HPBCD in an amount of about 99.75-99.95% based on total weight of the solids, and a diluent.

In one aspect, the methods provided herein comprise administering an aqueous formulation that comprises: Compound 1 at an amount that provides 1 mg 2-(4-chlorophenyl)-N-((2-(2,6-dioxopiperidin-3-yl)-1-oxoisoindolin-5-yl)methyl)-2,2-difluoroacetamide, 800 mg HPBCD, about 0.6 mg formic acid and about 4.5 mL diluent.

In one aspect, the methods provided herein comprise administering an aqueous formulation that consists of: Compound 1 at an amount that provides 1 mg 2-(4-chlorophenyl)-N-((2-(2,6-dioxopiperidin-3-yl)-1-oxoisoindolin-5-yl)methyl)-2,2-difluoroacetamide, 800 mg HPBCD, about 0.6 mg formic acid and about 4.5 mL diluent.

In one embodiment, the methods provided herein comprise administering an aqueous formulation comprising Compound 1 in an amount of about 0.01-0.08% based on total weight of the solids, and HPBCD in an amount of about 99.50-99.99% based on total weight of the solids, and a diluent.

In one embodiment, the methods provided herein comprise administering an aqueous formulation comprising Compound 1 in an amount of about 0.01-0.08% based on total weight of the solids, and HPBCD in an amount of about 99.50-99.99% based on total weight of the solids, and a diluent.

In one embodiment, the methods provided herein comprise administering an aqueous formulation consisting essentially of Compound 1 in an amount of about 0.01-0.08% based on total weight of the solids, and HPBCD in an amount of about 99.50-99.99% based on total weight of the solids, and a diluent.

In one aspect, the methods provided herein comprise administering an aqueous formulation that comprises: Compound 1 at an amount that provides 1 mg 2-(4-chlorophenyl)-N-((2-(2,6-dioxopiperidin-3-yl)-1-oxoisoindolin-5-yl)methyl)-2,2-difluoroacetamide, 800 mg HPBCD, about 0.6 mg formic acid and about 4.5 mL diluent.

In one aspect, the methods provided herein comprise administering an aqueous formulation that consists of: Compound 1 at an amount that provides 1 mg 2-(4-chlorophenyl)-N-((2-(2,6-dioxopiperidin-3-yl)-1-oxoisoindolin-5-yl)methyl)-2,2-difluoroacetamide, 800 mg HPBCD, about 0.6 mg formic acid and about 4.5 mL diluent.

In certain embodiments, the formulation has a composition as described in the Table A. In certain embodiments, the formulation has a composition as described in the Table B.

In certain embodiments, the methods provided herein comprise administering a lyophilized formulation, wherein the lyophilized formulation upon reconstitution has a pH of about 2.5 to 4. In certain embodiments, the lyophilized formulation upon reconstitution has a pH of about 2.5 to 3.5. In certain embodiments, the lyophilized formulation upon reconstitution has a pH of about 3.0 to 3.6. In one embodiment, the lyophilized formulation upon reconstitution has a pH of about 2.5, 3, 3.2, 3.4, 3.6, 3.8 or 4. In one embodiment, the lyophilized formulation upon reconstitution has a pH of about 2.5, 2.8, 3, 3.2, 3.4, 3.6, 3.8 or 4.

In certain embodiments, the lyophilized formulation upon reconstitution has an osmolality of about 260-290 mOsm/kg. In certain embodiments, the lyophilized formulation upon reconstitution has an osmolality of about 280 mOsm/kg. In certain embodiments, the lyophilized formulation upon reconstitution has an osmolality of about 260-370 mOsm/kg. In certain embodiments, the lyophilized formulation upon reconstitution has an osmolality of about 360 mOsm/kg. In certain embodiments, the lyophilized formulation upon reconstitution has an osmolality of about 350-450 mOsm/kg. In certain embodiments, the lyophilized formulation upon reconstitution has an osmolality of about 416 mOsm.

In certain embodiments, the lyophilized formulation is reconstituted with half normal saline (0.45% sodium chloride sterile solution for injection) and has an osmolality of about 280-320 mOsm/kg upon reconstitution. In certain embodiments, the lyophilized formulation is reconstituted with half normal saline (0.45% sodium chloride sterile solution for injection), and has a pH of 3.0-3.2 and an osmolality of about 280-320 mOsm/kg upon reconstitution. In certain embodiments, the lyophilized formulation is reconstituted with 4.5 mL of half normal saline (0.45% sodium chloride sterile solution for injection), and has a pH of 3.0-3.2 and an osmolality of about 280-320 mOsm/kg upon reconstitution. In one embodiment, the reconstituted solution of the required dose is diluted with normal saline (0.9% sodium chloride sterile solution for injection) in an infusion bag to a volume to 50 mL for 30-minute intravenous administration.

In certain embodiments, the lyophilized formulation is reconstituted with normal saline and has an osmolality of about 440 mOsm/kg upon reconstitution. In one embodiment, the reconstituted solution of the required dose is diluted with normal saline to a volume to 50 mL to obtain a dosing solution having an osmolality of about 310-380 mOsm/kg. In one embodiment, the reconstituted solution of the required dose is diluted with normal saline to a volume to 50 mL to obtain a dosing solution having an osmolality of about 310-355 mOsm/kg. In one embodiment, the reconstituted solution of the required dose is diluted with normal saline to a volume to 50 mL to obtain a dosing solution having an osmolality of about 317-371 mOsm/kg. In one embodiment, the reconstituted solution of the required dose is diluted with normal saline to a volume to 50 mL to obtain a dosing solution having an osmolality of about 317 mOsm/kg. In one embodiment, the reconstituted solution of the required dose is diluted with normal saline to a volume to 50 mL to obtain a dosing solution having an osmolality of about 371 mOsm/kg. In one embodiment, the osmolality of the dosing solution is no more than 352 mOsm/kg. In one embodiment, the osmolality of the dosing solution having a dose of 4.8 mg Compound 1 is 352 mOsm/kg.

In certain embodiments, the formulation is provided in a glass vial, for example, 20 cc glass vial.

In one aspect, the methods provided herein comprise administering a formulation in a 20 cc vial that comprises: Compound 1 at an amount that provides 1 mg 2-(4-chlorophenyl)-N-((2-(2,6-dioxopiperidin-3-yl)-1-oxoisoindolin-5-yl)methyl)-2,2-difluoroacetamide, and a bulking agent as described herein. In one embodiment, the formulation further comprises no more than about 5 mg formic acid as residual solvent. In one embodiment, the formulation further comprises no more than about 4 mg formic acid as residual solvent. In one embodiment, the formulation further comprises no more than about 3 mg formic acid as residual solvent. In one embodiment, the formulation further comprises no more than about 2 mg formic acid as residual solvent. In one embodiment, the formulation further comprises no more than about 1.5 mg formic acid as residual solvent. In one embodiment, the formulation further comprises no more than about 1 mg formic acid as residual solvent. In one embodiment, the formulation further comprises no more than about 0.8 mg formic acid as residual solvent. In one embodiment, the formulation comprises from about 0.4 mg to about 1.5 mg, about 0.5 mg to about 1 mg, or about 0.5 mg to about 0.9 mg formic acid as residual solvent. In one embodiment, the formulation comprises about 0.4 mg, about 0.6 mg, about 0.8 mg, about 1 mg or about 1.5 mg formic acid as residual solvent. In one embodiment, the formulation comprises formic acid as residual solvent in an amount from about 1.0 mg/mg of Compound 1 to about 1.8 mg/mg of Compound 1, about 2.1 mg/mg of Compound 1 to about 3.8 mg/mg of Compound 1, or about 3.9 mg/mg of Compound 1 to about 4.9 mg/mg of Compound 1.

The formulations of Compound 1 can be administered to a patient in need thereof using standard therapeutic methods for delivering Compound 1 including, but not limited to, the methods described herein. In one embodiment, the formulations are reconstituted in a pharmaceutically acceptable solvent to produce a pharmaceutically acceptable solution, wherein the solution is administered (such as by intravenous injection) to the patient.

In one aspect, the formulations are lyophilized, and the lyophilized formulations are suitable for reconstitution with a suitable diluent to the appropriate concentration prior to administration. In one embodiment, the lyophilized formulation is stable at room temperature. In one embodiment, the lyophilized formulation is stable at room temperature for up to about 24 months. In one embodiment, the lyophilized formulation is stable at room temperature for up to about 24 months, up to about 18 months, up to about 12 months, up to about 6 months, up to about 3 months or up to about 1 month. In one embodiment, the lyophilized formulation is stable upon storage under accelerated condition of 40° C./75% RH for up to about 12 months, up to about 6 months or up to about 3 months.

The lyophilized formulation can be reconstituted for parenteral administration to a patient using any pharmaceutically acceptable diluent. Such diluents include, but are not limited to Sterile Water for Injection (SWFI), Dextrose 5% in Water (D5W), or a cosolvent system. Any quantity of diluent may be used to reconstitute the lyophilized formulation such that a suitable solution for injection is prepared. Accordingly, the quantity of the diluent must be sufficient to dissolve the lyophilized formulation. In one embodiment, 1-5 mL or 1 to 4 mL of a diluent are used to reconstitute the lyophilized formulation to yield a final concentration of, about 0.05-0.3 mg/mL or about 0.15-0.25 mg/mL of Compound 1. In certain embodiments, the final concentration of Compound 1 in the reconstituted solution is about 0.25 mg/mL. In certain embodiments, the final concentration of Compound 1 in the reconstituted solution is about 0.20 mg/mL. In certain embodiments, the volume of the reconstitution diluent varies between 3 ml and 5 ml to yield a final concentration of 0.15-0.3 mg/mL. In certain embodiments, depending on the required dose, multiple vials may be used for reconstitution.

The reconstituted solutions of lyophilized formulation can be stored and used within up to about 24 hours, about 12 hours or about 8 hours. In one embodiment, the reconstituted aqueous solution is stable at room temperature from about 1-24, 2-20, 2-15, 2-10 hours upon reconstitution. In one embodiment, the reconstituted aqueous solution is stable at room temperature for up to about 20, 15, 12, 10, 8, 6, 4 or 2 hours upon reconstitution. In some embodiments, the solution is used within 8 hours of preparation. In some embodiments, the solution is used within 5 hours of preparation. In some embodiments, the solution is used within 1 hour of preparation.

Evaluation of Activity

Standard physiological, pharmacological and biochemical procedures are available for testing the compounds to identify those that possess the desired activity.

Such assays include, for example, cell based assays, including the assay described in the Example section.

Embodiments provided herein may be more fully understood by reference to the following examples. These examples are meant to be illustrative of pharmaceutical compositions and dosage forms provided herein, but are not in any way limiting.

EXAMPLES

The following Examples are presented by way of illustration, not limitation. The following abbreviations are used in descriptions and examples.

| Abbreviation or Specialist Term | Explanation or Definition |
|---|---|
| AML | acute myeloid leukemia |
| ATF4 | activating transcription factor 4 |
| BMMC | bone marrow mononuclear cell |
| cCasp3/7 | cleaved caspase 3 and 7 |
| CHOP | CCAAT/enhancer-binding protein homologous protein |
| CK1a | casein kinase 1 |
| CRBN | cereblon |
| CTG | CELL TITER-GLO ® |
| DMSO | dimethylsulfoxide |
| D5W | Dextrose 5% in Water |
| $EC_{50}$ | concentration producing 50% activity |
| eRF3 | eukaryotic translation termination factor 3 |
| FAB | French-American-British |
| GSPT1 | G1 to S phase transition 1 |
| HPβCD or HPBCD | Hydroxypropyl-beta-cyclodextrin |
| $IC_{50}$ | concentration resulting in 50% inhibition |
| IL | interleukin |

| Abbreviation or Specialist Term | Explanation or Definition |
|---|---|
| ISR | Integrated stress response |
| Log2FC | log2 fold change |
| LPS | lipopolysaccharide |
| MSD | Meso Scale Discovery |
| NA | not applicable |
| NLRP3 | NACHT, LRR and PYD domains-containing protein 3 |
| NMD | nonsense-mediated mRNA decay |
| PABP | poly(A)-binding protein |
| PARP | PARP = poly (ADP-ribose) polymerase |
| PBS | phosphate buffered saline |
| rh-IL | recombinant human-interleukin |
| RLU | Relative Luminescence Units |
| RNAseq | RNA sequencing |
| RPM | revolutions per minute |
| SBEβCD | Sulfobutylether-β-cyclodextrin sodium salt |
| SDS PAGE | sodium dodecyl sulfate polyacrylamide gel electrophoresis |
| SoC | Standard of Care |
| SWFI | Sterile Water for Injection |
| TKI | tyrosine kinase inhibitor |
| tRNA | transfer ribonucleic acid |
| Ub | ubiquitin |
| UPR | unfolded protein response |
| WFI | Water for injection |

"Compound 1, Form C" or "Form C" or "API" in the Examples herein refers to polymorph Form C of 2-(4-chlorophenyl)-N-((2-(2,6-dioxopiperidin-3-yl)-1-oxoisoindolin-5-yl)methyl)-2,2-difluoroacetamide. "Compound 1, Form A" or "Form A" in the Examples herein refers to polymorph Form A of 2-(4-chlorophenyl)-N-((2-(2,6-dioxopiperidin-3-yl)-1-oxoisoindolin-5-yl)methyl)-2,2-difluoroacetamide. The physical and chemical properties of 2-(4-chlorophenyl)-N-((2-(2,6-dioxopiperidin-3-yl)-1-oxoisoindolin-5-yl)methyl)-2,2-difluoroacetamide are summarized in Table 1.

TABLE 1

Summary of physical and chemical properties of 2-(4-chlorophenyl)-N-((2-(2,6-dioxopiperidin-3-yl)-1-oxoisoindolin-5-yl)methyl)-2,2-difluoroacetamide

| | |
|---|---|
| Structure | 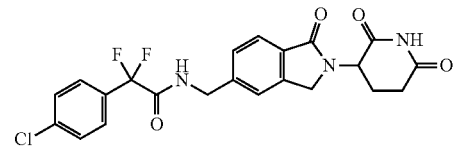 [SMILES: O=C1CCC(N2Cc3cc(CNC(=O)C(F)(F)c4ccc(Cl)cc4)ccc3C2=O)C(=O)N1] |
| Molecular Formula | $C_{22}H_{18}ClF_2N_3O_4$ |
| Molecular Weight | 461.85 |
| Log D | cLogP = 2.18 (Log D not measured due to solubility) |
| pKa | cpKa = 10.66 (Not measured due to low stability above pH 7) |
| Melting Point | 234° C. (Form C) |
| Appearance | White powder |
| Solubility | Practically insoluble in water (≤1 µg/ml across pH range of 1-8) |
| Solid State Stability | DS is physically stable under all storage conditions. |
| Solution Stability | DS is not stable in solution at pH of 5.0 or above. Hydrolysis is the major degradation pathway. |
| Hygroscopicity | Not hygroscopic |
| Pharmaceutical Form | Crystalline; Anhydrous; five polymorph forms |

Compound and Treatment Procedures

For CELL TITER-GLO® (CTG; Promega) and Incucyte assays, cells were seeded at 0.1 million per mL, 50 µL per well of Corning black 384-well plate and allowed set overnight. The next day, test compounds were dispensed using a Tecan D300e digital dispenser according to manufacturer's instruction.

For cytokine assays on AML cell lines, cells were seeded at 1 million per mL, 3 mL per well of 6-well plates and allowed set overnight. The next day, cells were treated with 3 μL 1000× working stock of compounds of interest.

For cytokine assays on primary AML and healthy bone marrow cells, cells were seeded at 0.2 million in 150 μL media per well of ultra-low attachment 96-well plate in duplicates. Cell culture media was collected 24 and 48 hours post-treatment with Compound 1 and/or LPS. Cells were pelleted, fixed in 1.6% PFA and froze down for flow cytometry analysis.

Test articles include: Compound 1, Thapsigargin (Sigma, Cat No. T9033-5MG), bortezomib (Selleckchem Cat No. S1013), Cyclohexamide (Abcam, Cat No. ab120093), Cytarabine (Sigma, Cat No. C1768), Daunorubicin HCl (Selleckchem Cat No. S3035), gilteritinib (Selleckchem Cat No. S7754), fedratinib (MedChem Express, Cat No. HY-10409), homoharringtonine (Abcam, Cat No. ab142580), venetoclax (Selleckchem Cat No. S8048), dexamethasone (Selleckchem Cat No. S1322), Z-VAD-FMK (Selleckchem Cat No. S7023), Z-IETD-FMK (Selleckchem Cat No. S7023), Y-YAD-FMK (Abcam Cat No. ab141388), VRT-043198 (Medkoo Bioscience, Cat No. 205941).

Cell Culture and Materials

Human AML cell lines, HL-60 (CCL-240), KG-1 (CCL-246), ML-2 (ACC-15), MOLM-13 (ACC-554), MV-4-11 (CRL-9591), NOMO-1 (ACC-542), TF-1 (CRL-2003), THP-1 (TIB-202), and U937 (CRL-1593) were obtained from American Type Culture Collection (ATCC; Manassas, VA) or Deutsche Sammlung von Mikroorganismen and Zellkulturen (DSMZ, Germany) cell banks. Acute myeloid leukemia cell lines were maintained in RPMI-1640 (ATCC Cat No. 30-2001) containing 20% fetal bovine serum (FBS) (Corning Cat No. 35-010-CV) and maintained in humidified incubators at 5% carbon dioxide.

Normal PBMCs were purchased from AllCells (Cat No. PB006F). Primary AML BMMC in were purchased from Conversant (SKU ID: BBM1000-E1110036458110215SH) or Fidelis Research (AML55, AML57, AML73, AML74, AML76, AML79, AML80, AML81, AML84, AML95). Bone marrow from health donor was purchased from StemCell Technologies (Cat No. 70001.2).

Normal PBMCs were cultured in RPMI-1640 (ATCC Cat No. 30-2001) containing 20% fetal bovine serum (Corning Cat No. 35-010-CV). Primary AML and bone marrows were cultured in Complete Medium Cytokines 1X: StemSpam™ Serum-Free Expansion Medium (StemCell Technologies Cat No. 09650) supplemented with 50 ng/mL Stem Cell Factor (Peprotech Cat No. 300-07), 50 ng/mL recombinant Human FLT3-Ligand (Peprotech Cat No. 300-19), 20 ng/mL recombinant human-interleukin-3 (Peprotech Cat No. 200-03), 20 ng/μL recombinant human-interleukin-6 (Peprotech Cat No. 200-06), 1 μM StemRegenin (StemCell Technologies Cat No. 72342), penicillin/streptomycin (Invitrogen Cat No. 15140122).

Cell Proliferation and Apoptosis Assays

AML cell lines and primary AML were treated in duplicate or triplicates with DMSO or test compounds in 384-well plates for 3 days. Cell viability was determined by CELL TITER-GLO® (CTG; Promega) assay kit according to manufacturer's instructions. Apoptosis was monitored using Caspase 3/7 Green reagent (Essen Biosciences Cat No. 4440). Caspase-3/7 activation levels were quantified using the IncuCyte™ ZOOM basic analyzer.

Immunoblot Analysis

Cells were washed in ice-cold 1×PBS twice before harvest in Cell Extraction Buffer (ThermoFisher Cat No. FNN0011) supplemented with 1× Halt Protease Inhibitor Cocktail (ThermoFisher Cat No. 78429). Whole cell extracts were collected after centrifugation at 14,000 g for 10 minutes, resolved on 4-12% Bis-Tris Novex Precast Gels (ThermoFisher Cat No. WG1403A), transferred onto a nitrocellulose membrane using the Turboblot Turbo Transfer System (Bio-Rad), and probed with the indicated primary antibodies. Bound antibodies were detected with IRDye-680 or -800 conjugated secondary antibodies using a LI-COR scanner.

Antibodies used for immunoblot: mouse anti-human GSPT-1 mAb conjugated with AL647 (clone number GSPT1-164-17G9-G6, Celgene, San Diego, CA), IL-1β (R&D Systems, Cat No. AF-201-NA), cleaved caspase 3 (Cell Signaling, Cat No. 9664S), alpha-tubulin (Cell Signaling, Cat No. 3873S), cleaved Caspase-8 (Cell Signaling, Cat No. 9748S), Caspase-1 (Cell Signaling, Cat No. 3866S), HA tag (Cell Signaling, Cat No. 3724), phosphor-eIF2a (Cell Signaling, Cat No. 9721), total eIF2a (Cell Signaling, Cat No. 9722), ATF4 (Cell Signaling, Cat No. 11815S), CHOP (Abcam, Cat No. 11419), GAPDH (Cell Signaling, Cat No. 5174), rabbit anti-mouse 800 antibody (LI-COR Biosciences), rabbit anti-mouse 680 antibody (LI-COR Biosciences), mouse anti-rabbit 680 antibody (LI-COR Biosciences), mouse anti-rabbit 800 antibody (LI-COR Biosciences)

Flow Cytometry Analysis

Sample processing for flow cytometry was performed in 96 well plates. One million cells per well were washed with 300 μL ice cold staining buffer (BD, Cat No. 554723) and blocked with 150 μL Fc blocking buffer (Miltenyi, Cat No. 130-059-901) for 10 minutes at room temperature. After blocking, cells were washed once with perm/wash buffer (BD, Cat No. 554723) and stained with 100 μL primary antibody diluted in perm/wash buffer for 20 min on ice in the dark. After staining, cells were washed in 300 μL staining buffer then resuspended in 300 μL staining buffer before being analyzed using a BD Fortessa machine.

Antibodies used for flow cytometry: Mouse anti-human GSPT-1 mAb (clone number GSPT1-164-17G9-G6, Celgene, San Diego, CA), CD14-BUV737 (BD Biosciences, Cat No. 564445), CD3 (BD Biosciences, Cat No. 564000), CD34 (BD Biosciences, Cat No. 348791), CD45 (BD Biosciences, Cat No. 340953), cleaved caspase-8 (Cell Signaling, Cat No. 12602S), cleaved caspase-3 (BD Biosciences, Cat No. 564094), human IL-1β (R&D Systems, Cat No. IC201S), human IL-1β (R&D Systems, Cat No. IC8406A)

Electrochemiluminescence Assay

IL-1α (Meso Scale Disgnostics, Cat No. K151RBD), IL-1β (Meso Scale Disgnostics, Cat No. K151QPD), IL-1RA (Meso Scale Disgnostics, Cat No. K151WTD), IL-18 (Meso Scale Disgnostics, Cat No. K151VJK), TNFa (Meso Scale Disgnostics, Cat No. K151QWD), VEGF Meso Scale Disgnostics, Cat No. K151RHD) levels were measured by (Meso Scale Disgnostics assay kits following manufacturer's instructions. Measurements were made on a MESO™ SECTOR S 600 plate reader (Meso Scale Disgnostics).

Data Analysis

Cell proliferation (CTG) and caspase 3/7 activation (In-cuCyte) were analyzed using GraphPad Prism. Electrochemiluminescence data was analyzed using MSD Discovery Workbench platform.

Example 1: Interleukin-1β Induction by Compound 1

Figure 1C:
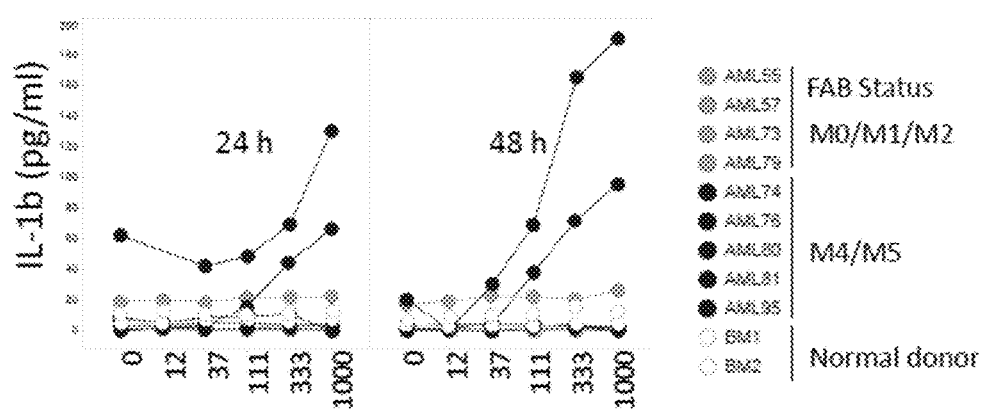

The level of intracellular pro IL-1β and released IL-1β in eight AML cell lines and normal PBMC treated with a titration of Compound 1 over a 48 hour period was assessed. (see FIGS. 1A-1C, Table 2). Supernatant IL-1βb level was induced over 5 fold in 6 out of 8 AML cell lines and normal PBMC upon Compound 1 treatment compared to DMSO (FIGS. 1A, 1B, and 1C, Table 2). Such induction occurred post-GSPT1 degradation and caspase 3 activation (FIG. 1A), suggesting a cell death associated phenomenon. In ML-2 cells, for instance, a significant reduction of GSPT1 occurred at two high doses of Compound 1 at 24 hours (FIG. 1A), accompanied with a concurrent induction of cleaved caspase 3 (FIG. 1A). However, intracellular pro- and secreted IL-1β induction was not observed until 48 hours post-treatment (FIGS. 1A, and 1B). The temporal relationship between apoptosis and IL-1β was observed in all cell lines where IL-1β induction was observed.

IL-1β can be induced in monocytic cells as a part of the innate immune response (Gaidt et al. *Immunity.* 2016, 44(4): 833-46, Carta et al. *J Biol Chem.* 2011, 286(31):27069-80, Netea et al. *Blood.* 2009, 113(10):2324-35). In vitro (Table 2), most cell lines (ML-2, MV4-11, NOMO-1, MOLM13) exhibiting IL-1β induction by Compound 1 are monocytic in lineage (FAB4/5 status) with one exception (KG-1). To extend the cell line study, IL-1β levels in response to Compound 1 in bone marrow mononuclear cells (BMMC) from 9 primary AML patients were tested, including five monocytic (FAB M4/M5) and four non-monocytic (FAB M0/M1/M2) AML (FIG. 1C). BMMC from 2 healthy donors were included as references. Normal and AML BMMC were treated with a dose range of Compound 1, and IL-1β in cell culture supernatant was measured at 24 hours and 48 hours post treatment. Two out of five samples from M4/M5 classification showed a marked induction of IL-1β in response to Compound 1 at both 24 and 48 hours post treatment. In contrast, Compound 1 was not able to induce IL-1β in any of the four M0/M1/M2 samples.

The maturation of IL-1β can be mediated through classical caspase-1 inflammasome pathway, or a caspase-8 dependent non-canonical inflammasome signaling (Antonopoulos et al. *J Biol Chem.* 2015, 290(33):20167-84; Chauhan et al. *Cell Rep.* 2018, 25(9):2354-2368; and Schneider et al. *Cell Rep.* 2017, 21(13):3846-3859). To understand if classical caspase-1 mediated inflammasome pathway was activated by Compound 1, the levels of an inflammasome marker, IL-18, were tested in response to Compound 1 (FIG. 1B, Table 1), using a known inflammasome stimulant lipopolysaccharide (LPS) as positive control. Compound 1 induced IL-1α, IL-1β and IL-1RA post-apoptosis without significantly increased the levels of IL-18 in most cell lines tested. In contrast, LPS conferred profound IL-18 induction at early time point (6 hrs), followed by IL-1β, IL-1α and IL-1RA at later time point (FIG. 1B). These results suggest IL-1β induction by Compound 1 is through a distinct mechanism from that of LPS.

TABLE 2

Summary of Interleukin-1β and Interleukin-18 Induction from 8 Acute Myeloid Leukemia Cell Lines and Normal Peripheral Blood Mononuclear Cells

| | | | | | IL-1β | | IL-18 | |
| --- | --- | --- | --- | --- | --- | --- | --- | --- |
| Cell Line | Cell Type | FAB | M4/5 | Compound 1 IC50 | LPS | Compd 1 | LPS | Compd 1 |
| KG-1 | myeloblast | M0 | N | 8.9 | 17.67 | 27.17 | 3.47 | 0.38 |
| ML-2 | monocytic | M4 | Y | 15.12 | 8.70 | 3.48 | 1.21 | 0.00 |
| MV4-11 | macrophage | M5 | Y | 17.27 | 65.19 | 16.46 | 24.45 | 0.00 |
| NOMO-1 | macrophage | M5a | Y | 57.82 | 3.11 | 1.34 | 1.77 | 0.24 |
| MOLM-13 | monocytic | M5a | Y | 76.24 | 0.00 | 0.00 | NA | NA |
| TF-1 | erythroblast | M6 | N | 104.9 | 1.12 | 1.41 | 1.41 | 0.64 |
| THP-1 | monocytic | M5 | Y | ND | 96.62 | 12.13 | 12.13 | 2.46 |
| U937 | monocytic | M5 | Y | ND | 1.44 | 1.28 | 1.28 | 0.41 |
| PBMC | — | — | — | — | 174.15 | 1.88 | 1.88 | 0.90 |

AB = French-American-British classification;
IL = interleukin;
LPS = lipopolysaccharide;
NA = not available;
ND = not determinable;
PBMC = peripheral blood mononuclear cells.

Example 2: Effect of Caspase Inhibition on Compound 1 Induced IL-1β

Figure 2:
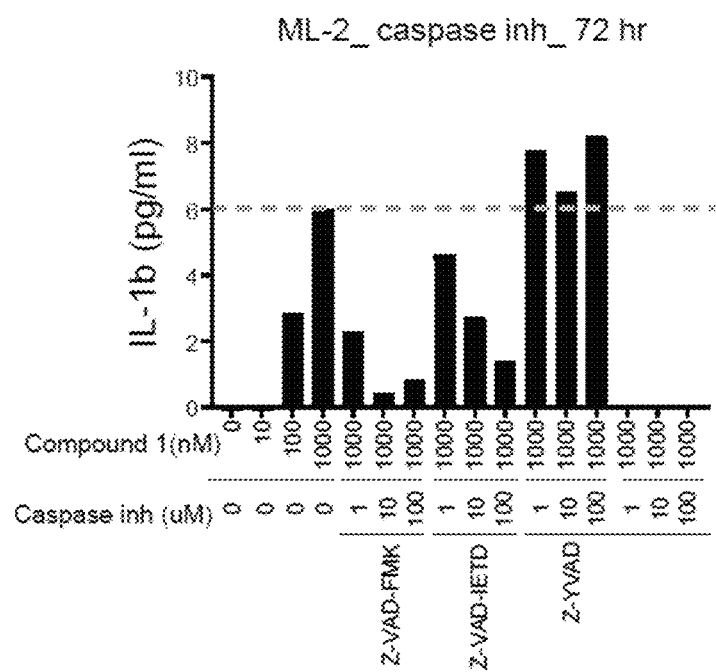
FIGS. 2A-2D demonstrate the effect of genetic and pharmacological suppression of caspase 1 or caspase 8 activities on IL-1β levels in ML-2 cell line.
Figure 3A:
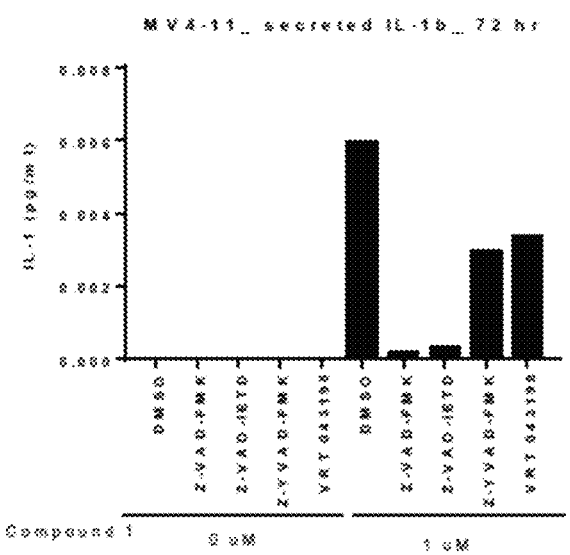
FIGS. 3A-3D demonstrate the effect of caspase inhibitors and apoptosis inducing agents on IL-1β levels in MV4-11 and ML-2 cell lines.

The effect of caspase inhibition on Compound 1 induced IL-1β in ML-2 and MV4-11 cell lines was studied by assessing whether IL-1β release was mediated by caspase 1 and/or caspase 8. FIG. 2A shows IL-1β levels measured by an electrochemiluminescence assay, in ML-2 cells treated with a combination of 1000 nM Compound 1 and 1, 10, 100 μM pan-caspase (Z-VAD-FMK), caspase 8 (Z-VAD-FMK) or caspase 1 inhibitors (Z-VAD-IETD or Z-YVAD). FIG. 3A shows IL-1β levels measured by an electrochemiluminescence assay, in MV411 cells treated with a combination of 1000 nM Compound 1 and 10 μM pan-caspase (Z-VAD-FMK), caspase 8 (Z-VAD-FMK) or caspase 1 inhibitors (Z-VAD-IETD or Z-YVAD). Pan-caspase and caspase-8 inhibitors, Z-VAD-FMK and Z-VAD-IETD respectively, significantly blocked secreted IL-1β induction by Compound 1, suggesting IL-1β induction was caspase 8 dependent. In contrast, caspase 1 inhibition by Z-YVAD or VRT043198 did not suppress IL-1β induction to nearly the same extent as pan- or caspase 8 inhibitors, suggesting that caspase 8, but not caspase 1, is the main contributor to Compound 1 induced IL-1β release.

Figure 2B:
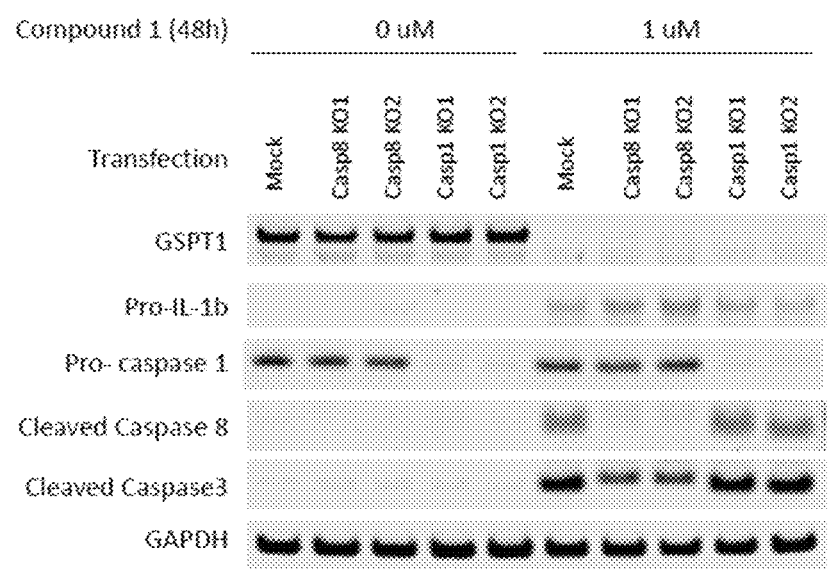
Figure 2C:
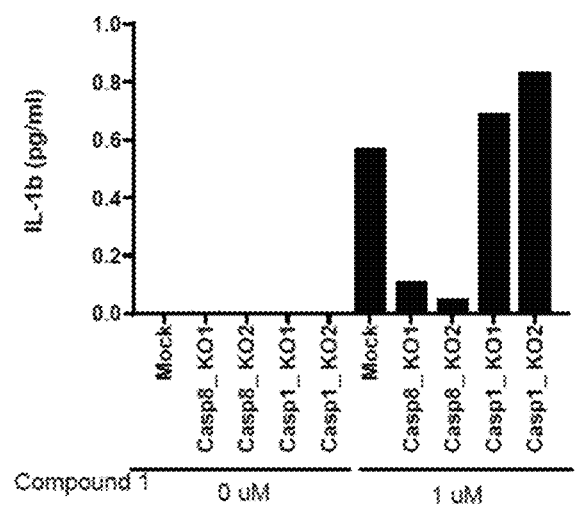

To further confirm if caspase 8 is necessary for Compound 1 induced IL-1β upregulation and/or release, knock out studies were performed. Caspase 1 or caspase 8 was knocked out by CRISPR/Cas9 in ML-2 cells, and the effect of Compound 1 on intracellular and secreted IL-1β levels was investigated. Parental, caspase 1 and caspase 8 knock out cells were treated with or without 1 µM Compound 1. IL-1β levels were analyzed 48 and 72 hours post-compound treatment in cell lysate and culture supernatant. Upregulation of pro-IL-13 and increased secreted IL-1β were evident in parental and caspase 1 knock out cells treated with Compound 1 (see FIGS. 2B and 2C). In contrast, while pro-IL upregulation by Compound 1 remains intact (FIG. 2B), induction of IL-1 release by Compound 1 was compromised in caspase 8 knock out cells (FIG. 2C). These data indicate that IL-1β release, but not pro-IL-13 upregulation, by Compound 1 is downstream of caspase 8 activation (FIGS. 7A and 7B) and independent of caspase 1.

Figure 2D:
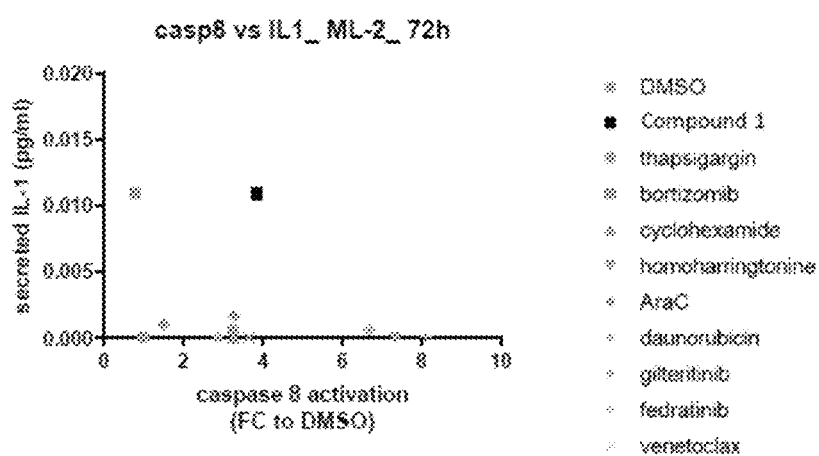
Figure 3B:
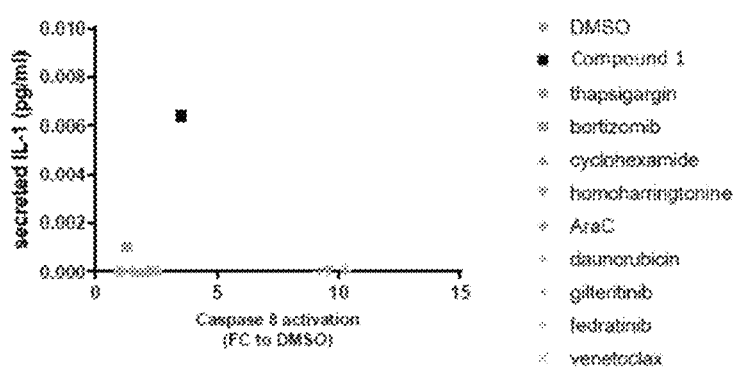
Figure 3C:
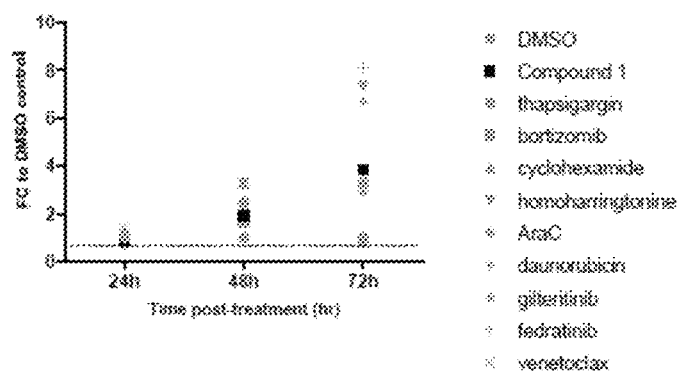
Figure 3D:
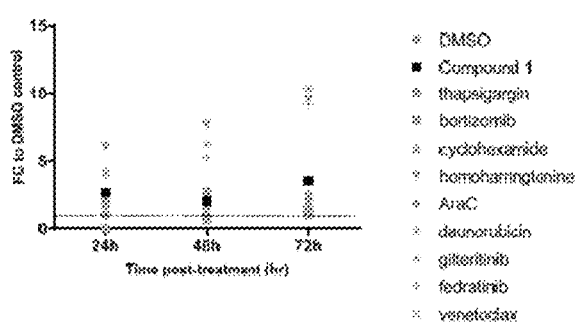

Next, tests were performed to see if caspase 8 activation alone is sufficient to mediate IL-1β induction. Using a panel of compounds that has similar but not identical mechanism of action to Compound 1, it was observed that agents, such as homoharringtonine, daunorubicin and fedratinib, that elicit higher extent of caspase 8 activation than Compound 1 were not able to induce secreted IL-1β as efficiently as Compound 1 in ML-2 (FIG. 2D) and MV4-11 (FIG. 3B) cell lines, suggesting caspase 8 activation per se is not sufficient to induce IL-1β release. To ensure caspase 8 activity was captured at an appropriate time frame, caspase 8 activation levels at 24, 48 and 72 hours were measured (FIGS. 3C and 3D) using a caspase 8/FLICE activity colorimetric assay. Compound 1 was not the most efficient caspase 8 activating compound across all time points tested, yet produced markedly more secreted IL-1β compared to all other compounds tested. Collectively, these results suggest that caspase 8 activation is necessary, but not sufficient, for Compound 1 mediated IL-1β induction.

Example 3: Effect of Compound 1 on IL-1β Induction

Figure 4A:
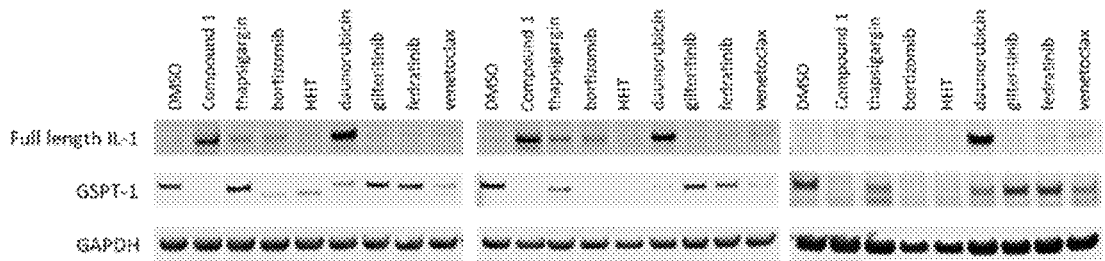
FIGS. 4A-4C illustrates the effect of compounds on IL-1β induction and apoptosis in ML-2 cell line.
Figure 4B:
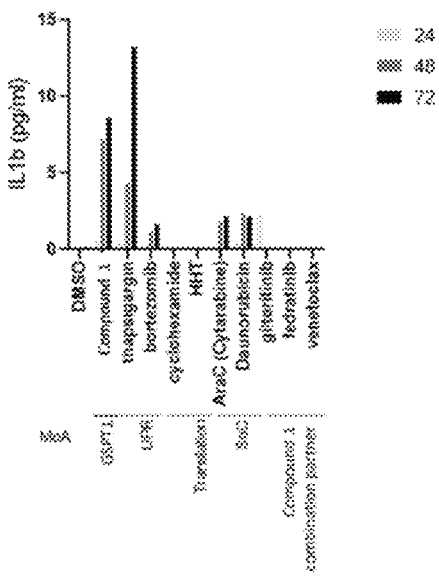
Figure 4C:
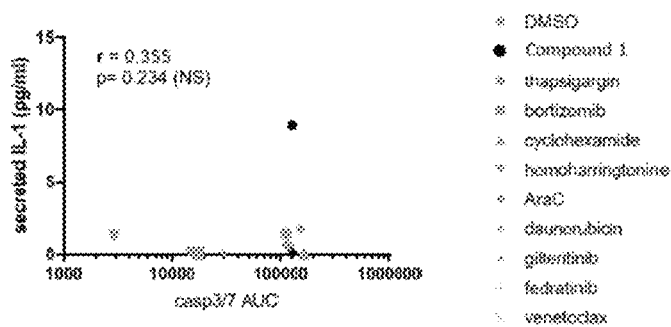
Figure 5A:
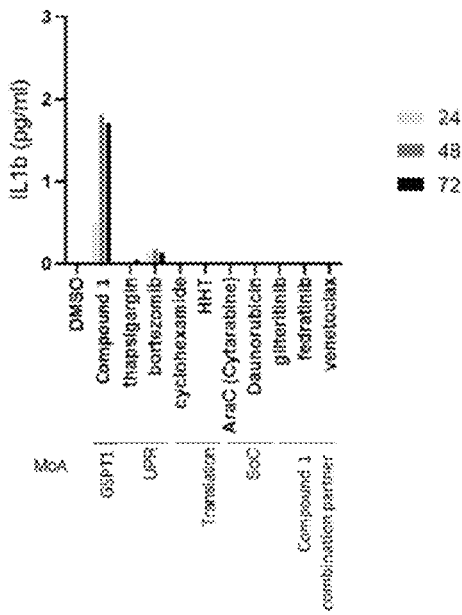
FIG. 5A demonstrates the effect of test compounds on IL-1β induction in MV4-11 cell lines measured by an electrochemiluminescence assay.
Figure 5B:
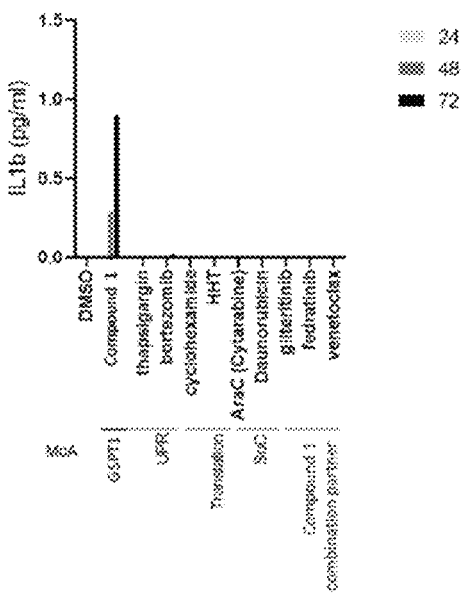
FIG. 5B demonstrates the effect of test compounds on IL-1β induction in MOLM13 cell lines measured by an electrochemiluminescence assay.
Figure 6A:
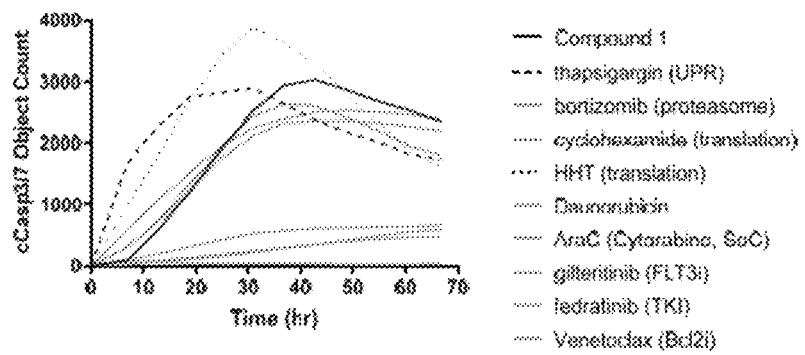
FIGS. 6A-6B demonstrate the effect of test compounds on apoptosis and viability in ML-2 cell line.
Figure 6B:
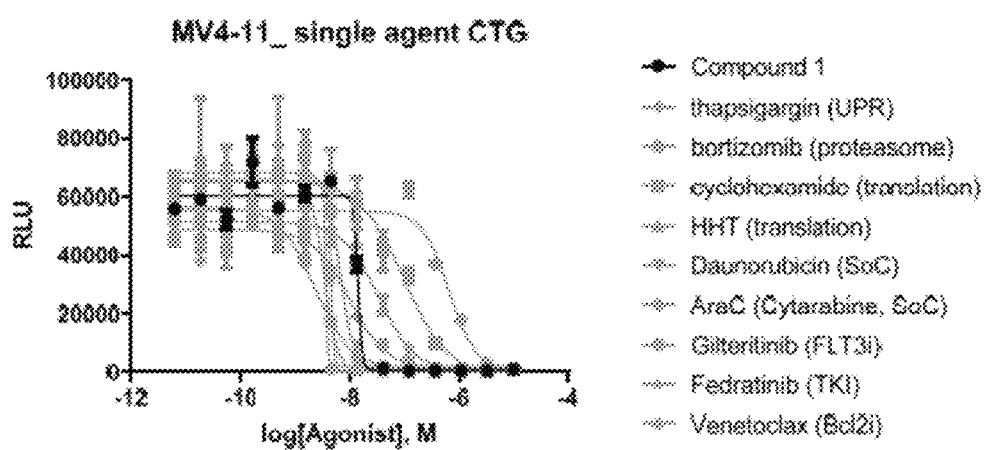
Figure 7:
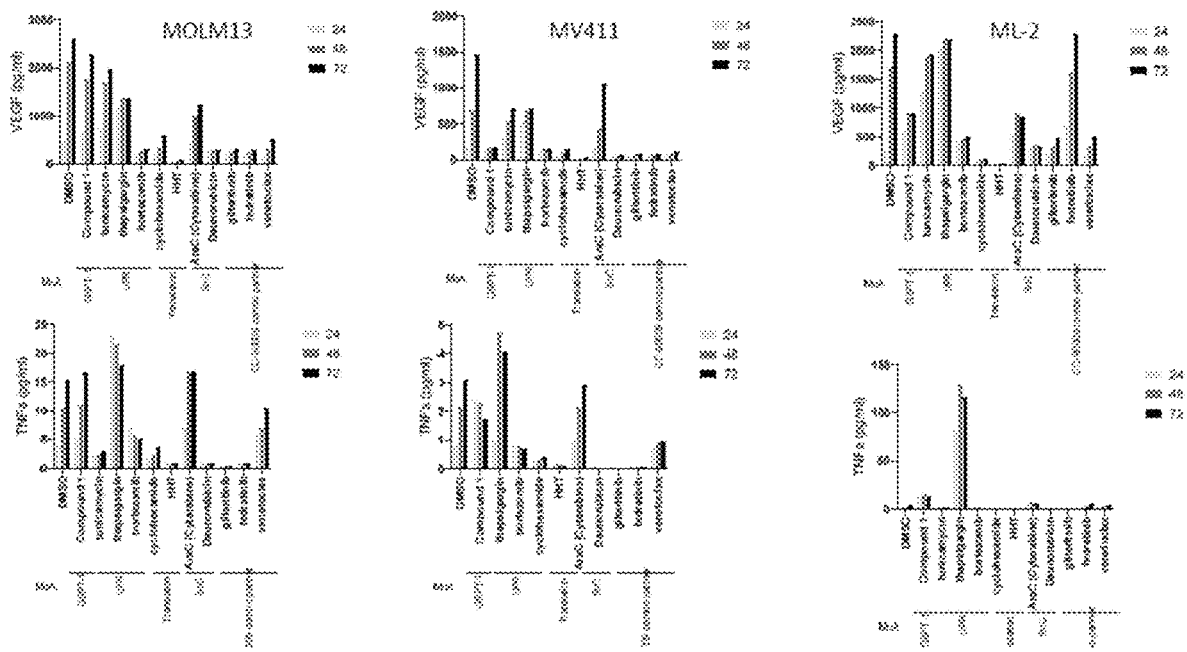
FIG. 7 demonstrates the effect of test compounds on VEGF and TNFa levels in ML-2, MV4-11 and MOLM13 cell lines measured by an electrochemiluminescence assay.

To further explore the mechanisms underlying IL-1β induction by Compound 1, and compounds with different, but related mechanisms to Compound 1 were tested in three AML cell lines, ML-2, MV4-11 and MOLM-13 (FIG. 4 and FIG. 5). Compound 1 degrades GSPT1 through cereblon mediated protein degradation, which leads to global translation inhibition, activation of ISR and subsequently apoptosis. Compound 1 conferred induction of both intracellular pro-IL-13 and secreted IL-1β. In contrast, unfolded protein response inducers (thapsigargin and bortezomib), translation inhibitors (cycloheximide and HHT), kinase inhibitors (gilteritinib for FLT3, fedratinib for JAK2), and apoptosis inducers (venetoclax for BCL-2), were not able to induce high levels of intracellular pro-IL-13 (FIG. 4A) nor secreted IL-1β (FIG. 4B) at the doses that conferred similar extent of caspase3/7 activation and viability loss (FIG. 4C; FIG. 6), suggesting IL-1β induction and release were not a general phenomenon of rapid cell kill, although being apoptosis related, and is associated with GSPT1 loss. A cereblon-modulating agent with a different target protein, CK1α, also failed to demonstrate ability to induce intracellular pro-IL 1β nor secreted IL-1β, suggesting IL-1β induction is not a general cereblon-modulating agent-mediated effect. Low levels of IL-1β was induced by thapsigargin and bortezomib, consistent with literature report that ER stress could lead to caspase 8 activation and IL-1β production (Shenderov et al. J Immunol. 2014 Mar. 1; 192(5): 2029-2033). Similar results were observed in two other AML cell lines, MV4-11 and MOLM-13 (FIGS. 5A and 5B, respectively). To assess if GSPT1 degradation leads to pan-cytokine induction or specific to IL-1β, the compound effect was compared on the levels of two other known hypotension inducing cytokines, TNFa and VEGF (FIG. 7). In contrast to IL-1β, Compound 1 did not induce more VEGF nor TNFa compared to other mechanistic agents. Collectively, these data support a unique effect of GSPT1 degradation on IL-1β induction.

Example 4: Effect of GSPT1 Degradation on IL-1β Induction

Figures 8B, 8C:
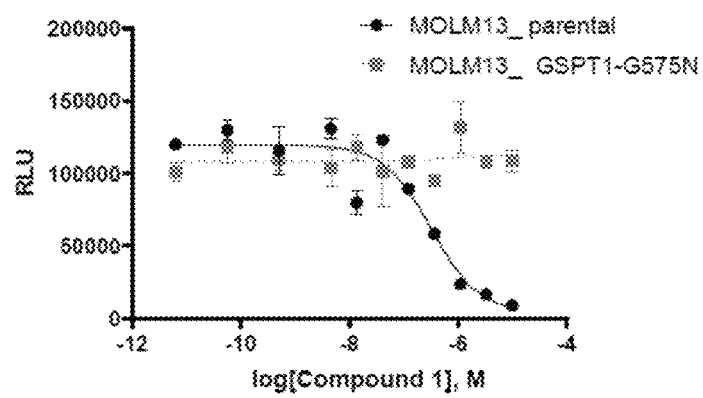
Figure 8D:
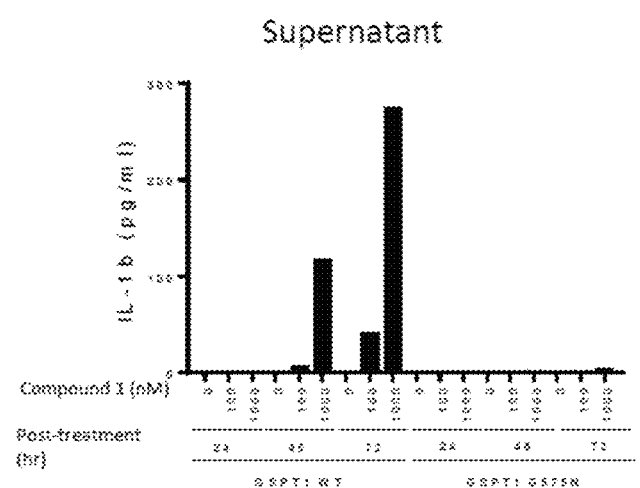

To further confirm if IL-1β induction is an on-target effect of GSPT1 degradation, intracellular pro-IL-1β and secreted IL-1βb levels in response to Compound 1 treatment were compared in an isogenic MOLM13 cell pair either expressing endogenous wildtype GSPT1 or overexpressing a non-degradable form of GSPT1 G575N. GSPT1 G575N conferred complete resistance to Compound 1 mediated GSPT1 degradation, caspase 3 activation and viability loss (FIGS. 8A and 8B). Importantly, pro-IL-1 (FIG. 8A), intracellular and supernatant IL-1β induction (FIGS. 8C and 8D) were completely blocked by overexpression of GSPT1 G575N, proving both pro-IL-13 upregulation and matured IL-1β induction are on-target effects downstream of GSPT1 degradation.

Example 5: Effect of GCN2 Pathway Activation on IL-1β Induction

Figure 9A:
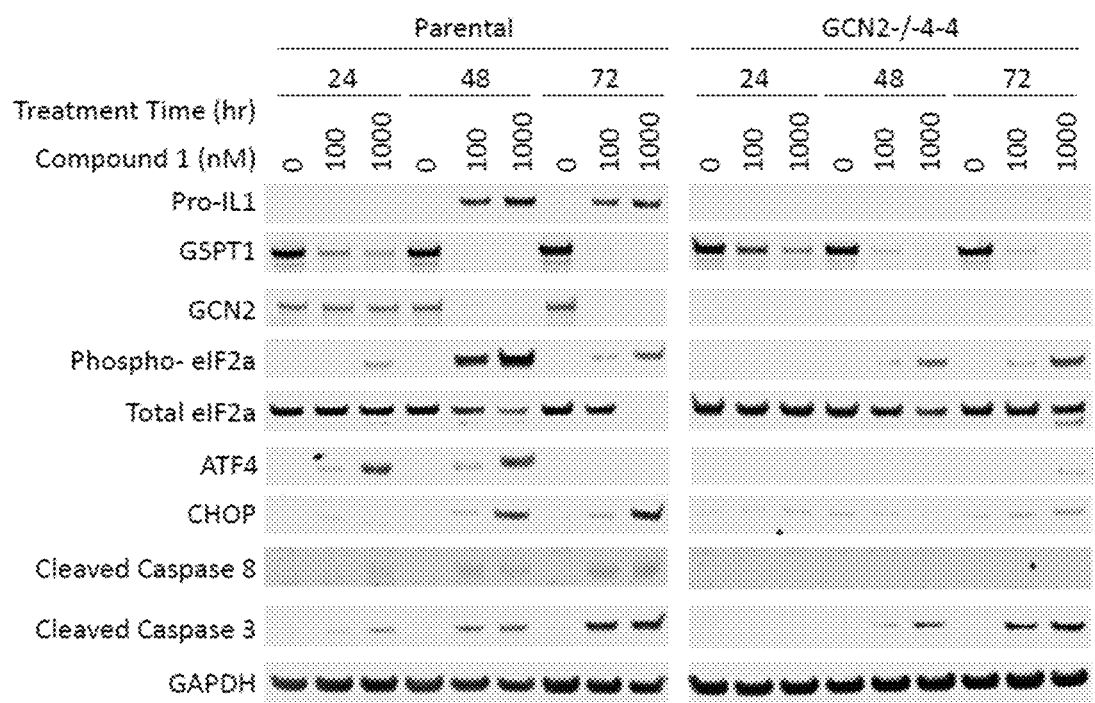
FIGS. 9A-9C illustrate the effect of GCN2 pathway on IL-1β induction by Compound 1 in an isogenic MOLM13 cell pair expressing wildtype GCN2 or CRISPR/cas9 knock down of GCN2.
Figure 9B:
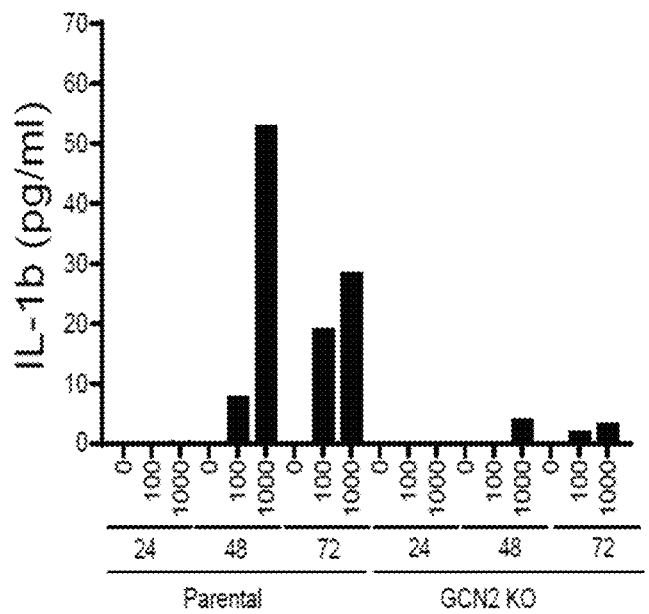
Figure 9C:
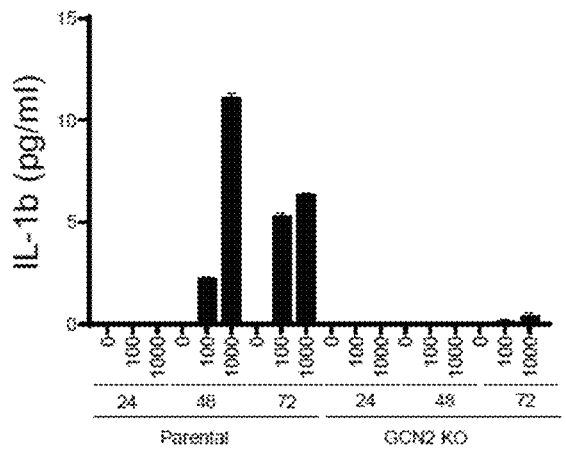

ISR, especially via GCN2 pathway, is one of the key pathways contributed to GSPT1 mediated cell death. GCN2 knock down blocked ATF4 and CHOP induction by Compound 1, and suppressed caspase 3 and caspase 8 activation. GCN2 has been implicated in IL-1β production. GCN2 activation inhibit classical caspase 1 mediated inflammasome activation in intestinal cells and that GCN2 knock down in CD11c+ antigen presenting cells or intestinal epithelial cells leads to enhanced inflammasome activation and IL-1β production. (Ravindran et al. *Nature*. 2016, 531 (7595):523-527). To understand if Compound 1 mediated IL-1β induction is downstream of GCN2 pathway, an isogenic MV4-11 Cas9 cell pair either expressing endogenous wildtype GCN2 or with the gene deleted was used. GCN2 knock down suppressed the induction of phosphor-eIF2a, ATF4, CHOP and cleaved caspase 8 by Compound 1 (FIG. 9A). Notably, Compound 1 mediated pro-IL-1β upregulation was abolished in the absence of GCN2 (FIG. 9A). Similarly, intracellular and supernatant IL-1β induction (FIGS. 9B and 9C, respectively) by Compound 1 was markedly suppressed in GCN2 knock out cells compared to parental cells. These evidences pointed that pro-IL-13 up-regulation and secreted IL-1β induction are both downstream effects of GCN2 pathway activation, and distinct from the GCN2 mediated classical inflammasome pathway inhibition reported in gut cells (Ravindran et al. *Nature*. 2016, 531(7595):523-527).

Example 6: Effect of Dexamethasone on Compound 1 Mediated IL-1β Induction

Figure 10A:
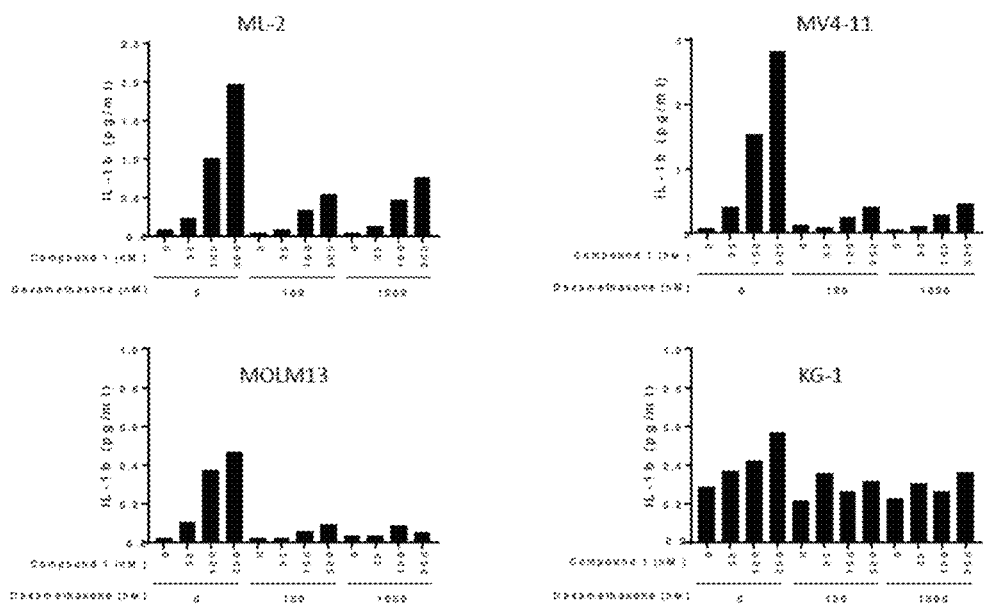
FIGS. 10A-10C demonstrate the effect of dexamethasone on Compound 1 mediated IL-1β induction, apoptosis and viability loss.

The effect of dexamethasone on IL-1β levels induced by Compound 1 in AML cell lines was tested. FIG. 10A shows that 100 and 1000 nM dexamethasone markedly reduced secreted IL-1β levels induced by Compound 1 in 4 AML cell lines, ML-2, MV4-11, MOLM13 and KG1.

Figure 10B:
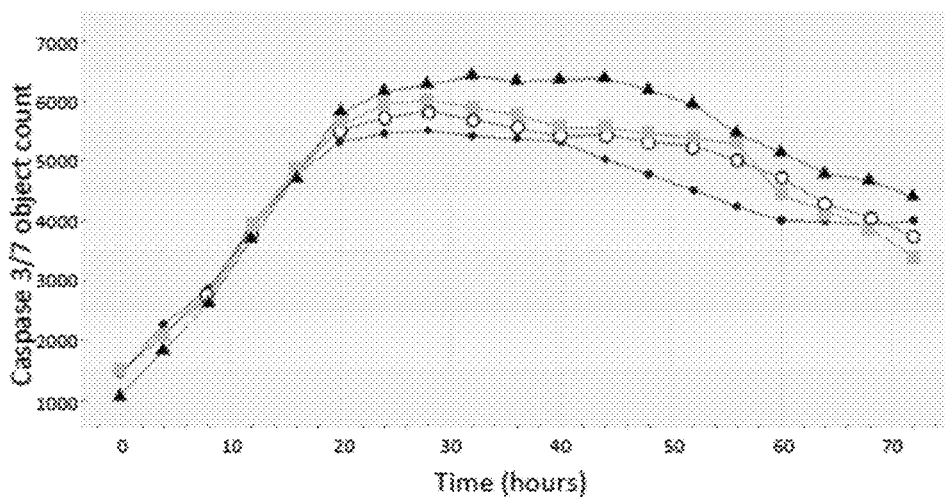
Figure 10C:
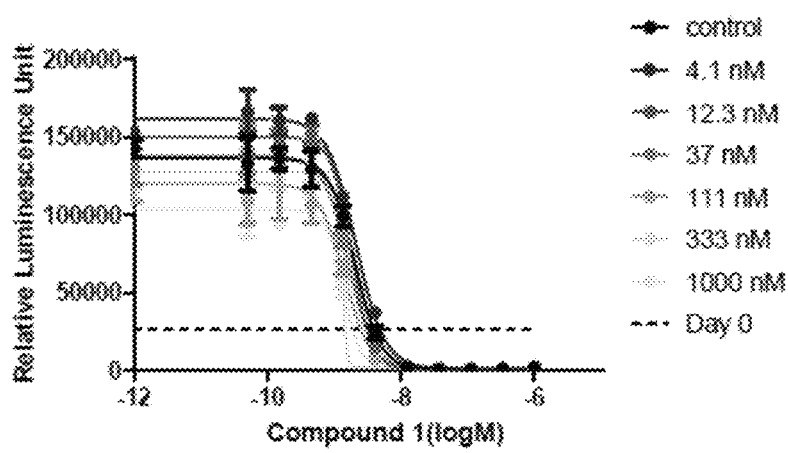

Next, effect of co-treatment of dexamethasone was tested on the efficacy profile of Compound 1 in AML cells. This is important as increased levels of cell kill may lead to cytokine release syndrome, whereas reduced rate or depth of apoptosis may lead to insufficient tumor kill and post the risk of blast rebound. It was observed that dexamethasone combination does not alter rate nor depth of caspase3/7 activation compared to Compound 1 single agent treatment (FIG. 10B). Consistently, total cell viability measured by a CellTitre-Glo assay showed that dexamethasone did not alter $EC_{50}$ of Compound 1 (FIG. 10C). These results suggest dexamethasone dose not interfere with killing kinetics of Compound 1 on AML cells, supporting clinical application of dexamethasone in preventing hypotension.

Figure 11:
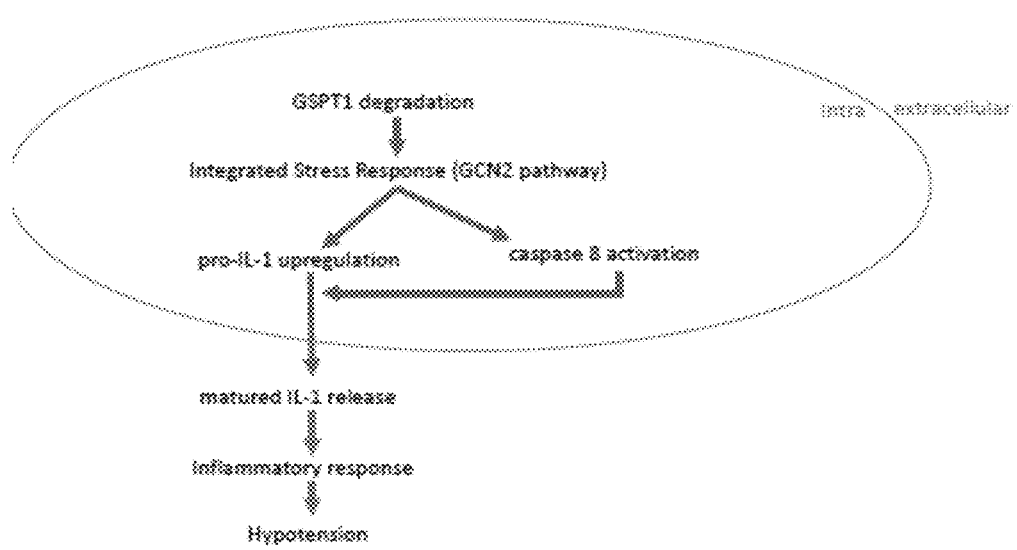
FIG. 11 provides a schematic depiction of an IL-1β induction mechanism by Compound 1.

FIG. 11 provides a schematic depiction of an IL-1β induction mechanism by Compound 1. As indicated in FIG. 11, GSPT1 degradation upon Compound 1 treatment turns on GCN2 pathway, which upregulates pro-IL-1 and activates caspase 8. Activated caspase 8 processed pro-IL-1 into matured IL-1β, which is subsequently released out of cells, causing inflammatory response and potentially hypotension.

Example 7: Effect of Second Agents on Compound 1 Mediated IL-1β Induction

Figure 12:
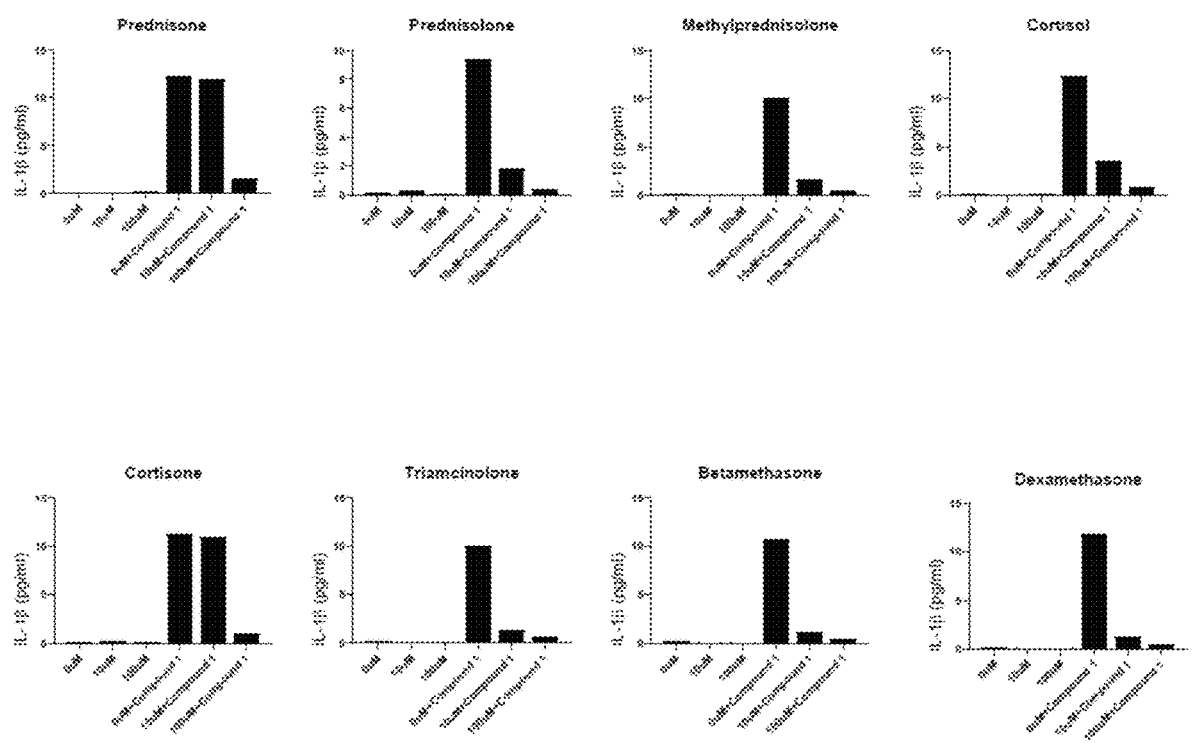
FIG. 12 shows that Compound 1 induced IL-1b can be suppressed by prednisone, prednisolone, methylprednisolone, cortisol, cortisone, triamcinolone, betamethasone and dexamethasone in ML-2 cell line.
Figure 13:
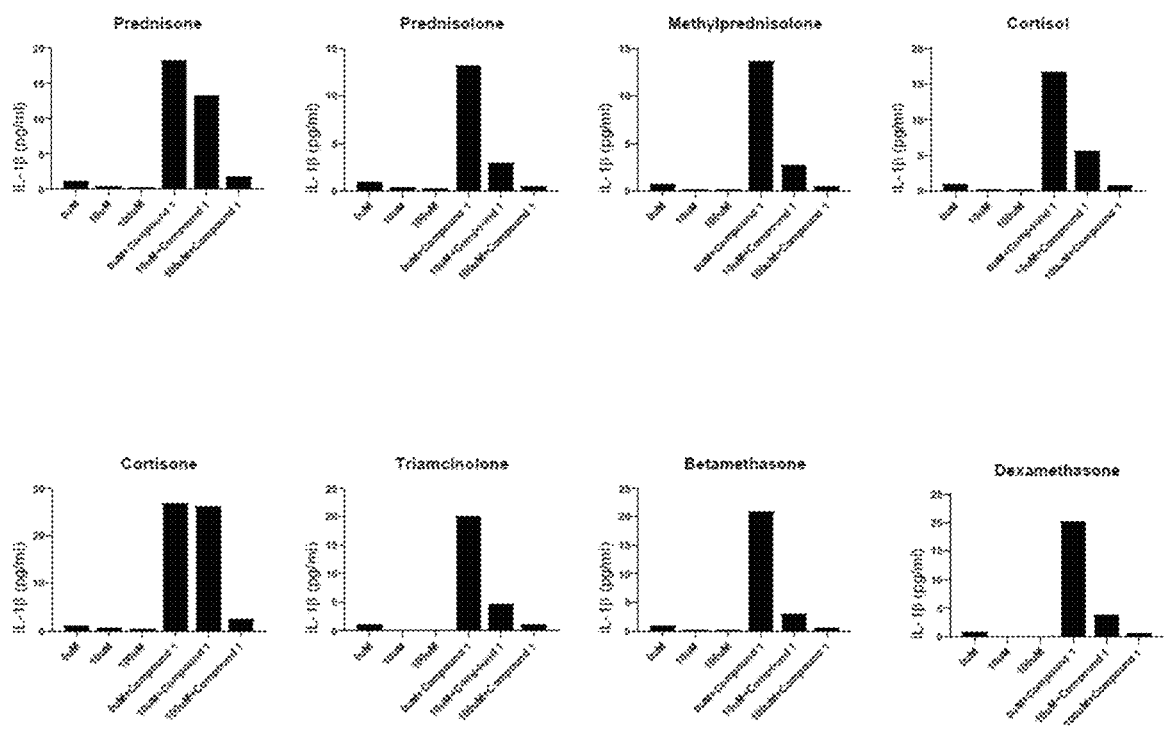
FIG. 13 shows that Compound 1 induced IL-1b can be suppressed by prednisone, prednisolone, methylprednisolone, cortisol, cortisone, triamcinolone, betamethasone and dexamethasone in MOLM13 cell line.

The effect of prednisone, prednisolone, methylprednisolone, cortisol, cortisone, triamcinolone, betamethasone and dexamethasone on IL-1β levels induced by Compound 1 in two AML cell lines, ML-2 and MOLM13, was tested. FIGS. 12 and 13 show that Compound 1 induced IL-1b can be suppressed by prednisone, prednisolone, methylprednisolone, cortisol, cortisone, triamcinolone, betamethasone and dexamethasone in ML-2 and MOLM13 cell lines, respectively.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed:

1. A method of suppressing interleukin-10 induction related to 2-(4-chlorophenyl)-N-((2-(2,6-dioxopiperidin-3-yl)-1-oxoisoindolin-5-yl)methyl)-2,2-difluoroacetamide, or a stereoisomer or mixture of stereoisomers, pharmaceutically acceptable salt, tautomer, prodrug, solvate, hydrate, or clathrate thereof (Compound 1) in an acute myeloid leukemia patient, wherein the method comprises administering to the patient a therapeutically effective amount of Compound 1 and a therapeutically effective amount of second agent selected from prednisone, prednisolone, methylprednisolone, cortisol, cortisone, triamcinolone, betamethasone and dexamethasone.

2. The method of claim 1, wherein the second agent is dexamethasone.

3. The method of claim 1, wherein the interleukin-10 induction is suppressed by about 10% to 90%.

4. The method of claim 1, wherein the therapeutically effective amount of Compound 1 is about 0.1 mg to about 10 mg.

5. The method of claim 1, wherein the therapeutically effective amount of Compound 1 is about 0.3 mg, 0.6 mg, 1.2 mg, 1.8 mg, 2.4 mg, 3 mg, 3.6 mg, 4.5 mg, 5.4 mg or 8.1 mg per day.

6. The method of claim 1, wherein Compound 1 is administered on days 1 to 5 of a 28 day treatment cycle.

7. The method of claim 6, wherein the treatment cycle comprises a rest period of 23 days.

8. The method of claim 1, wherein Compound 1 is administered on days 1 to 5 of a 42 day treatment cycle.

9. The method of claim 1, wherein Compound 1 is administered on days 1 to 3 of a 28 day treatment cycle.

10. The method of claim 1, wherein Compound 1 is administered on days 1 to 5 and days 15 to 19 of a 28 day treatment cycle.

11. The method of claim 6, wherein the treatment cycle is repeated at least once.

12. The method of claim 11, wherein the treatment cycle is repeated 2 to 4 times.

13. The method of claim 1, wherein the method comprises administering one or more of calcium, calcitriol, or vitamin D supplementation.

14. The method of claim 1, wherein the method comprises administering one or more of calcium, calcitriol, or vitamin D supplementation prior to Compound 1.

15. The method of claim 1, wherein the method comprises administering one or more of calcium, calcitriol, or vitamin D supplementation at least 3 days prior to Compound 1 on day 1 of the cycle.

16. The method of claim 13, wherein the patient does not have a disorder disrupting normal calcium homeostasis or preventing calcium supplementation.

17. The method of claim 1, further comprising administering a therapeutically effective amount of another additional active agent or a supportive care therapy.

18. The method of claim 17, wherein the additional active agent is selected from a hematopoietic growth factor, a cytokine, anti-cancer agent, an antibiotic, a cox-2 inhibitor, an immunomodulatory agent, an immunosuppressive agent, a corticosteroid or a pharmacologically active mutant or derivative thereof and a therapeutic antibody that specifically binds to a cancer antigen.

* * * * *

UNITED STATES PATENT AND TRADEMARK OFFICE
CERTIFICATE OF CORRECTION

| | | |
|---|---|---|
| PATENT NO. | : 12,090,147 B2 | Page 1 of 1 |
| APPLICATION NO. | : 17/089359 | |
| DATED | : September 17, 2024 | |
| INVENTOR(S) | : Tonia Buchholz et al. | |

It is certified that error appears in the above-identified patent and that said Letters Patent is hereby corrected as shown below:

On the Title Page

Item [54], replace "DIOXOIPERIDIN" with --DIOXOPIPERIDIN--

In the Specification

In Column 1, Lines 2-3, replace the term "DIOXOIPERIDIN" with --DIOXOPIPERIDIN--

In the Claims

In Column 101, Claim 1, Line 46, replace the term "interleukin-10" with --interleukinβ--

In Column 102, Claim 3, Line 6, replace the term "interleukin-10" with --interleukinβ--

Signed and Sealed this
Twenty-first Day of January, 2025

Coke Morgan Stewart
*Acting Director of the United States Patent and Trademark Office*